(12) United States Patent
Miller et al.

(10) Patent No.: US 10,307,157 B2
(45) Date of Patent: Jun. 4, 2019

(54) SURGICAL STAPLER WITH ANVIL SEATING DETECTION

(71) Applicant: Ethicon Endo-Surgery, LLC, Guaynabo, PR (US)

(72) Inventors: Christopher C. Miller, Loveland, OH (US); Richard F. Schwemberger, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 597 days.

(21) Appl. No.: 14/751,247

(22) Filed: Jun. 26, 2015

(65) Prior Publication Data

US 2016/0374667 A1 Dec. 29, 2016

(51) Int. Cl.
| | |
|---|---|
| *A61B 17/068* | (2006.01) |
| *A61B 17/115* | (2006.01) |
| *A61B 17/072* | (2006.01) |
| *A61B 17/29* | (2006.01) |
| *A61B 90/00* | (2016.01) |

(52) U.S. Cl.
CPC ........ *A61B 17/068* (2013.01); *A61B 17/1155* (2013.01); *A61B 2017/07257* (2013.01); *A61B 2017/2946* (2013.01); *A61B 2090/0811* (2016.02)

(58) Field of Classification Search
CPC ...... A61B 17/1155; A61B 2017/07257; A61B 2017/00398; A61B 2017/00473; A61B 2017/00477; A61B 2090/0811; A61B 2090/0812
See application file for complete search history.

(56) References Cited

U.S. PATENT DOCUMENTS

| | | | |
|---|---|---|---|
| 5,205,459 A | 4/1993 | Brinkerhoff et al. | |
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A * | 8/1994 | Main ................... | A61B 17/115 227/179.1 |

(Continued)

OTHER PUBLICATIONS

International Search Report and Written Opinion dated Sep. 26, 2016 for Application No. PCT/US2016/038875, 10 pgs.

(Continued)

*Primary Examiner* — Andrew M Tecco
(74) *Attorney, Agent, or Firm* — Frost Brown Todd LLC

(57) ABSTRACT

A surgical circular stapler has a handle assembly, a shaft, a stapling assembly, and a firing assembly. The shaft extends distally from the handle assembly. The stapling assembly is secured to a distal end of the shaft. Longitudinal translation of the firing assembly causes the stapling assembly to drive a plurality of staples in a circular array to secure two lumens of tissue together. The stapling assembly may further drive a blade to sever any excess tissue interior of the circular array of staples. The stapler further includes a lockout assembly configured to control firing of the stapling assembly. The lockout assembly may include one or more switches, the actuation of which is configured to prevent or permit firing of the stapling assembly. The lockout assembly may additionally or alternatively include one or more mechanical lockout features configured to control firing of the stapling assembly.

20 Claims, 71 Drawing Sheets

(56) References Cited

U.S. PATENT DOCUMENTS

| | | | |
|---|---|---|---|
| 5,350,104 A | 9/1994 | Main et al. | |
| 5,533,661 A | 7/1996 | Main et al. | |
| 6,517,565 B1 * | 2/2003 | Whitman | A61B 17/07207 600/146 |
| 6,945,444 B2 | 9/2005 | Gresham et al. | |
| 7,794,475 B2 | 9/2010 | Hess et al. | |
| 8,408,439 B2 | 4/2013 | Huang et al. | |
| 8,453,914 B2 | 6/2013 | Laurent et al. | |
| 8,627,995 B2 * | 1/2014 | Smith | A61B 17/1114 227/179.1 |
| 8,910,847 B2 | 12/2014 | Nalagatla et al. | |
| 9,161,803 B2 | 10/2015 | Yates et al. | |
| 9,186,148 B2 * | 11/2015 | Felder | A61B 17/1155 |
| 2005/0116009 A1 * | 6/2005 | Milliman | A61B 17/068 227/176.1 |
| 2008/0185419 A1 * | 8/2008 | Smith | A61B 17/1114 227/179.1 |
| 2008/0255413 A1 * | 10/2008 | Zemlok | A61B 17/068 600/106 |
| 2013/0175318 A1 * | 7/2013 | Felder | A61B 17/1155 227/175.2 |
| 2014/0144968 A1 | 5/2014 | Shelton | |
| 2014/0144969 A1 | 5/2014 | Scheib et al. | |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166717 A1 | 6/2014 | Swayze et al. | |
| 2014/0166718 A1 | 6/2014 | Swayze et al. | |
| 2014/0166728 A1 | 6/2014 | Swayze et al. | |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |

OTHER PUBLICATIONS

European Search Report and Written Opinion dated Sep. 23, 2016 for Application No. EP16176145.7, 8 pgs.

* cited by examiner

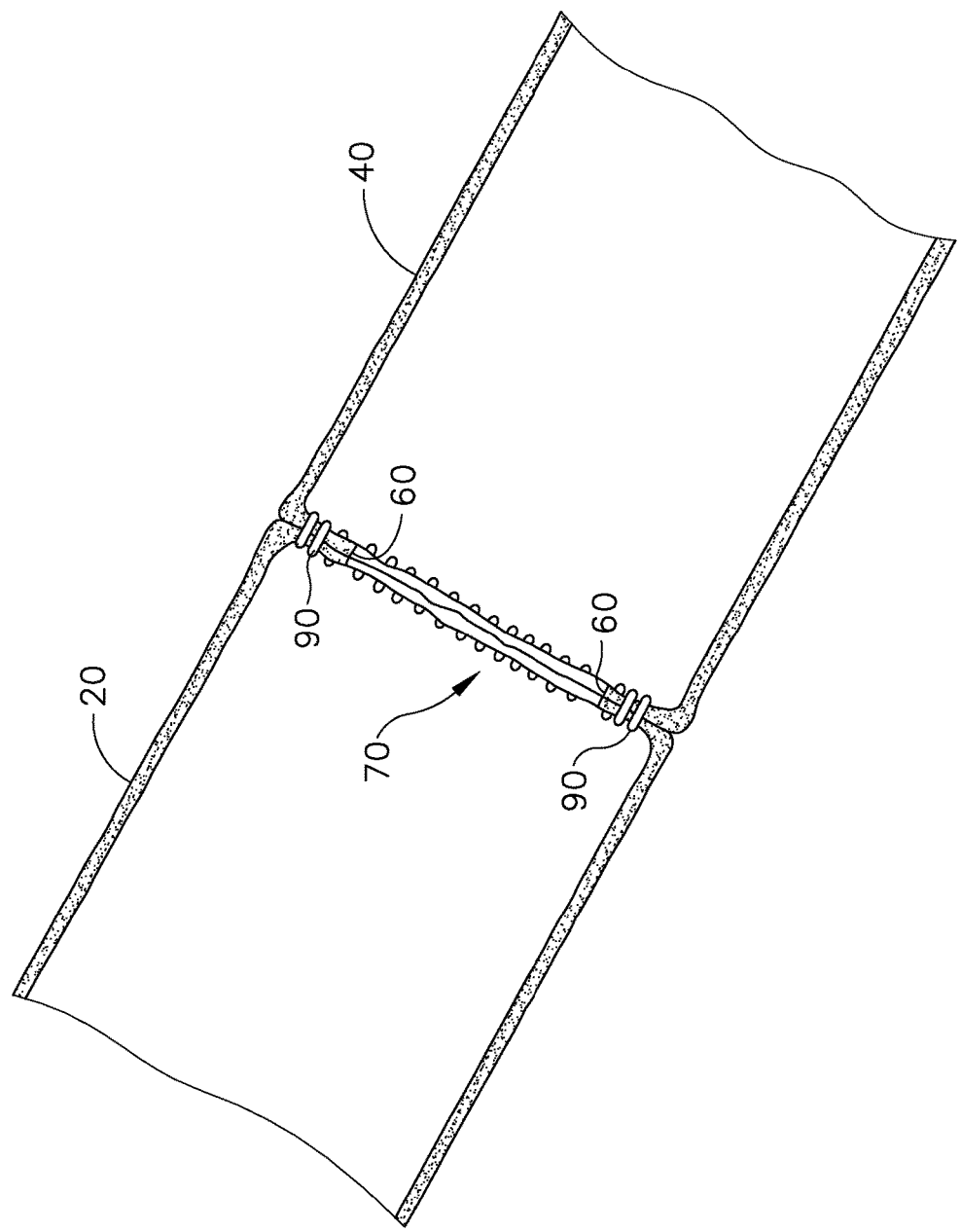

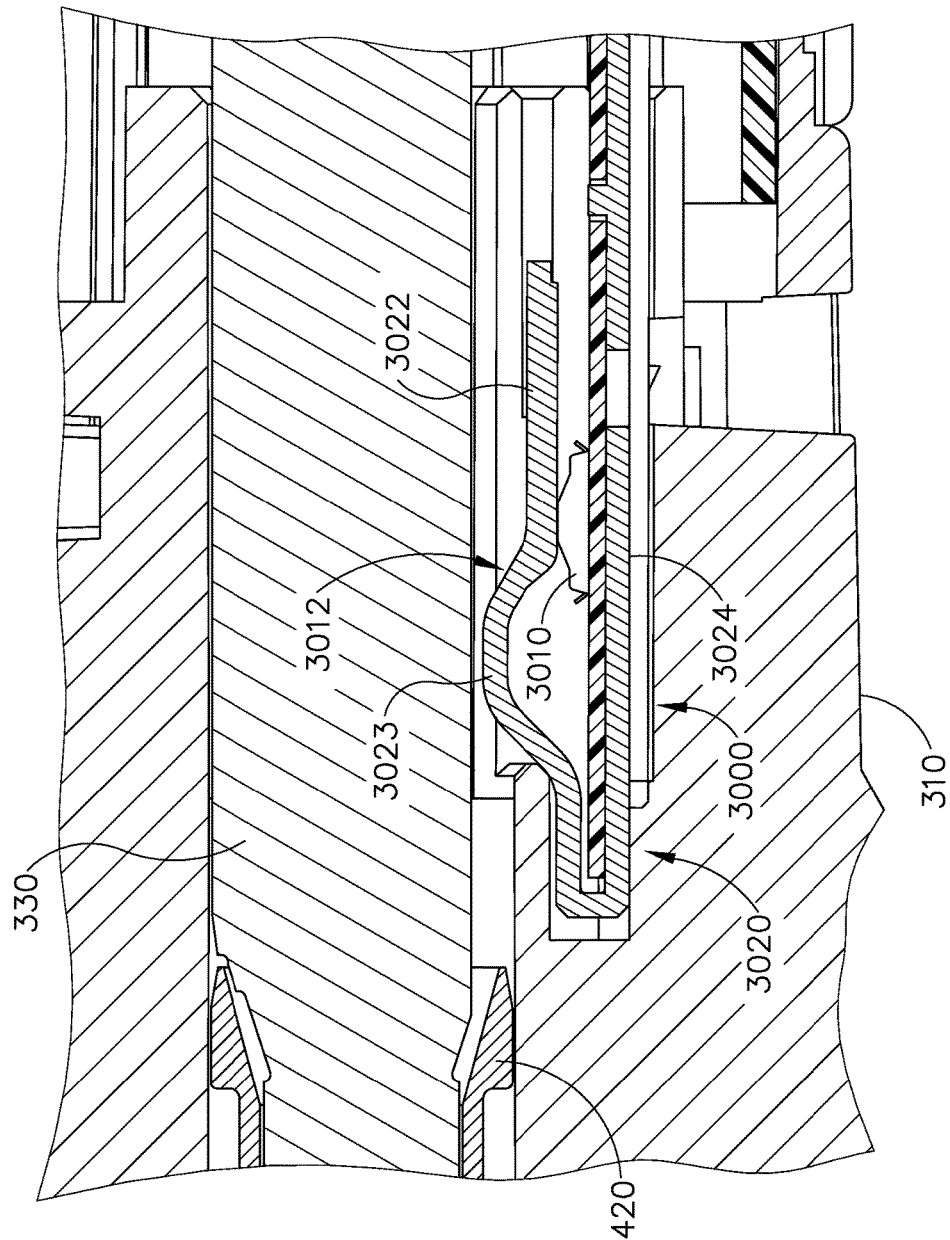

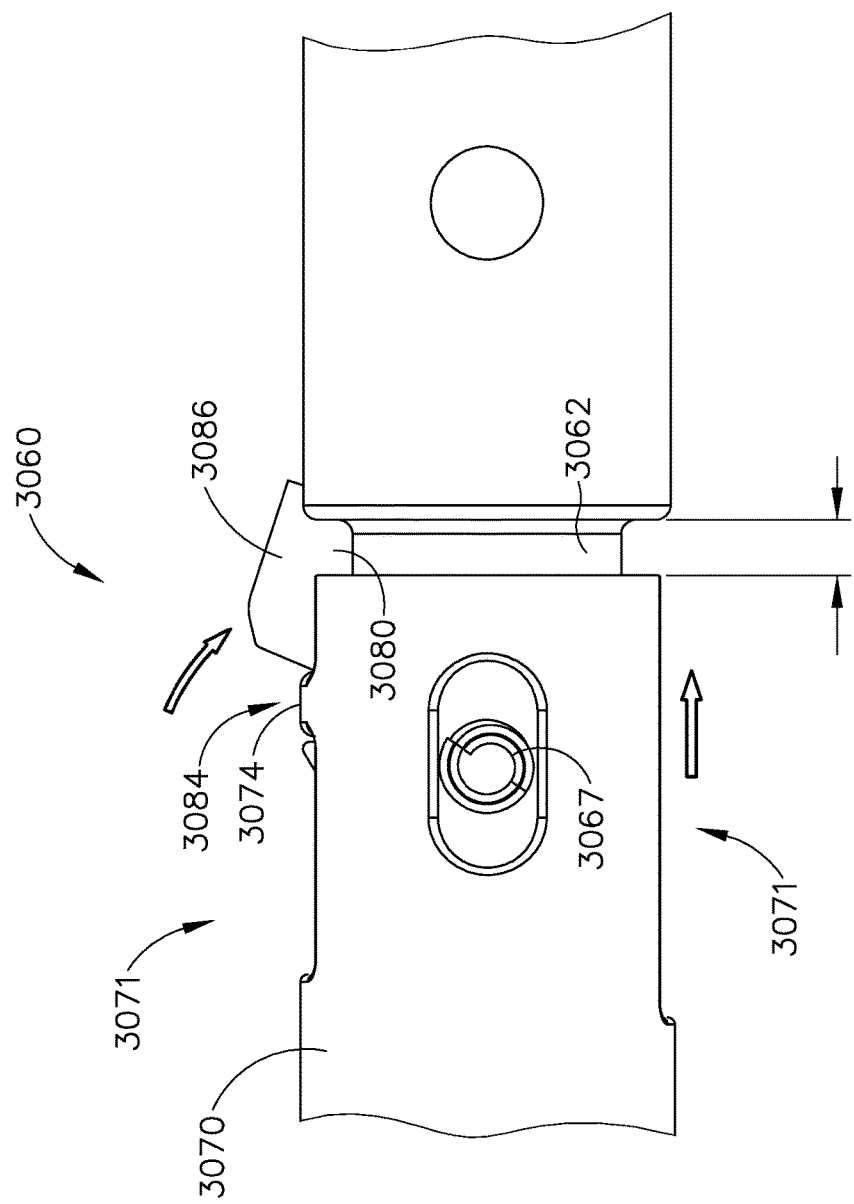

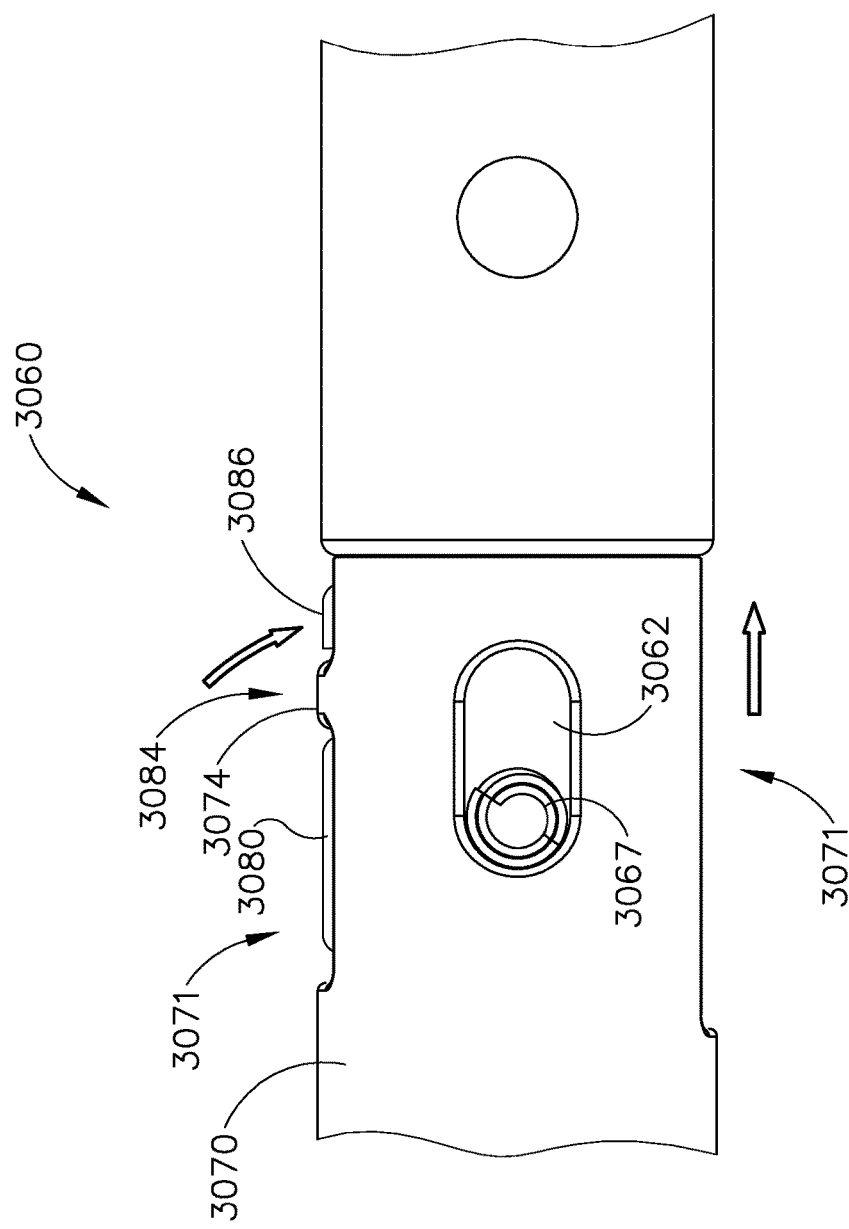

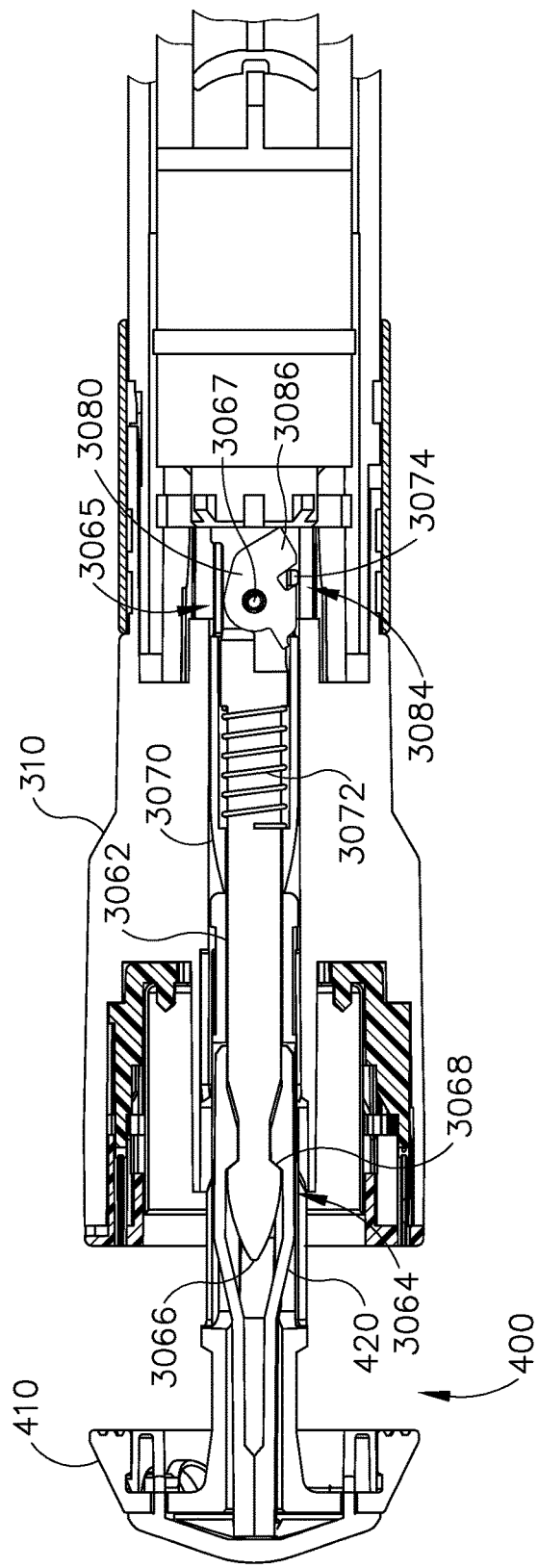

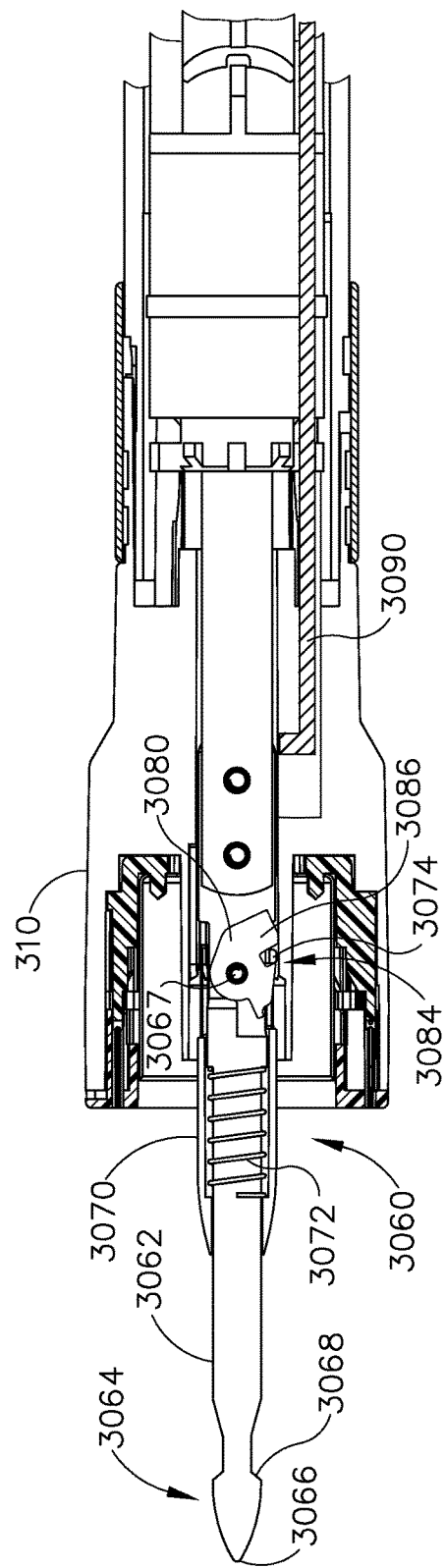

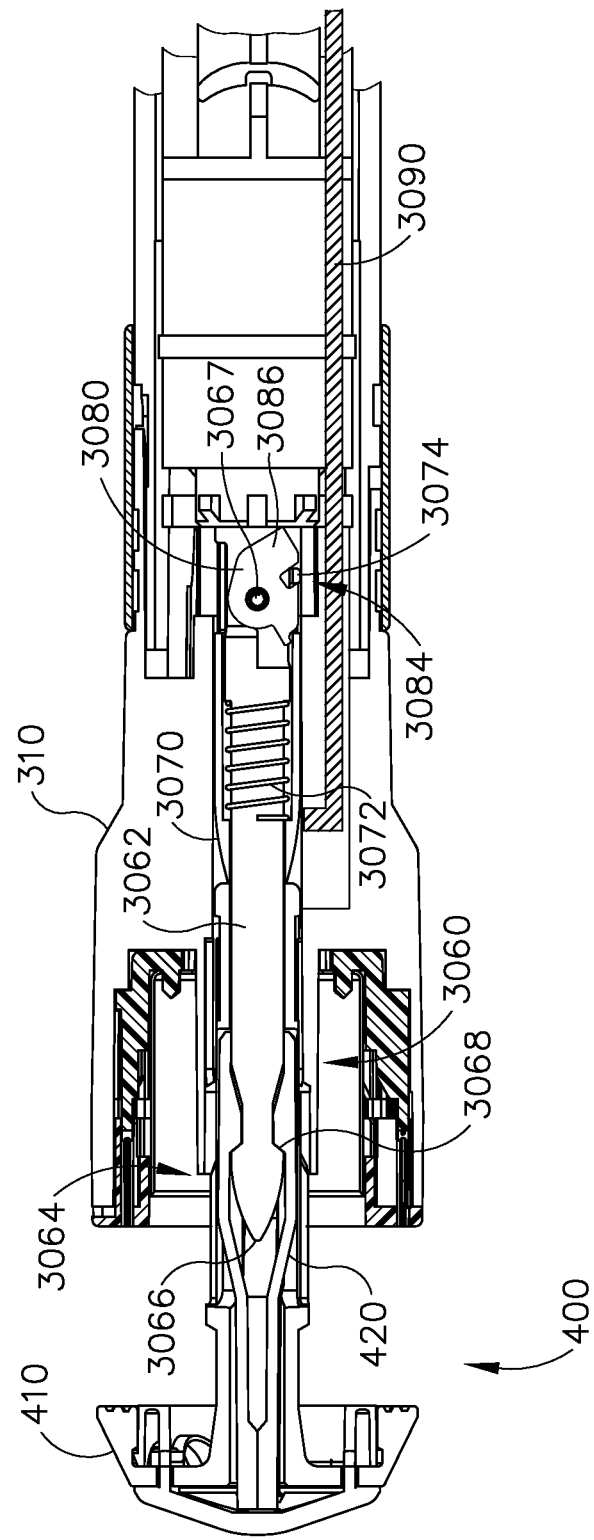

ued Jan. 4, 1994; U.S.
SURGICAL STAPLER WITH ANVIL SEATING DETECTION

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910, 847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 21E depicts a cross-sectional side view of the first and second sections of the digestive tract of FIG. 21A joined together at an end-to-end anastomosis;

FIG. 23A depicts a cross-sectional side view of the distal end of the circular stapler of FIG. 22A, with the contact switch of FIG. 22A in the open state of FIG. 22A;

FIG. 30B depicts a detailed side elevational view of the trocar of FIG. 26, with the sleeve member of FIG. 29A moved to the second position of FIG. 29B, and with the lockout member of FIG. 29A moved to the second rotational position of FIG. 29B by movement of the sleeve member to the second position;

FIG. 30C depicts a detailed side elevational view of the trocar of FIG. 26, with the sleeve member of FIG. 29A moved to the third position of FIG. 29C, and with the lockout member of FIG. 29A moved to the third rotational position of FIG. 29C by movement of the sleeve member to the third position;

Figure 26:
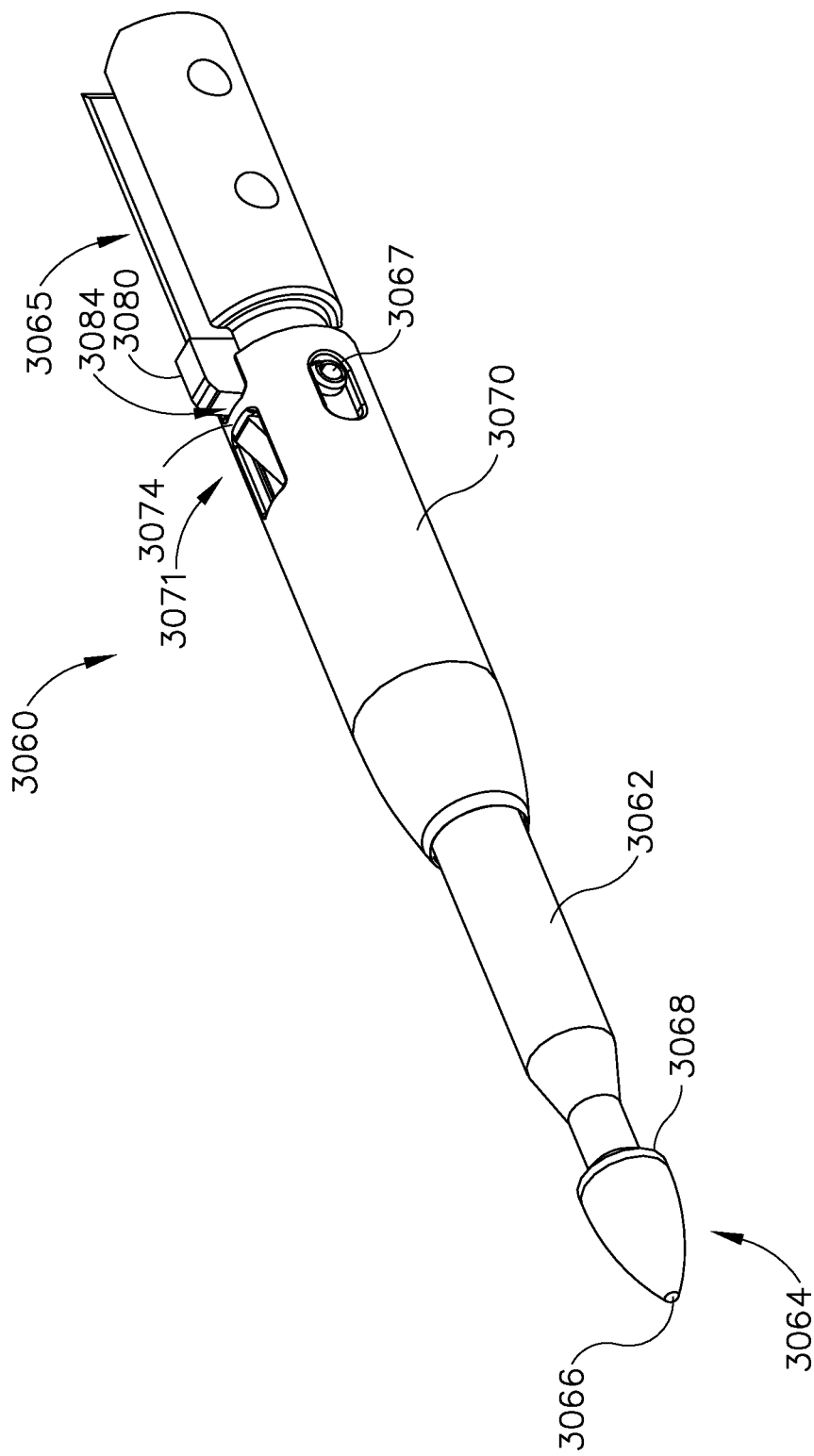
FIG. 26 depicts a perspective view of an exemplary alternative trocar.
Figure 29A:
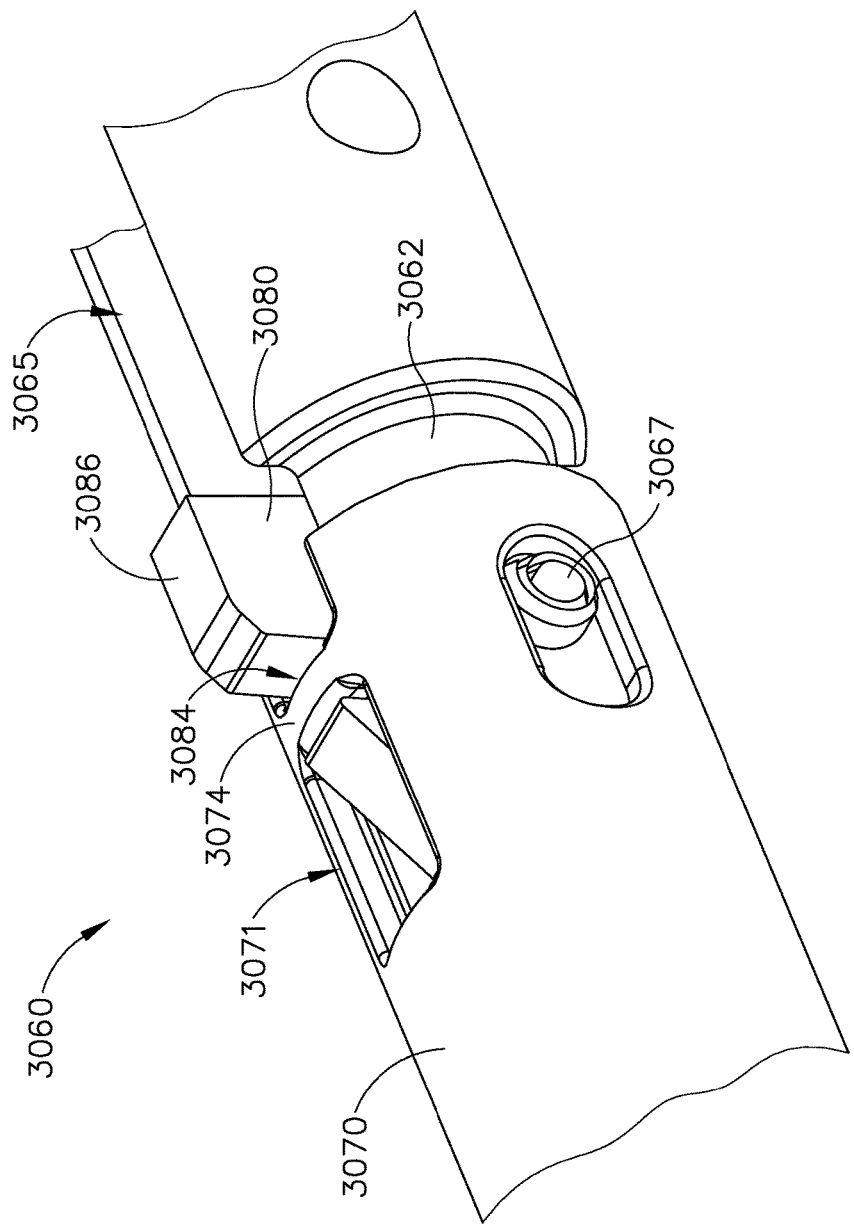
FIG. 29A depicts a detailed perspective view of the trocar of FIG. 26, with a sleeve member of the trocar in a first position, and with a lockout member in a first rotational position.
Figure 29B:
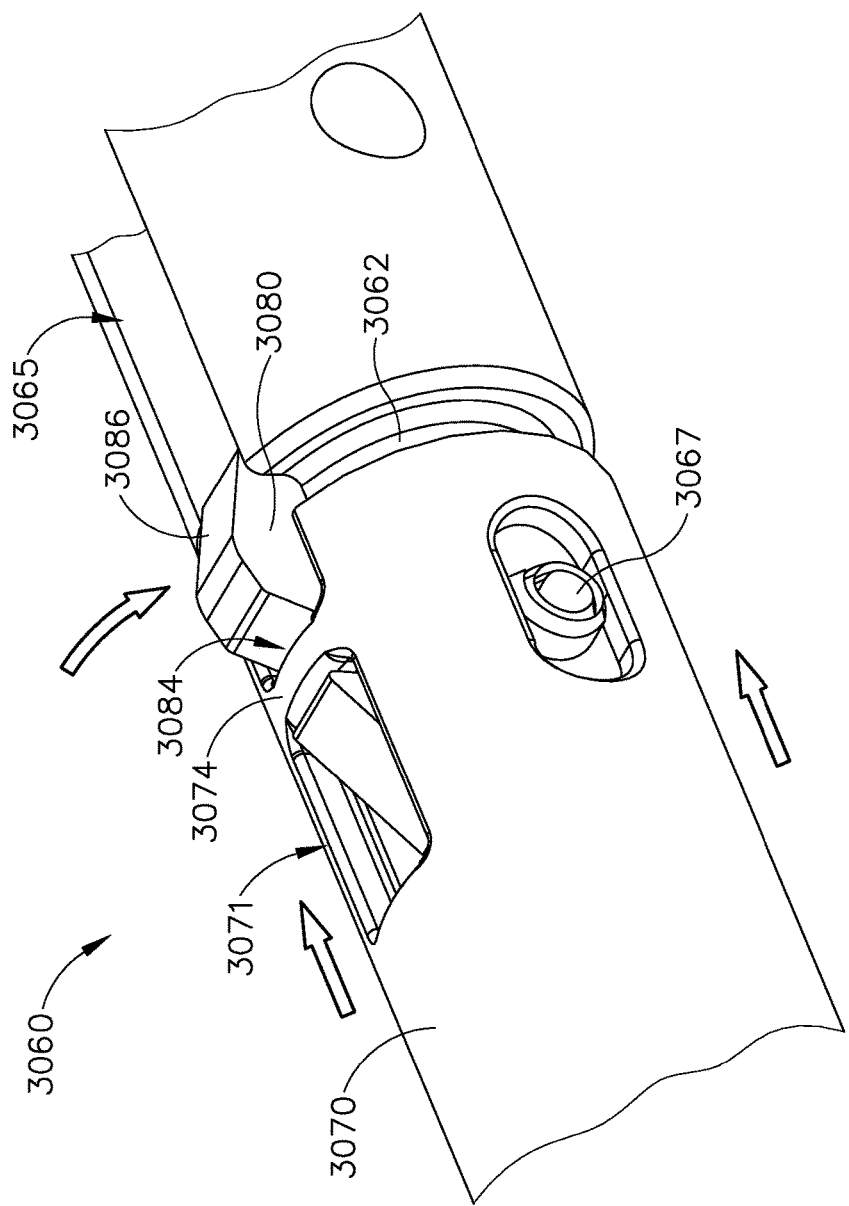
FIG. 29B depicts a detailed perspective view of the trocar of FIG. 26, with the sleeve member of FIG. 29A moved to a second position, and with the lockout member of FIG. 29A moved to a second rotational position by movement of the sleeve member to the second position.
Figure 29C:
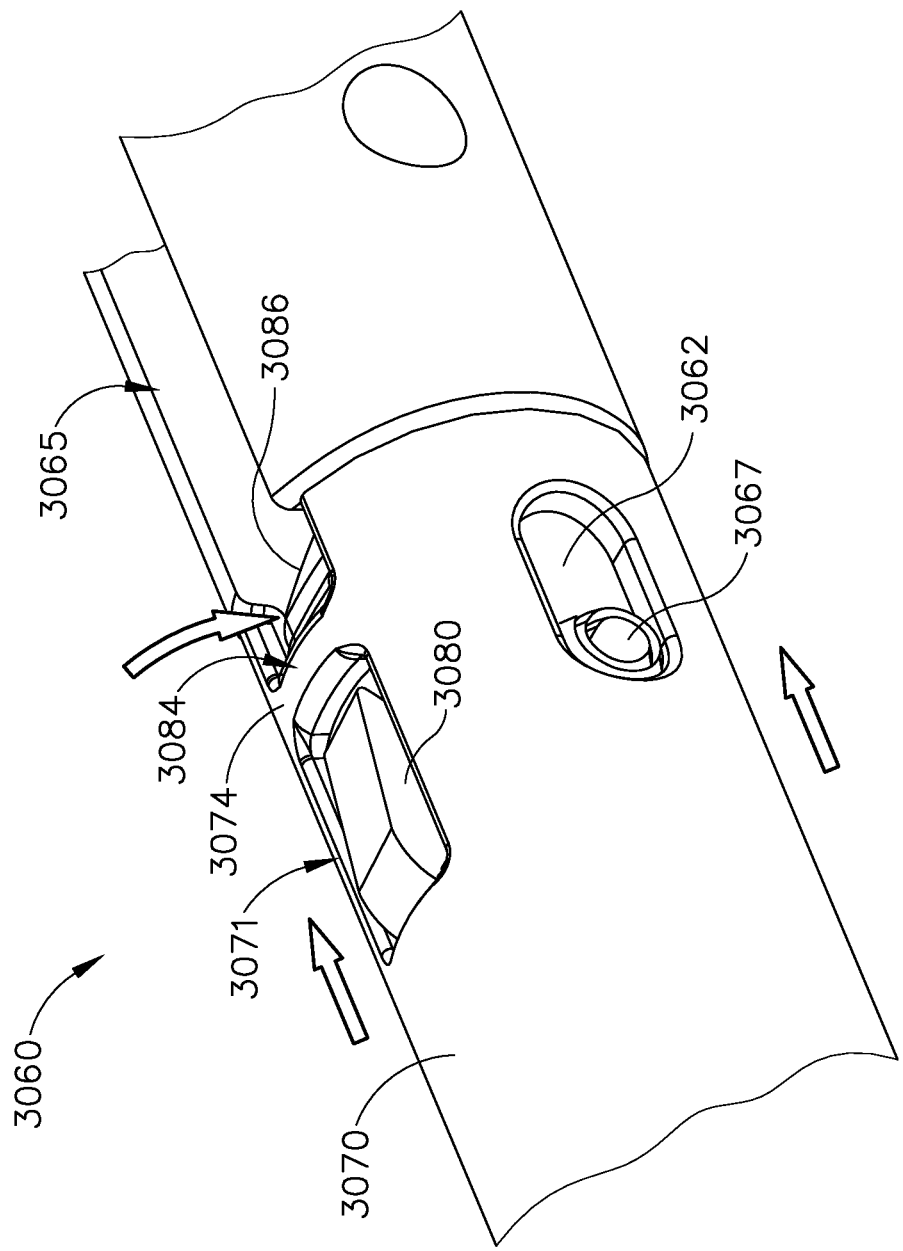
FIG. 29C depicts a detailed perspective view of the trocar of FIG. 26, with the sleeve member of FIG. 29A moved to a third position, and with the lockout member of FIG. 29A moved to a third rotational position by movement of the sleeve member to the third position.
Figure 31A:
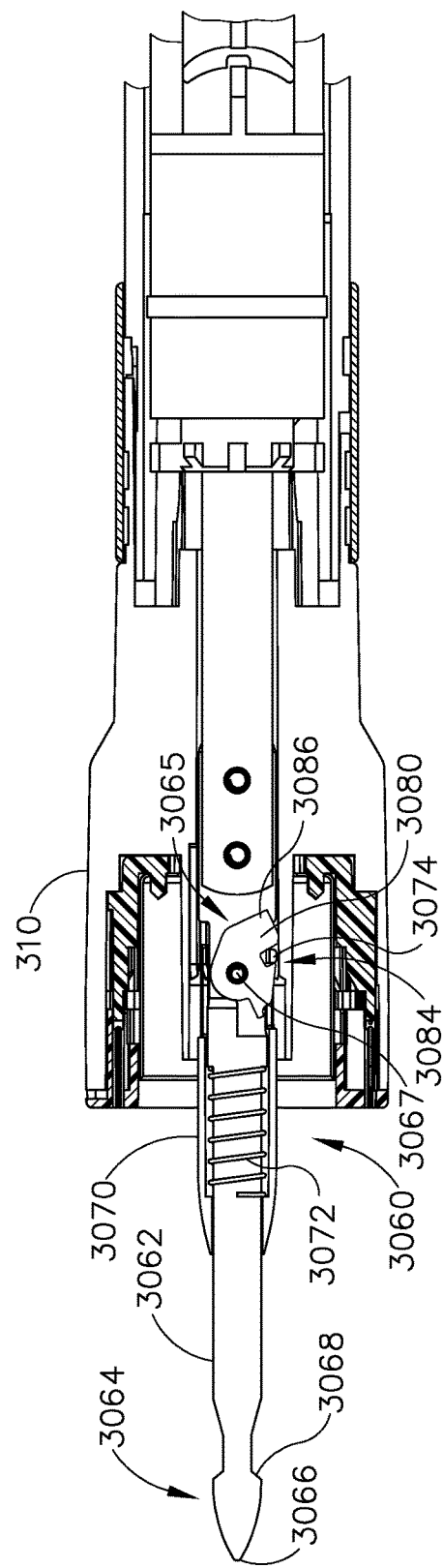
FIG. 31A depicts a cross-sectional side view of the distal end of yet another exemplary alternative circular stapler incorporating the trocar of FIG. 26, with the trocar of FIG.
Figure 31B:
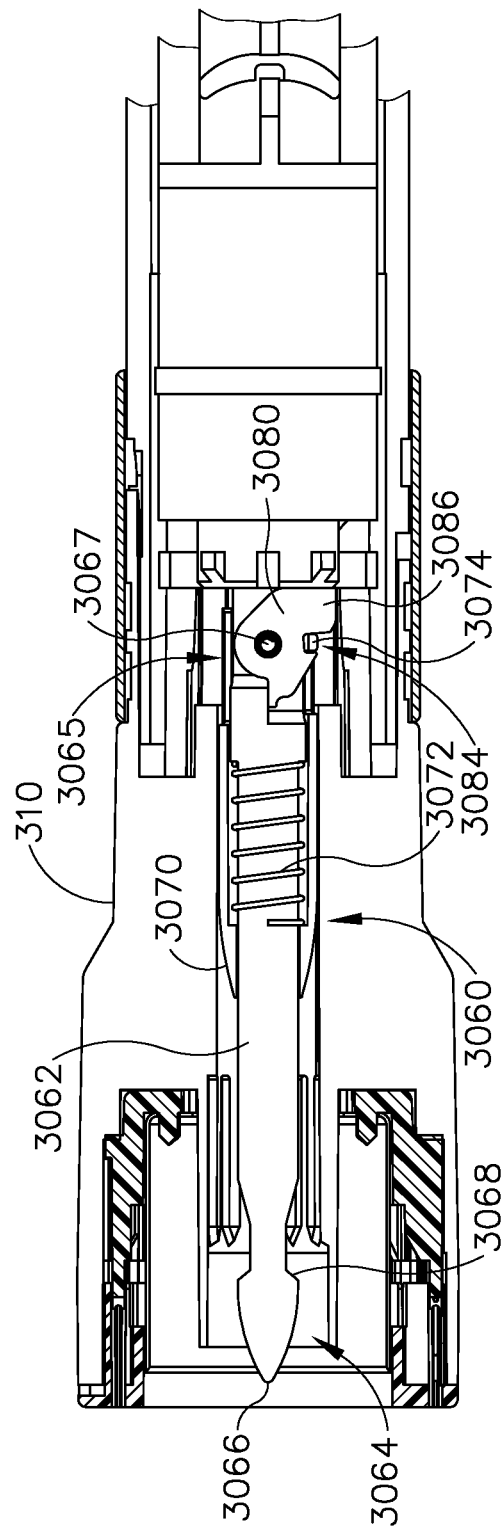
Figure 32B:
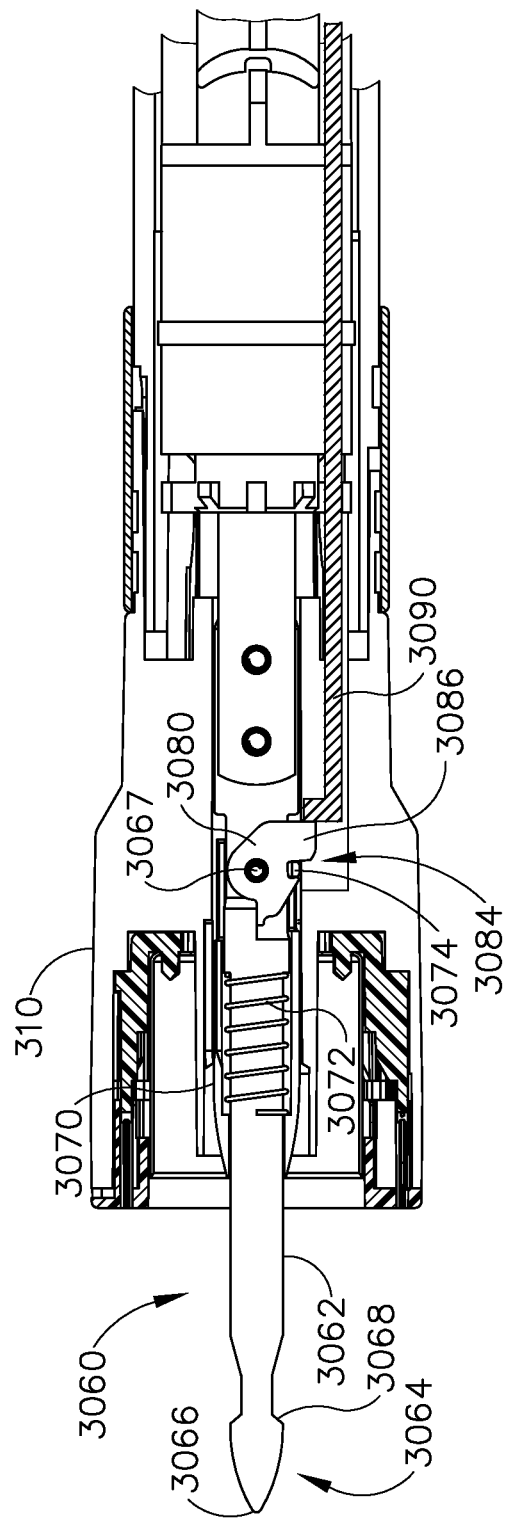
Figure 32C:
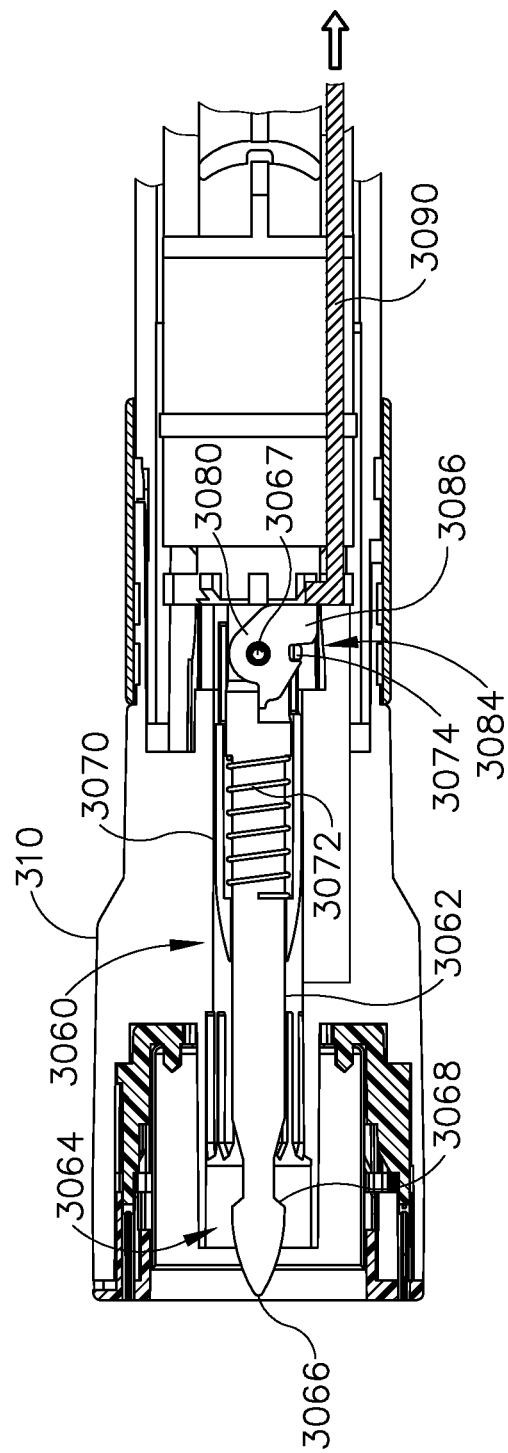
Figure 33A:
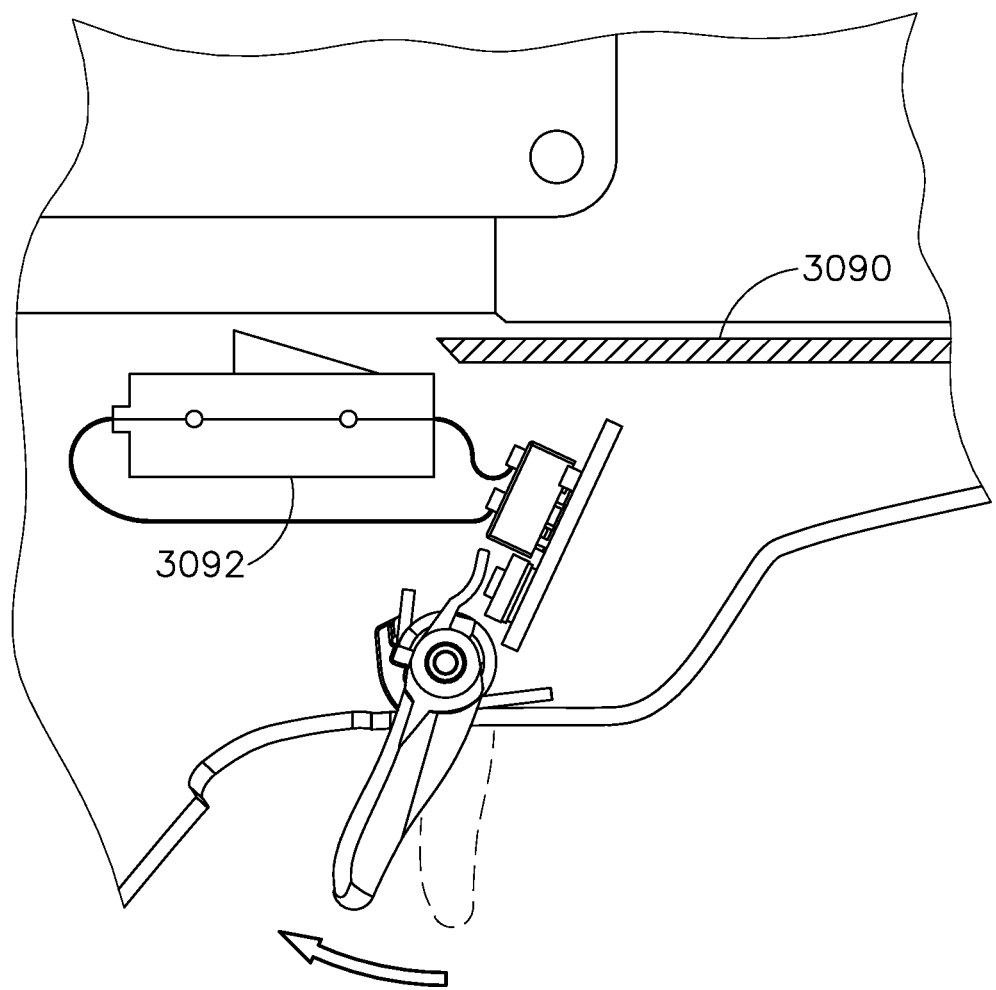
Figure 33B:
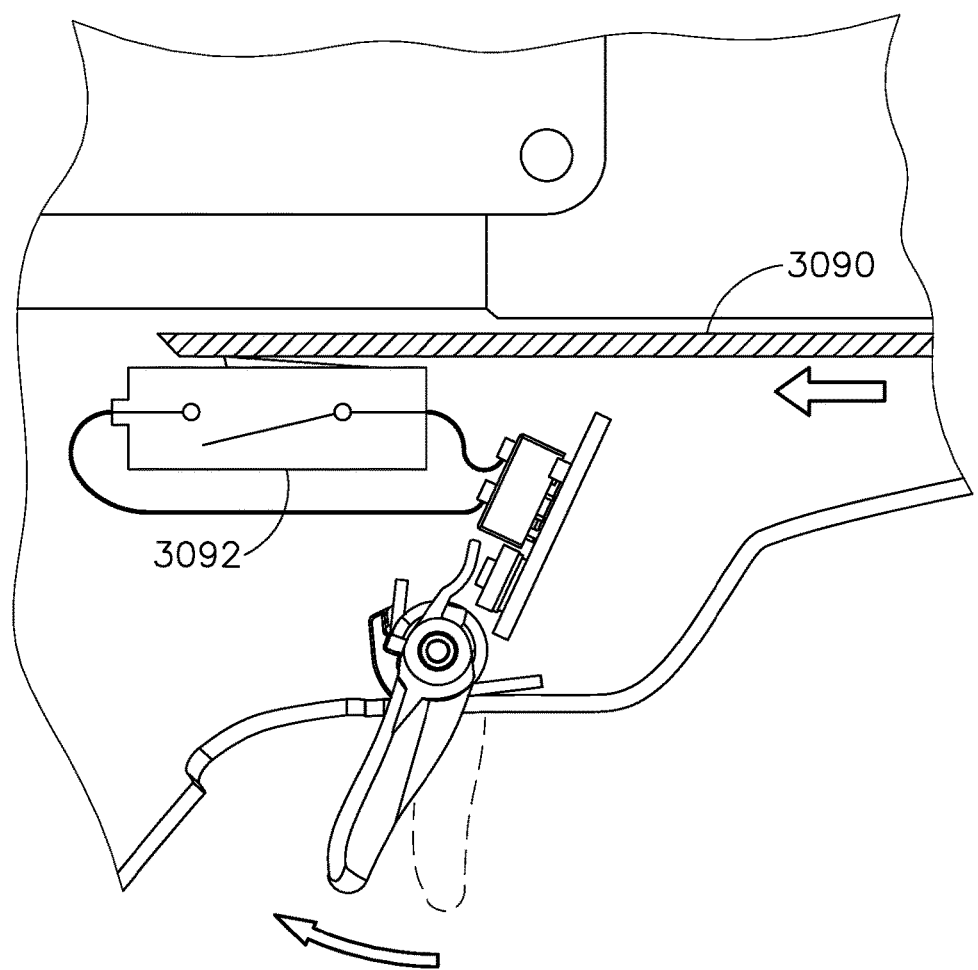
Figure 34A:
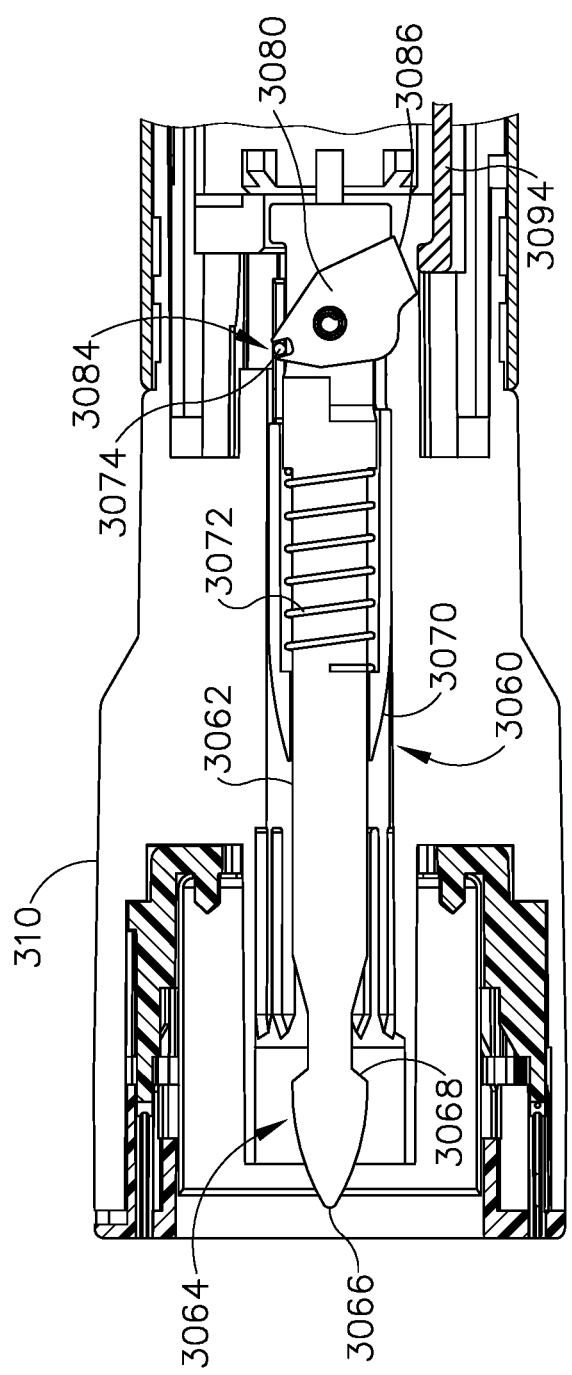
Figure 34B:
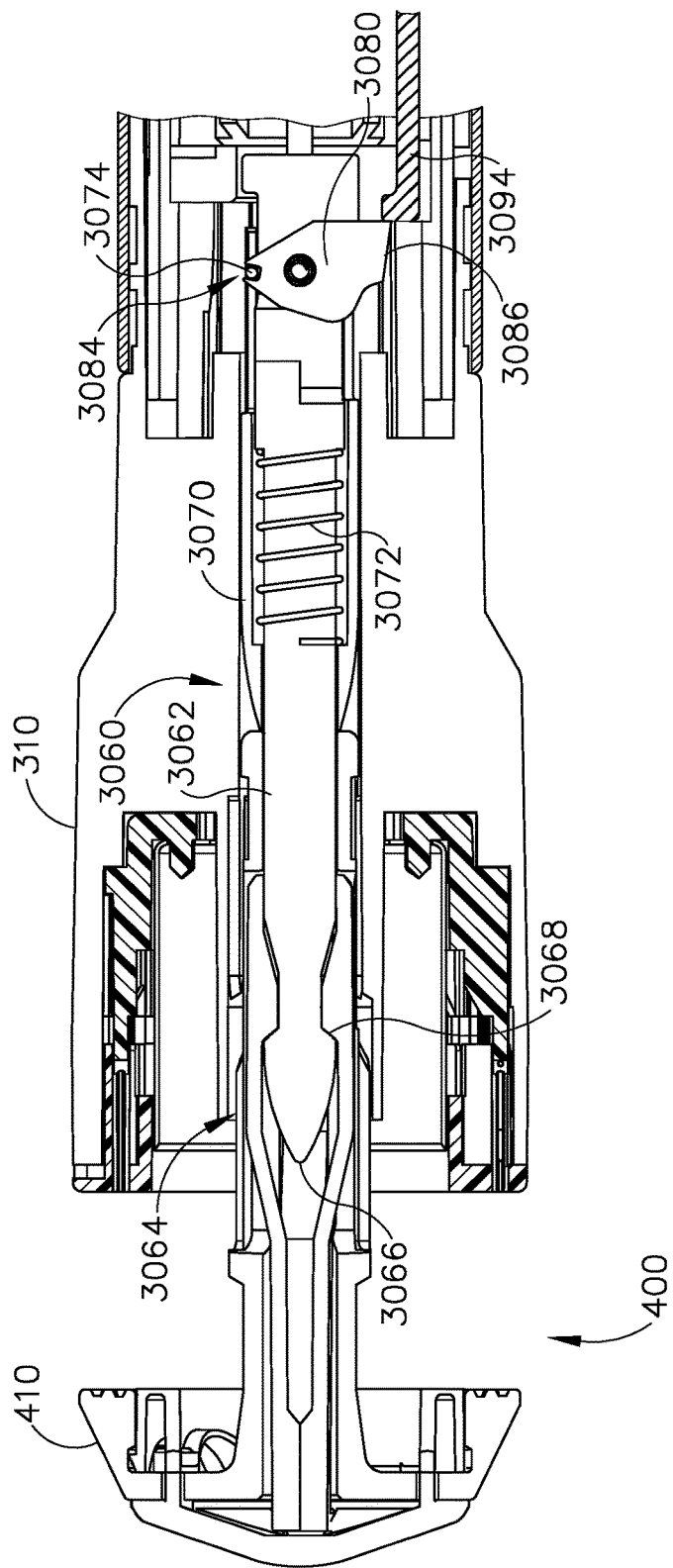
Figure 35A:
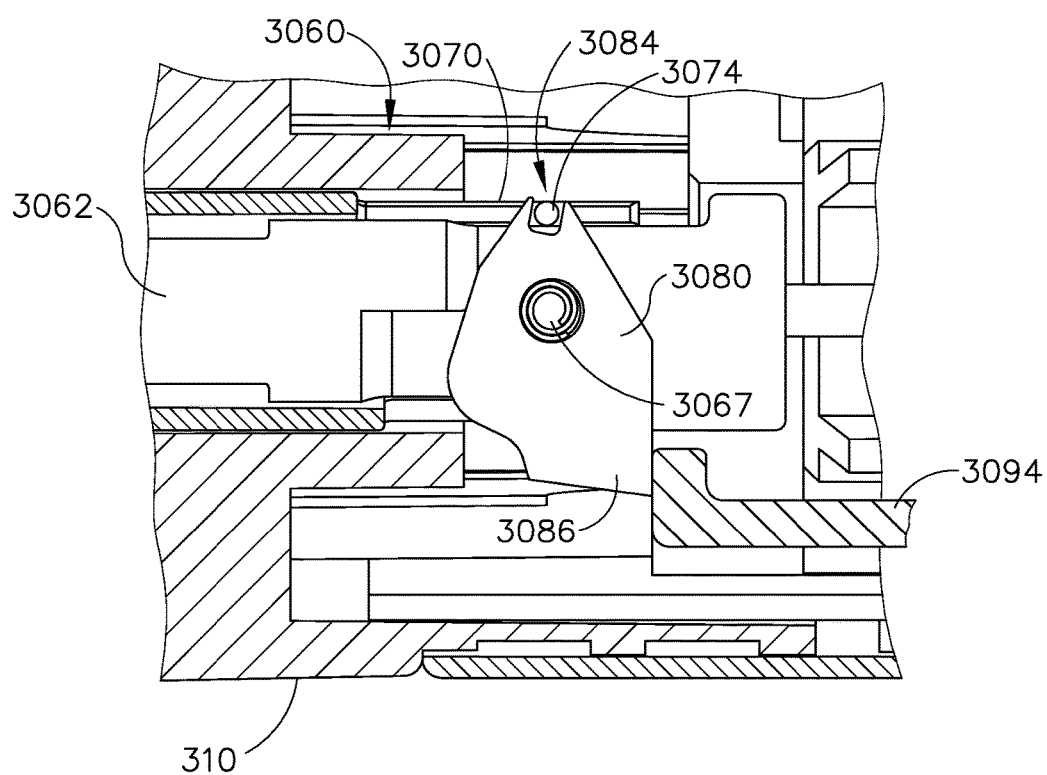
Figure 35B:
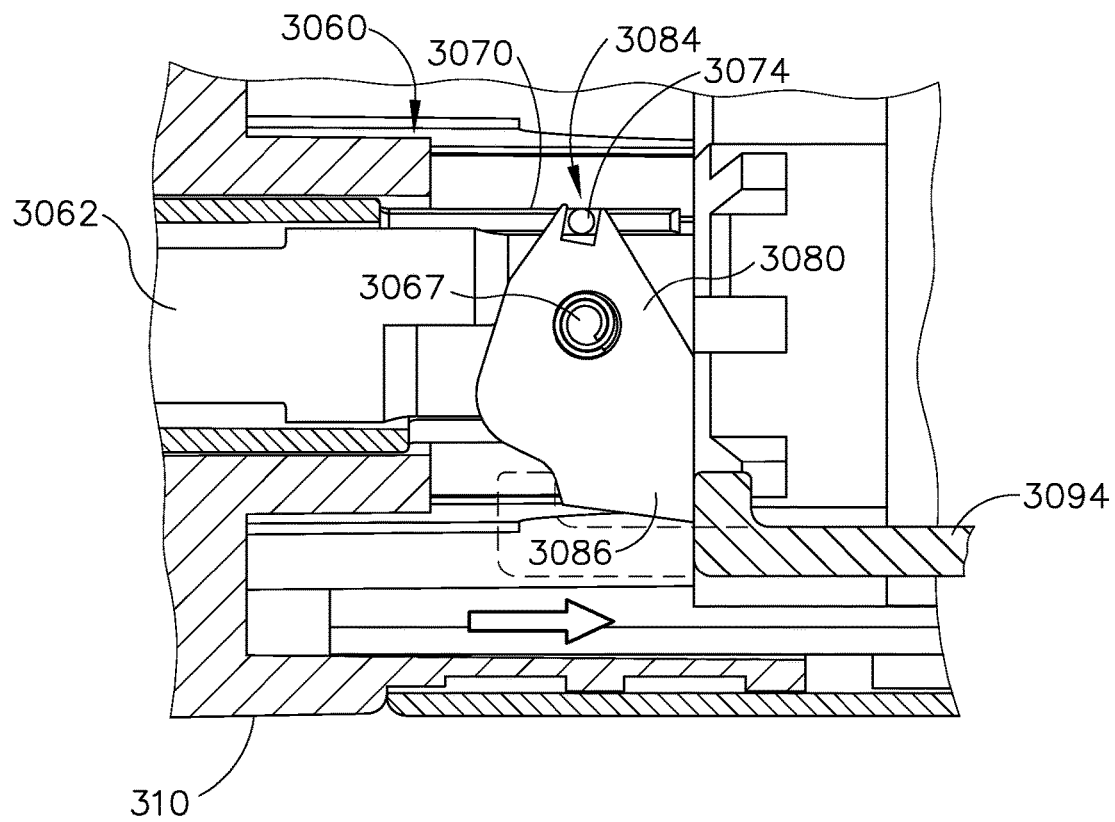
Figure 36A:
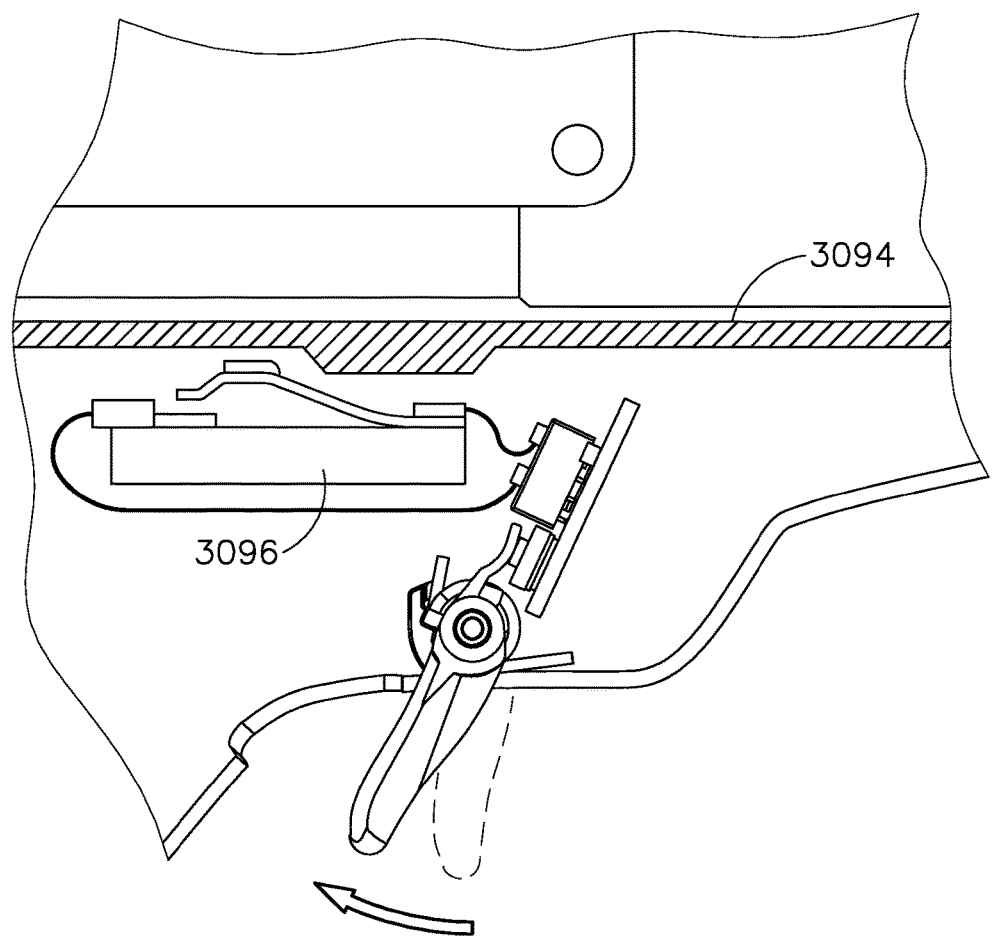
Figure 36B:
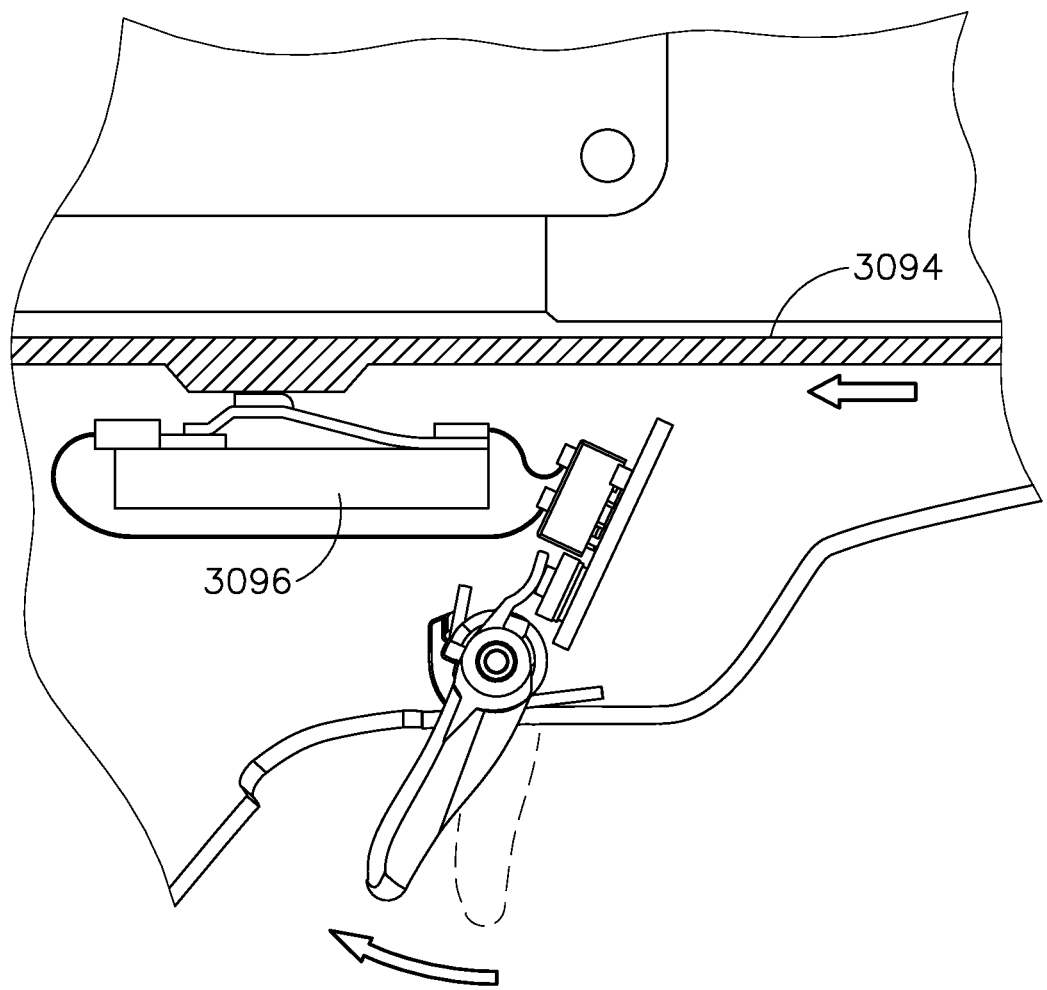
Figure 37A:
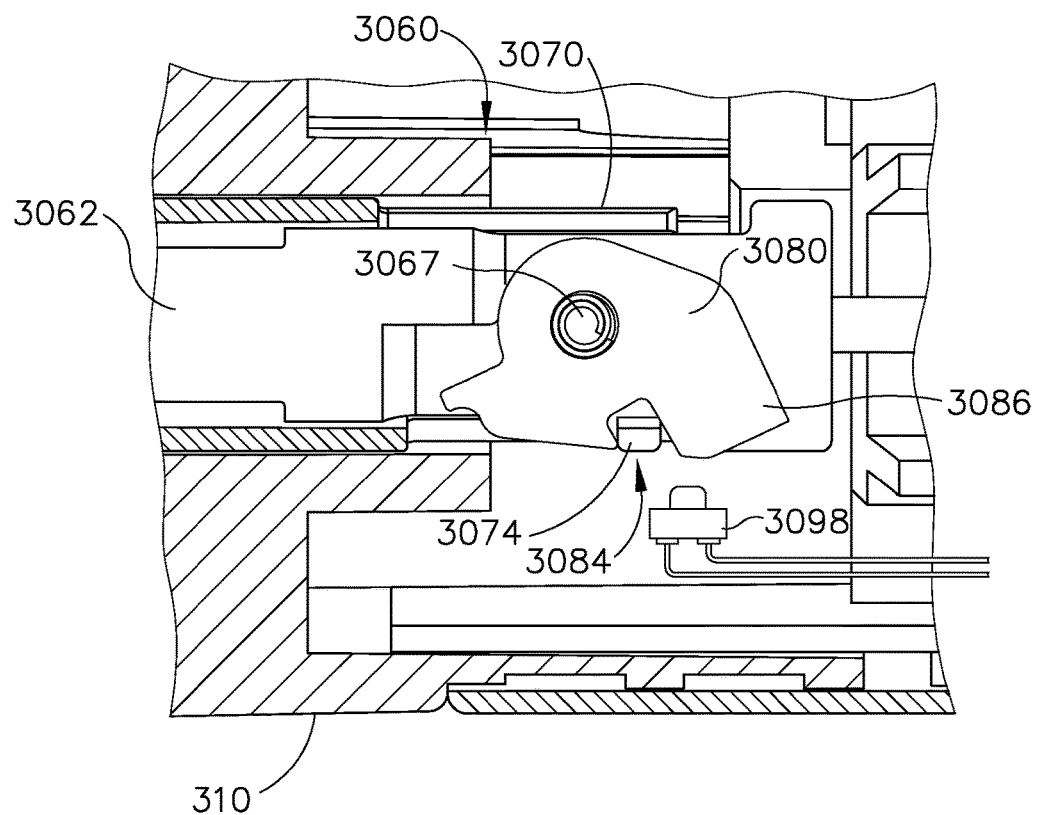
Figure 37B:
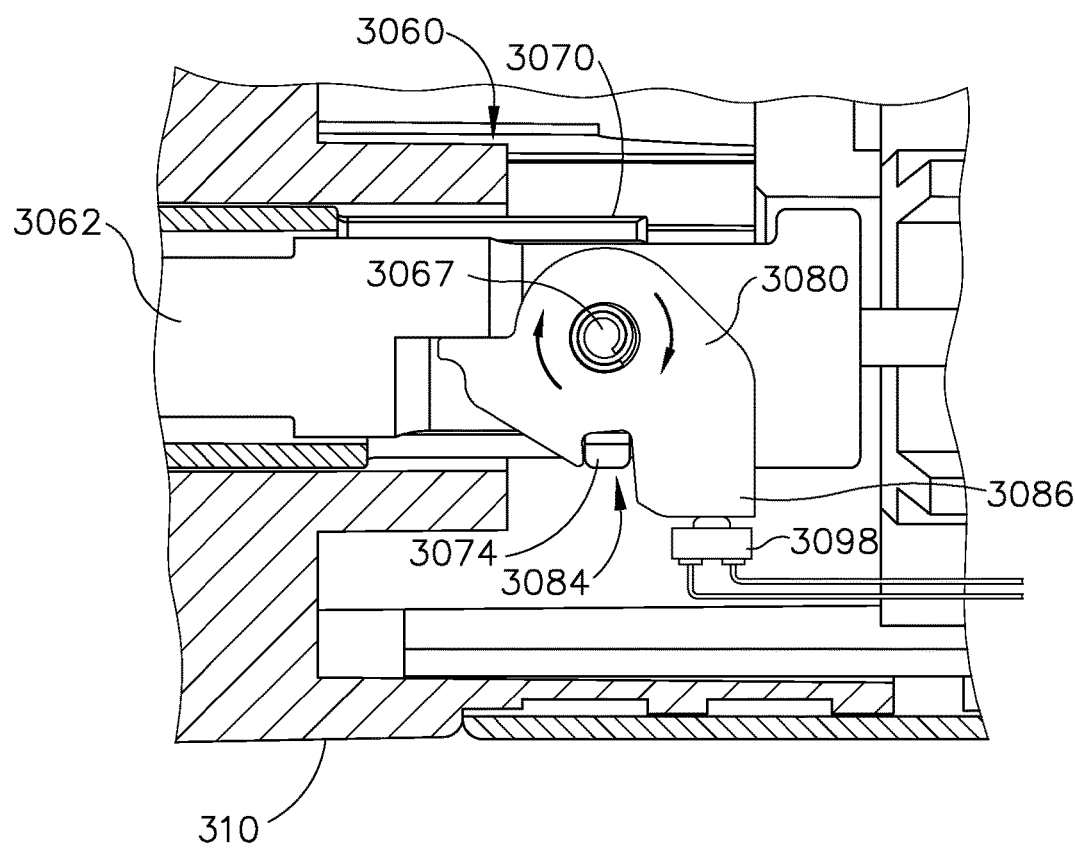
Figure 38:
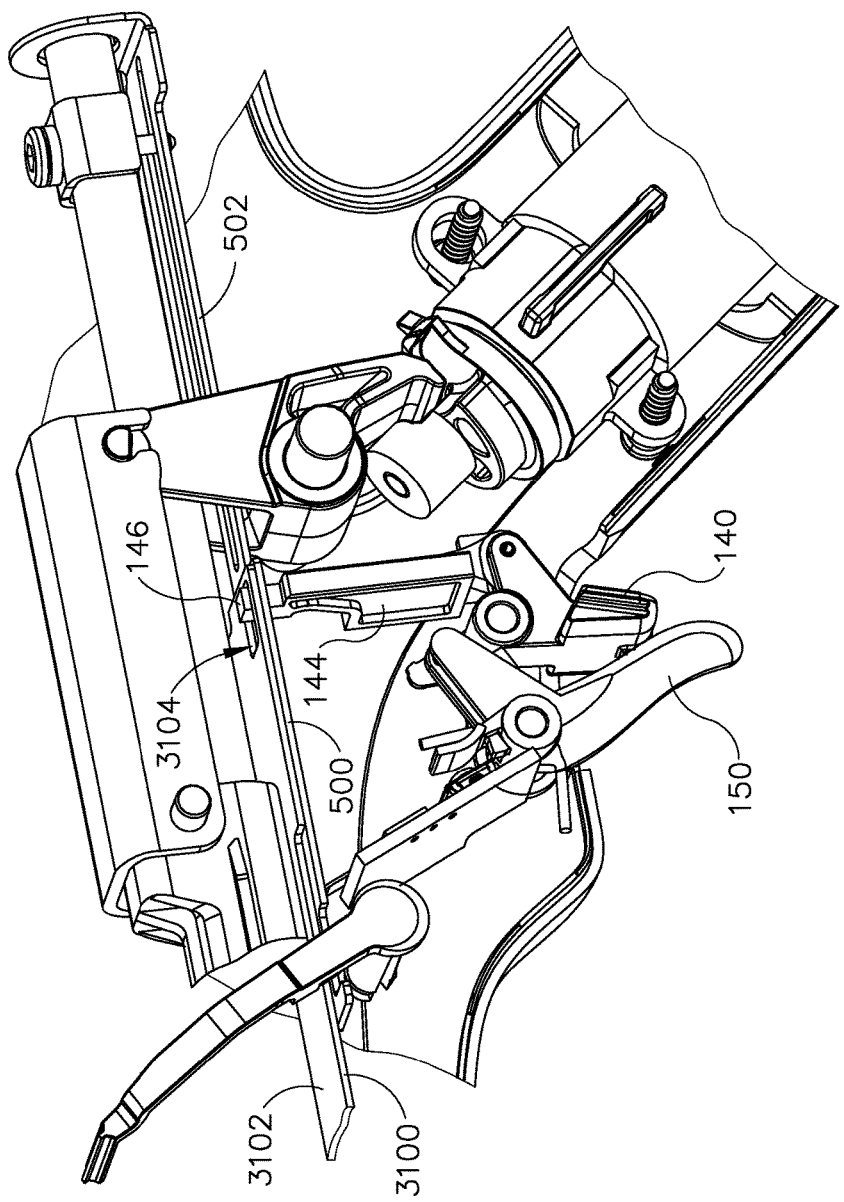
Figure 39A:
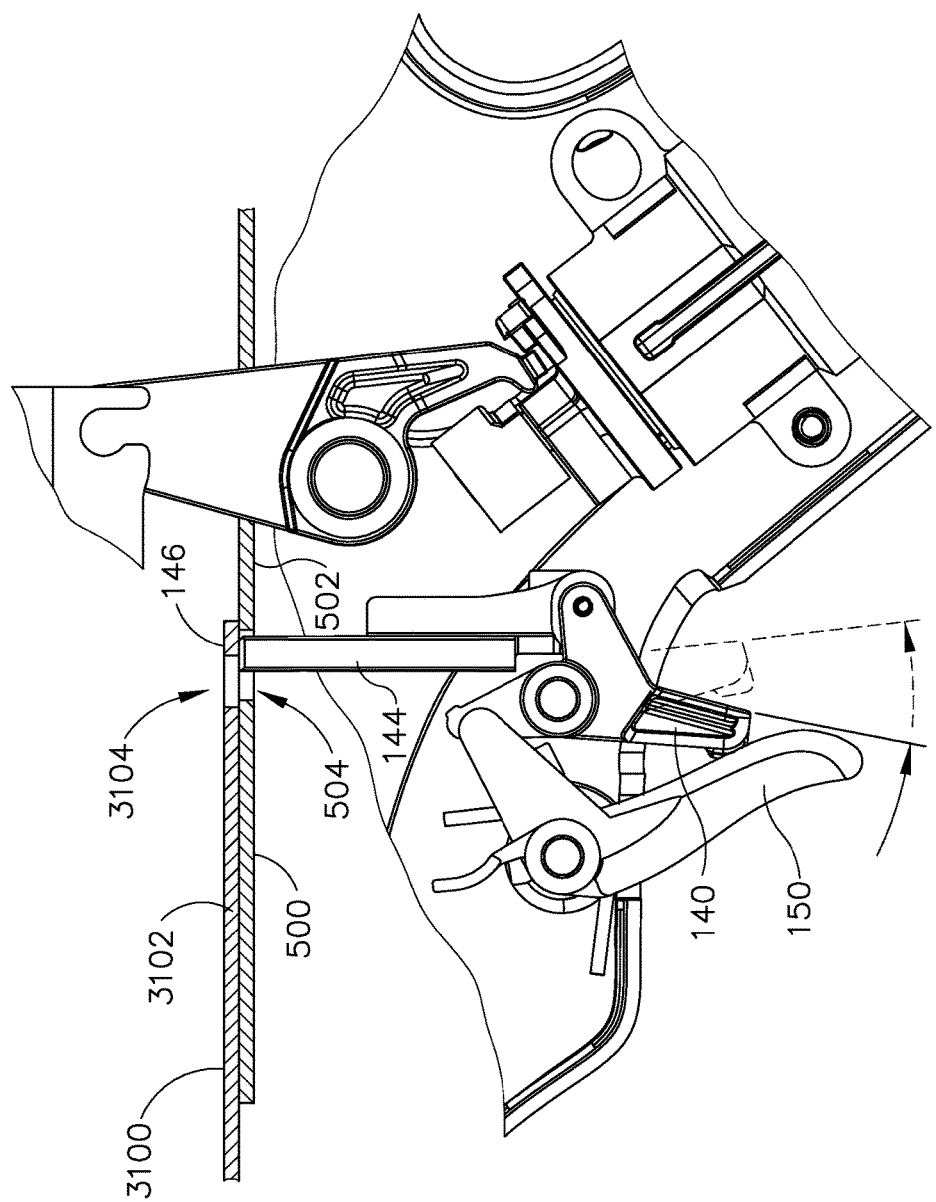
Figure 39B:
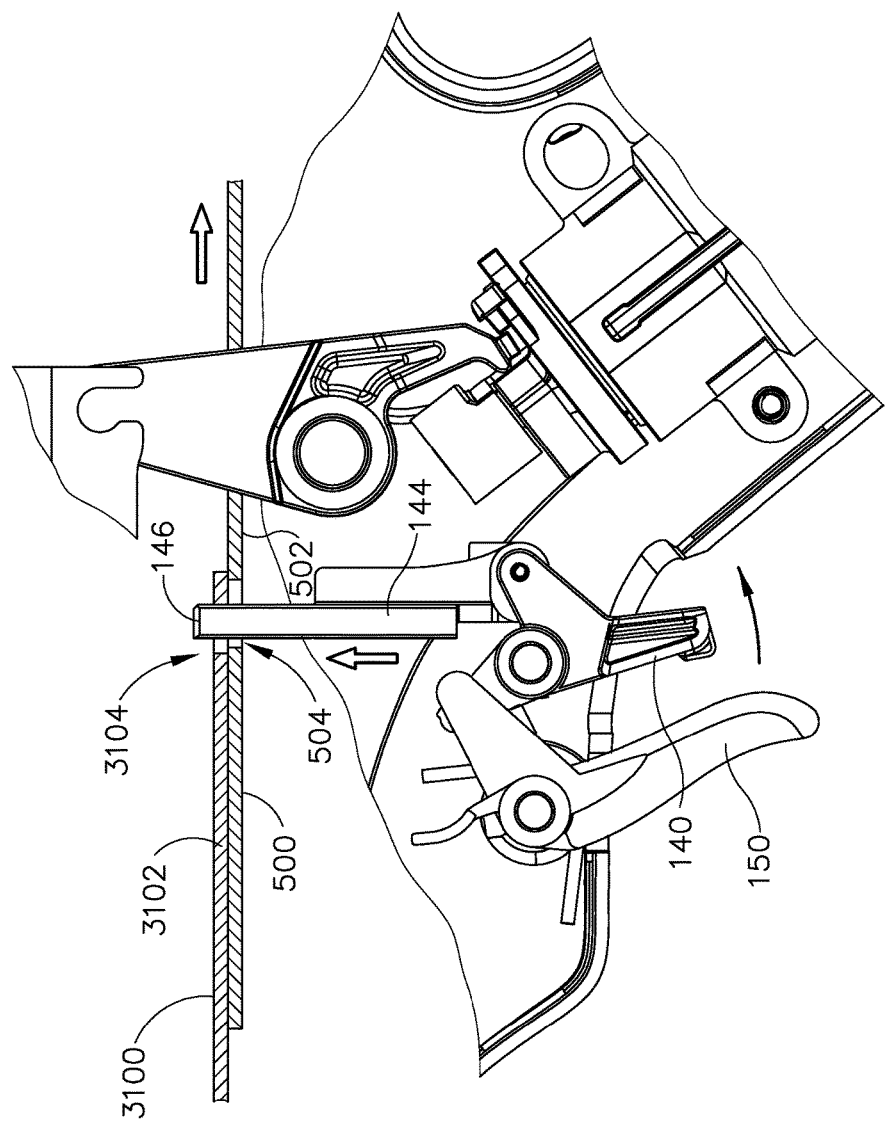
Figure 40:
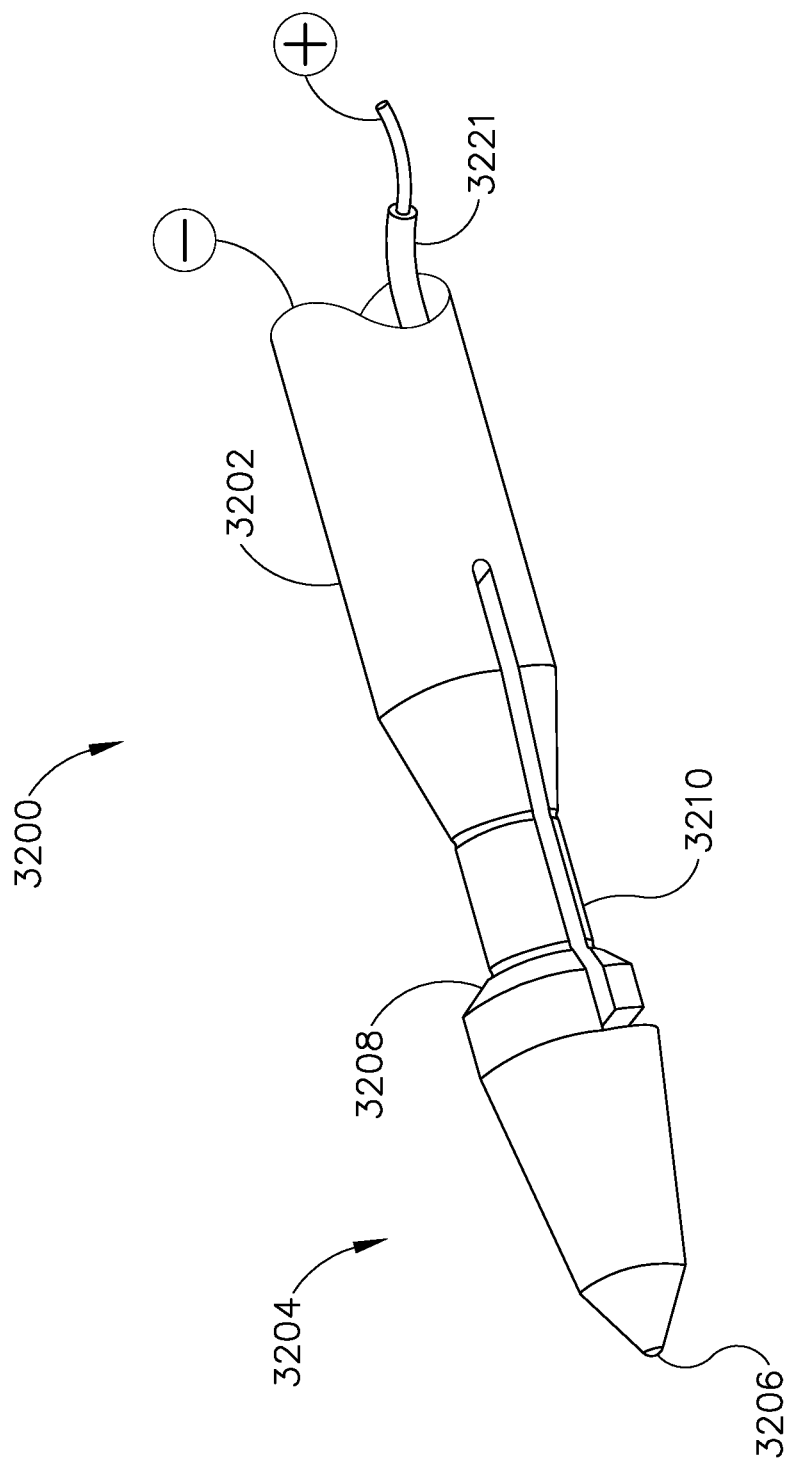
Figure 41A:
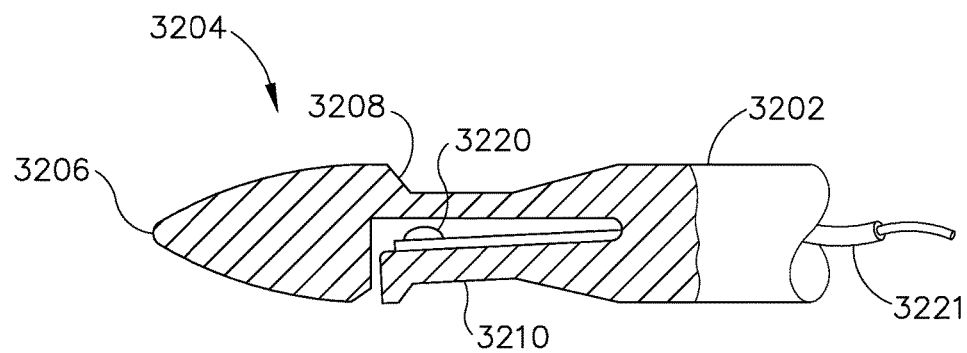
Figure 41B:
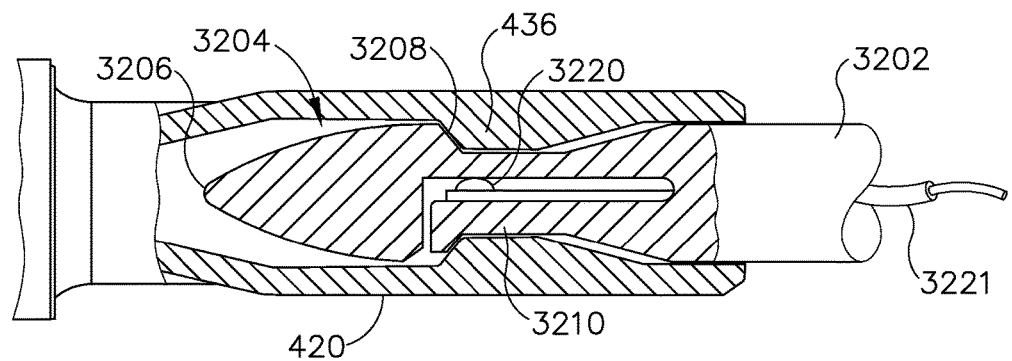
Figure 42:
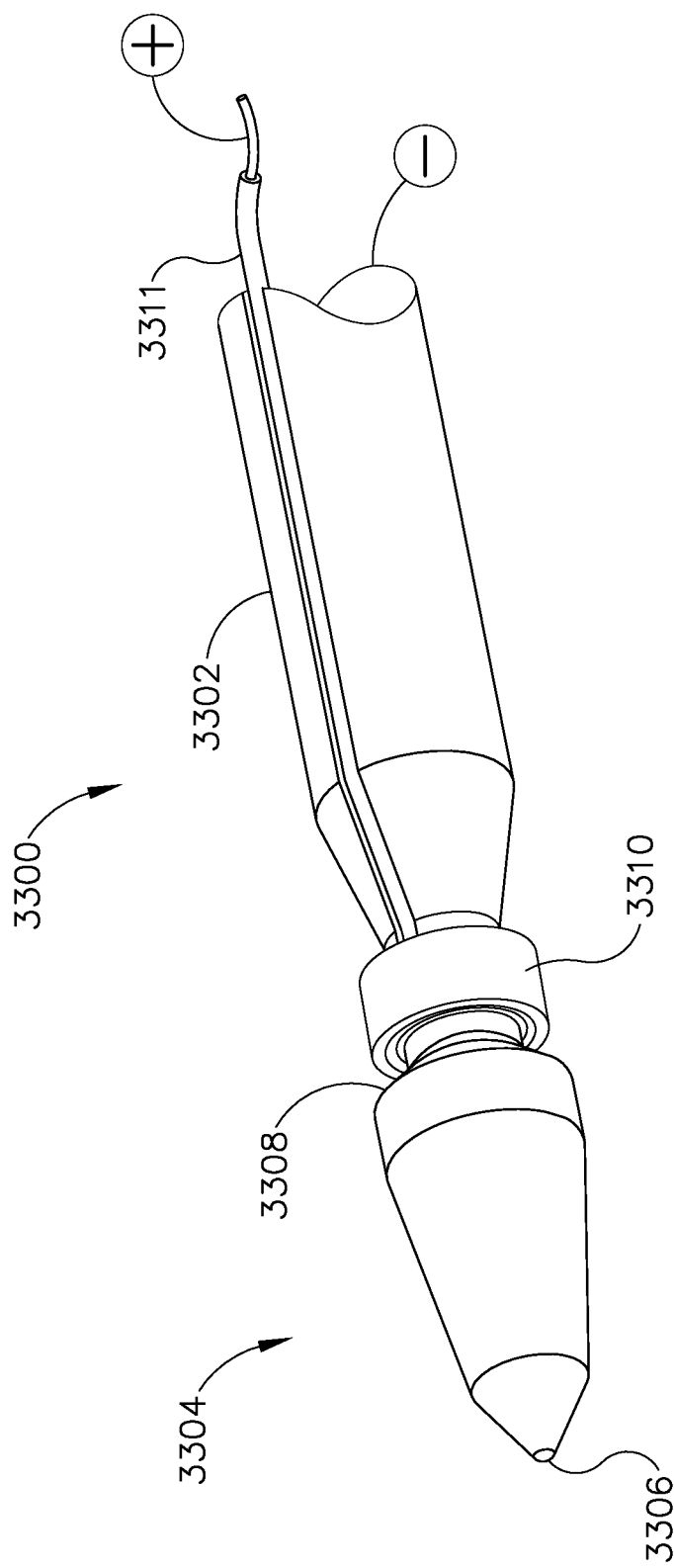
Figure 43A:
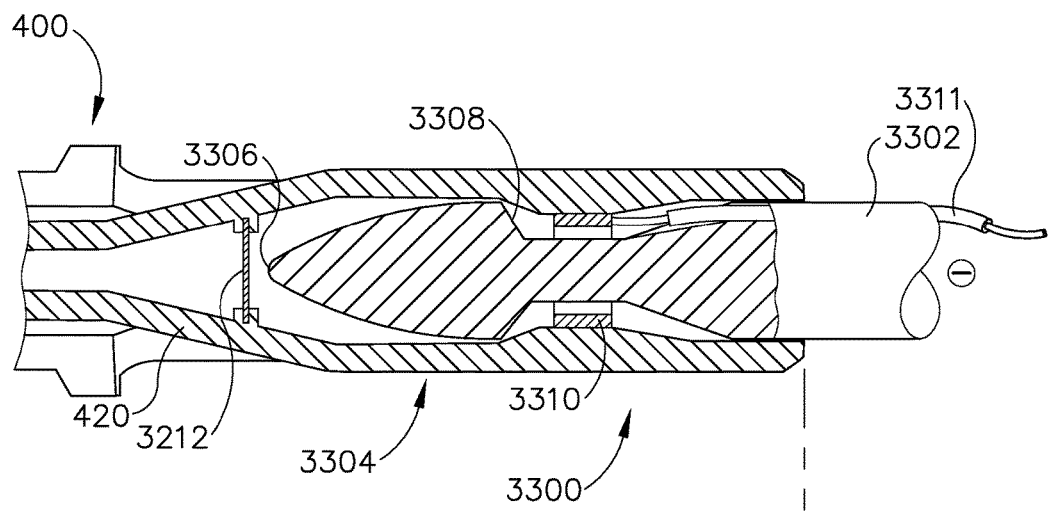
Figure 43B:
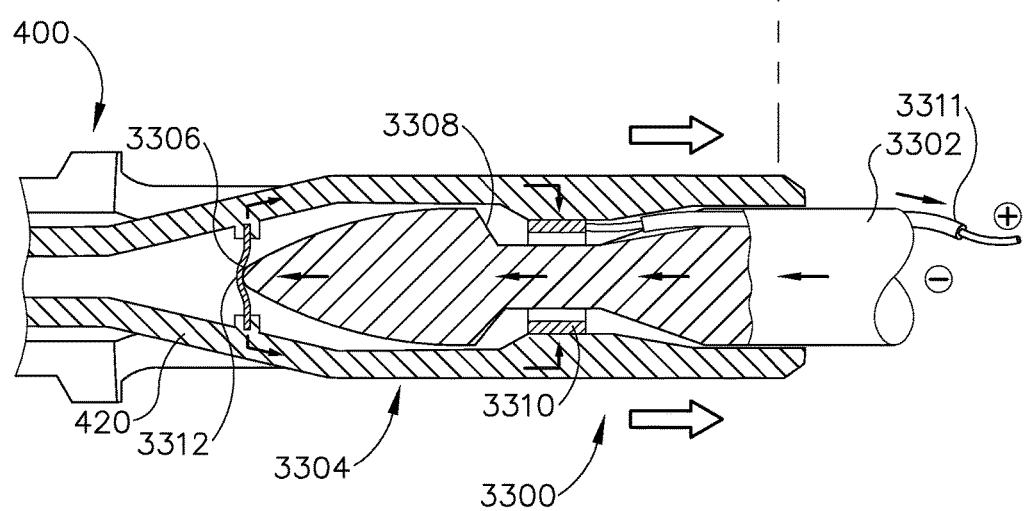
Figure 44:
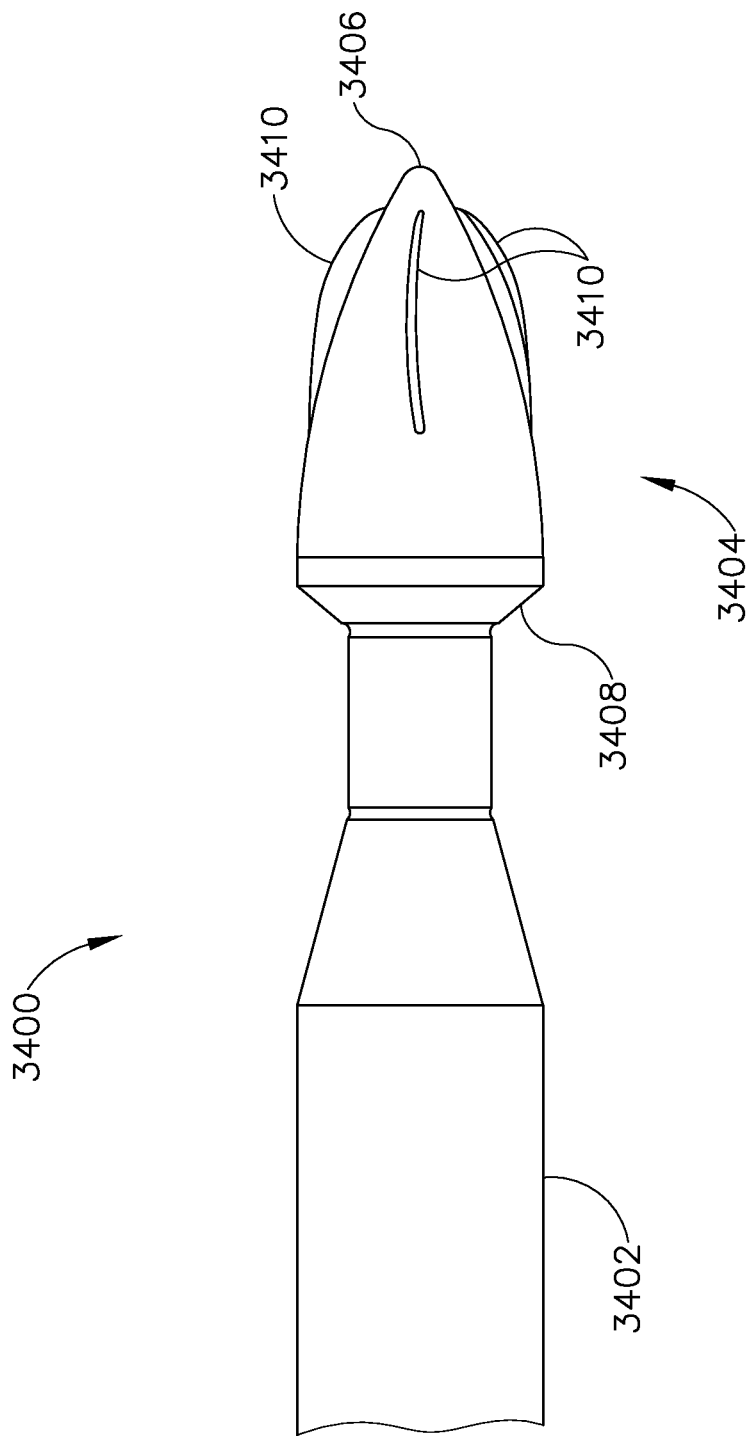
Figure 45A:
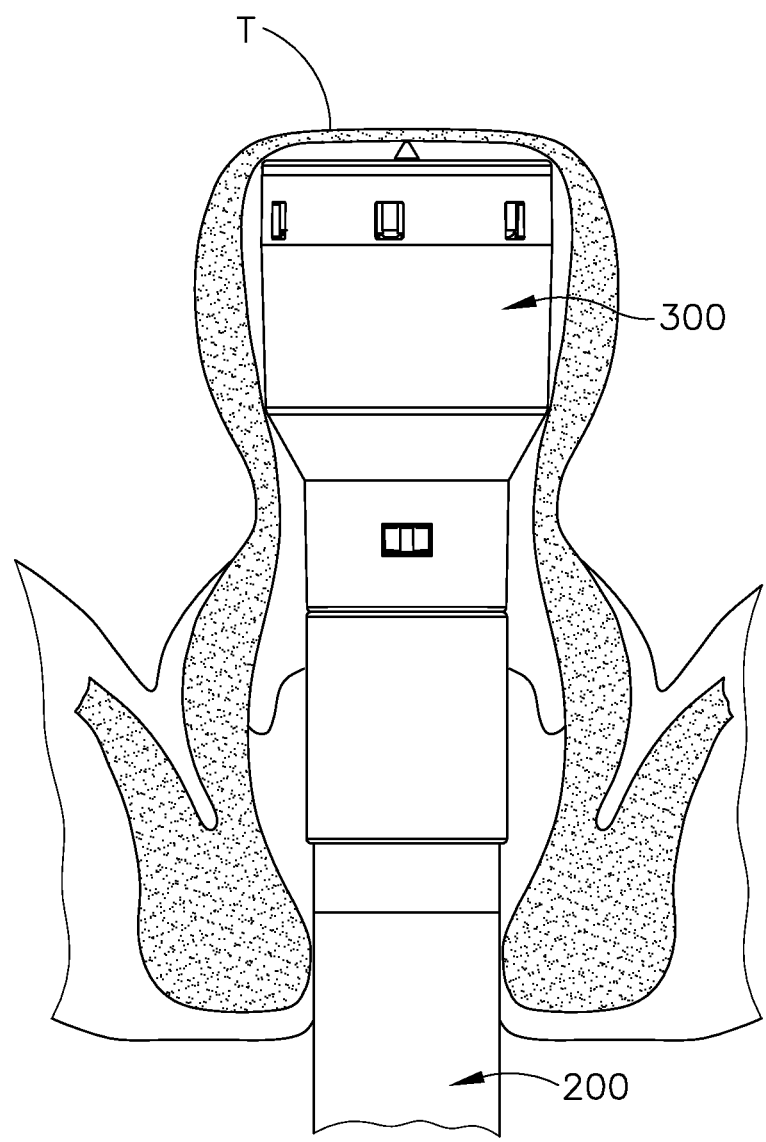
Figure 45B:
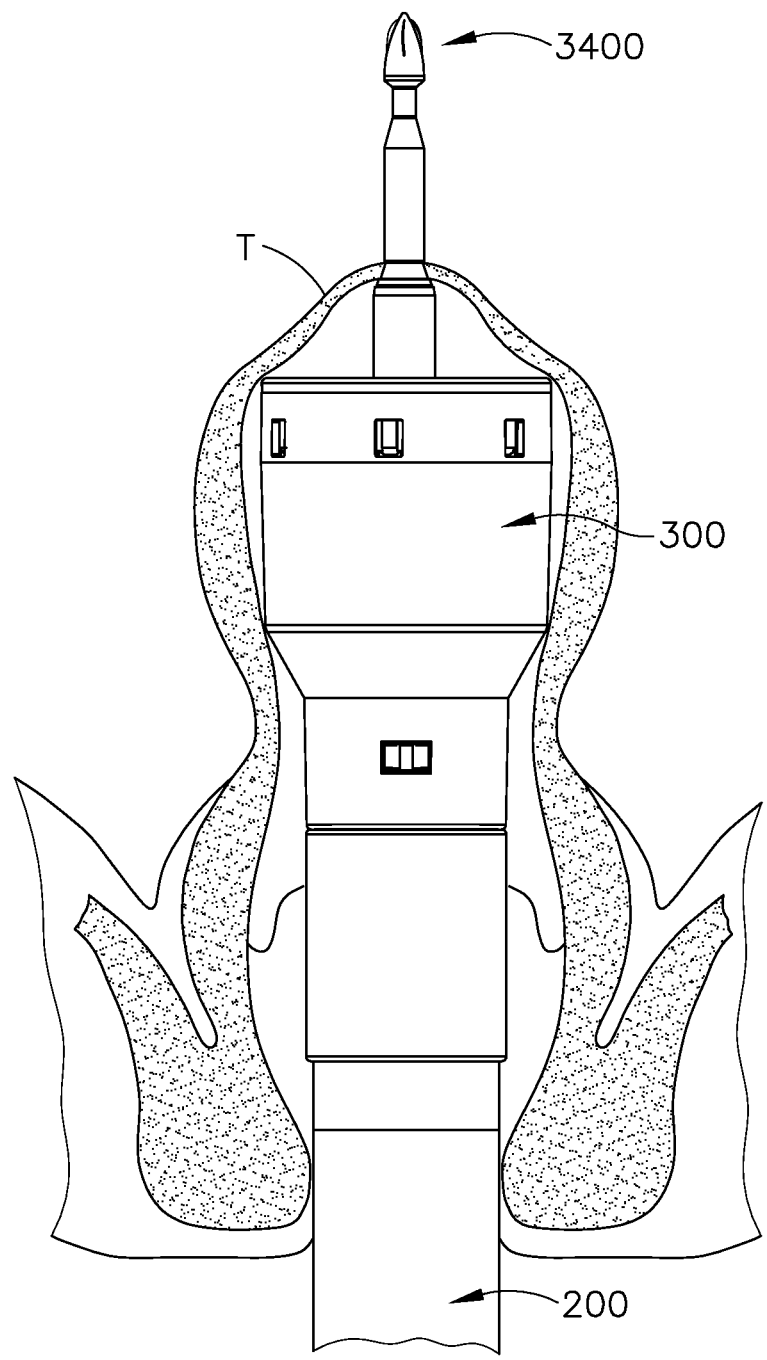

26 in a first position, with the sleeve member of FIG. 29A in the first position of FIG. 29A, and with the lockout of FIG. 29A in the third rotational position of FIG. 29C;

FIG. 31B depicts a cross-sectional side view of the distal end of the circular stapler of FIG. 31A, with the trocar of FIG. 26 moved to a second position, with the sleeve member of FIG. 29A in the first position of FIG. 29A, and with the lockout member of FIG. 29A moved to the first rotational position of FIG. 29A;

FIG. 31C depicts a cross-sectional side view of the distal end of the circular stapler of FIG. 31A, with the trocar of FIG. 26 moved to a third position, with the sleeve member of FIG. 29A moved to the third position of FIG. 29C, and with the lockout tab of FIG. 29A in the third rotational position;

FIG. 32A depicts a cross-sectional side view of the distal end of yet another exemplary alternative circular stapler, with a trocar of the circular stapler in a first position, with a lockout member in a first rotational position, and with a link member in a first position;

FIG. 32B depicts a cross-sectional side view of the distal end of the circular stapler of FIG. 32A, with the trocar of FIG. 32A moved to a second position, with the lockout member of FIG. 32A moved to a second rotational position so as to engage the link member of FIG. 32A, and with the link member remaining in the first position;

FIG. 32C depicts a cross-sectional side view of the distal end of the circular stapler of FIG. 32A, with the trocar of FIG. 32A moved to a third position, with the lockout member of FIG. 32A remaining in the second rotational position, and with the link member of FIG. 32A moved to a second position;

FIG. 32D depicts a cross-sectional side view of the distal end of the circular stapler of FIG. 32A, with the trocar of FIG. 32A in the third position of FIG. 32C, with the lockout member of FIG. 32A remaining in the first rotational position of FIG. 32A, and with the link member of FIG. 32A remaining in the first position of FIG. 32A;

FIG. 33A depicts a cross-sectional side view of a contact switch of the circular stapler of FIG. 32A, with the contact switch in a closed state, and with the link member of FIG. 32A in the first position of FIG. 32A;

FIG. 33B depicts a cross-sectional side view of the contact switch of FIG. 33A, with the contact switch moved to an open position by movement of the link member of FIG. 32A to the second position of FIG. 32C;

FIG. 34A depicts a cross-sectional side view of the distal end of yet another exemplary alternative circular stapler, with a lockout member in a first rotational position;

FIG. 34B depicts a cross-sectional side view of the distal end of the circular stapler of FIG. 34A, with the lockout member of FIG. 34A moved to a second rotational position so as to engage a link member of the circular stapler;

FIG. 35A depicts a detailed cross-sectional side view of the distal end of the circular stapler of FIG. 34A, with the lockout member of FIG. 34A in the second rotational position of FIG. 34B so as to engage the link member of FIG. 34B, and with a trocar of the circular stapler in a distal longitudinal position;

FIG. 35B depicts a detailed cross-sectional side view of the distal end of the circular stapler of FIG. 34A, with the lockout member of FIG. 34A in the second rotational position of FIG. 34B so as to engage the link member of FIG. 34B, and with the link member moved to a proximal longitudinal position by movement of the trocar to a proximal longitudinal position;

FIG. 36A depicts a cross-sectional side view of a contact switch of the circular stapler of FIG. 34A, with the contact switch in an open state, and with the link member of FIG. 34B in the first position of FIG. 35A;

FIG. 36B depicts a cross-sectional side view of the contact switch of FIG. 36A, with the contact switch moved to a closed state by movement of the link member of FIG. 34B to the second position of FIG. 35B;

FIG. 37A depicts a cross-sectional side view of the distal end of yet another exemplary alternative circular stapler, with a lockout member in a first rotational position, and with a contact switch in an open state;

FIG. 37B depicts a cross-sectional side view of the distal end of the circular stapler of FIG. 37A, with the lockout tab of FIG. 37A rotated to a second rotational position so as to close the contact switch of FIG. 37A;

FIG. 38 depicts a perspective view of components of yet another exemplary alternative circular stapler;

FIG. 39A depicts an enlarged side view of an anvil actuation assembly of the circular stapler of FIG. 38, with an actuation rod in a first position, and with a lockout rod in a first position;

FIG. 39B depicts a side view of the anvil actuation assembly of FIG. 39A, with the actuation rod moved to a second position, and with the lockout rod moved to a second position;

FIG. 40 depicts a perspective view of the distal end of an exemplary alternative trocar;

FIG. 41A depicts a cross-sectional side view of the distal end of the trocar of FIG. 40, with a contact switch of the trocar in an open state;

FIG. 41B depicts a cross-sectional side view of the distal end of the trocar of FIG. 40, with the contact switch of FIG. 41A moved to a closed state;

FIG. 42 depicts a perspective view of the distal end of another exemplary alternative trocar;

FIG. 43A depicts a cross-sectional side view of the distal end of the trocar of FIG. 42, with a circuit of the trocar in an open state;

FIG. 43B depicts a cross-sectional side view of the distal end of the trocar of FIG. 42, with the circuit of FIG. 43A in a closed state;

FIG. 44 depicts a side view of the distal end of yet another exemplary alternative trocar;

FIG. 45A depicts a side view of the trocar of FIG. 44, with the trocar in a first position; and FIG. 45B depicts a side view of the trocar of FIG. 44, with the trocar moved to a second position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 1:
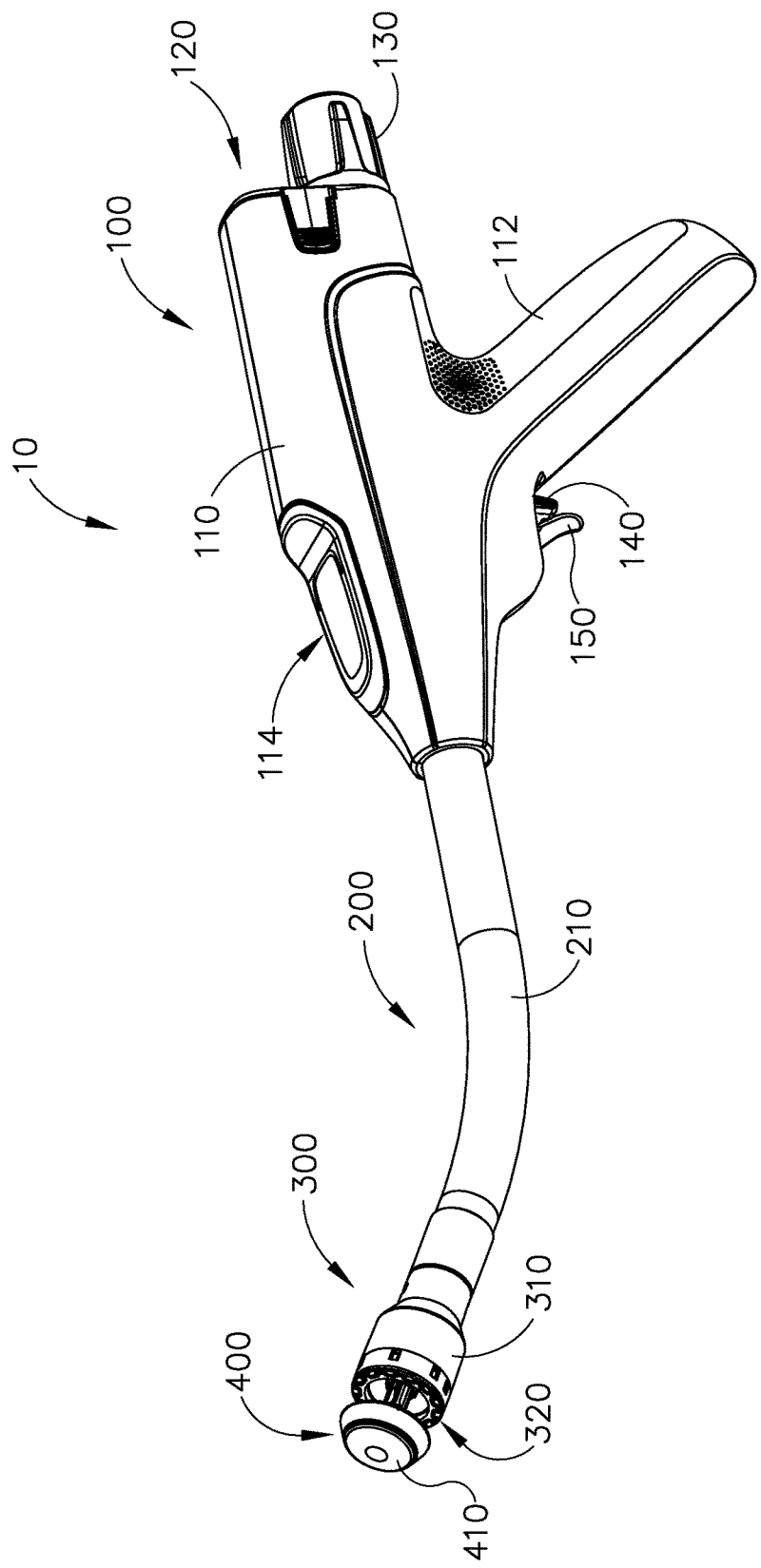
FIG. 1 depicts a perspective view of an exemplary circular stapler.
Figure 2:
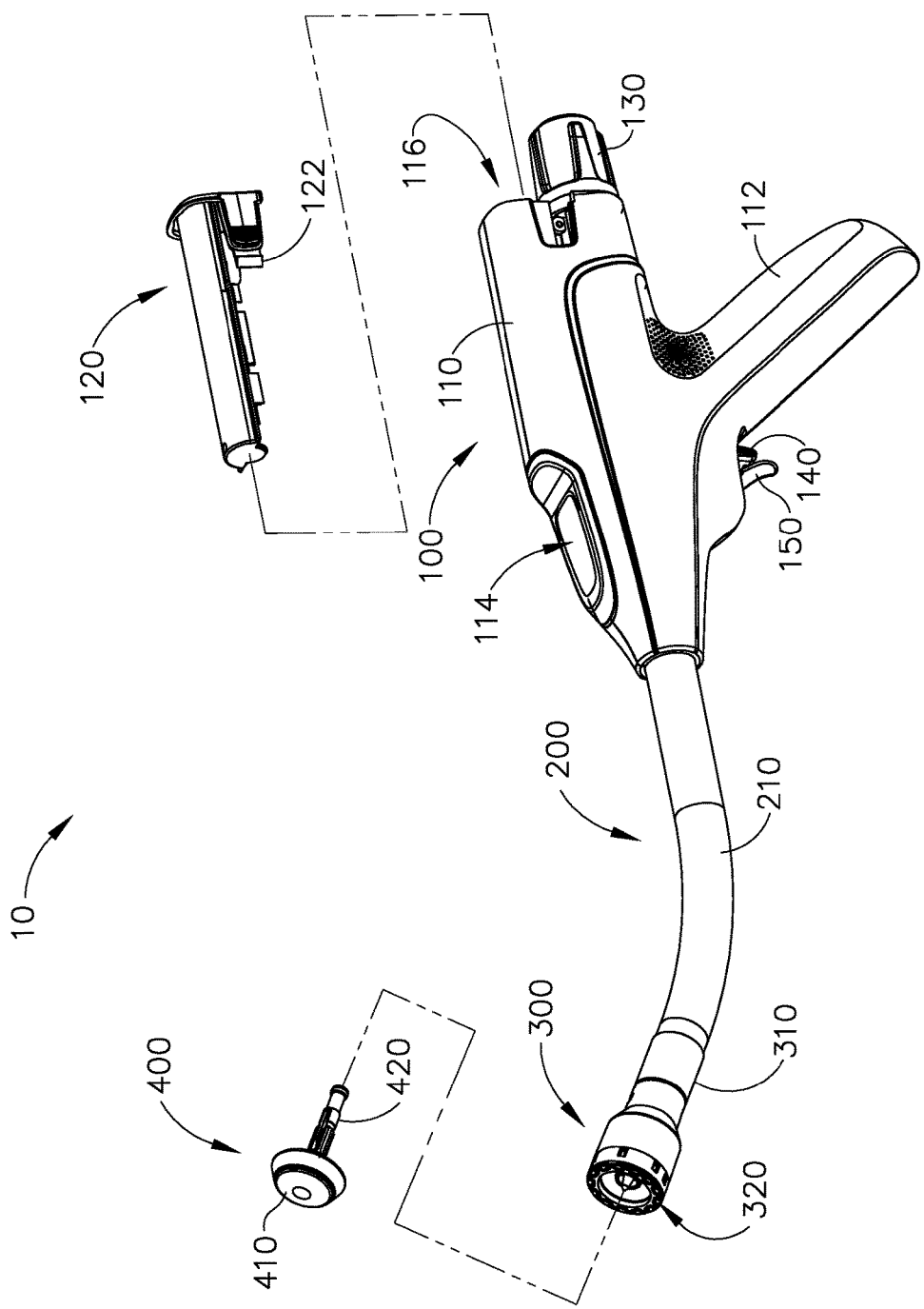
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
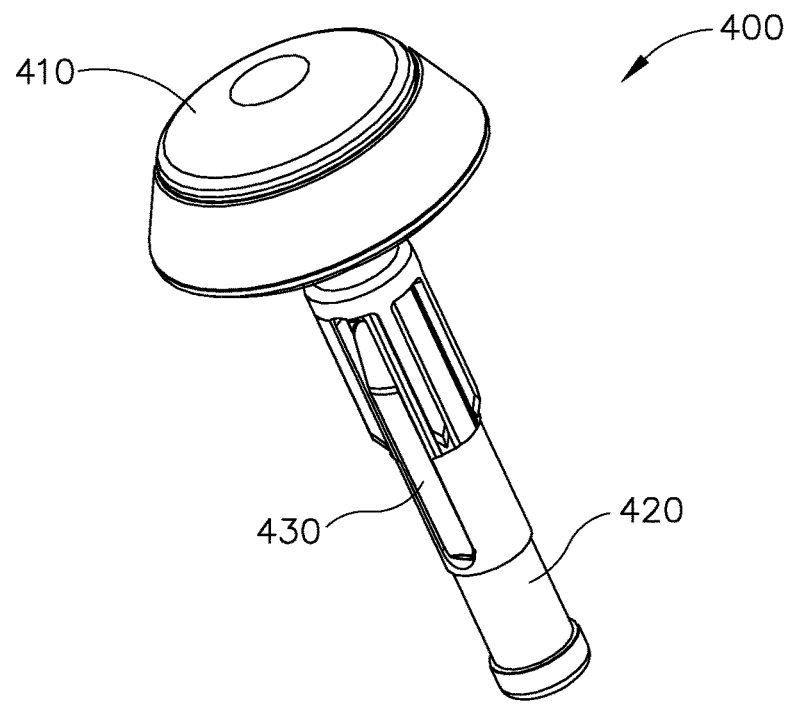
FIG. 3 depicts a perspective view of the anvil of the circular stapler of FIG. 1.
Figure 4:
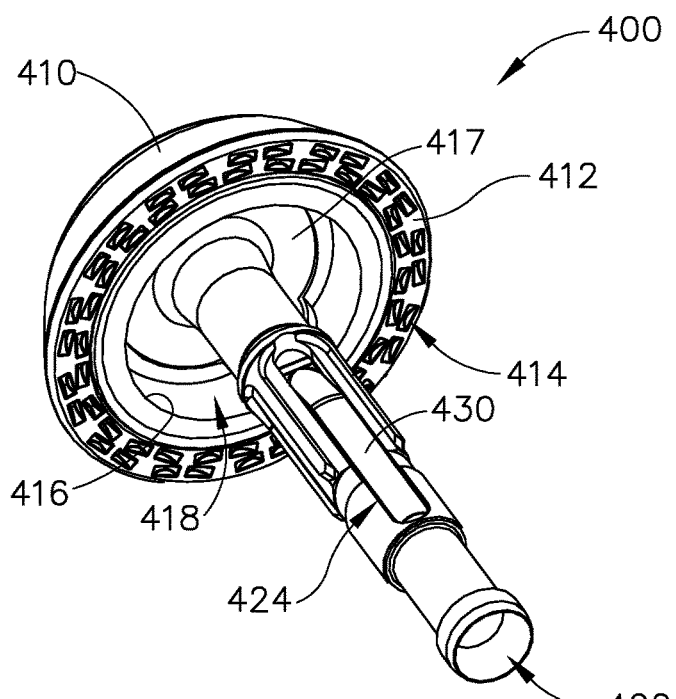
FIG. 4 depicts another perspective view of the anvil of FIG. 3.
Figure 5:
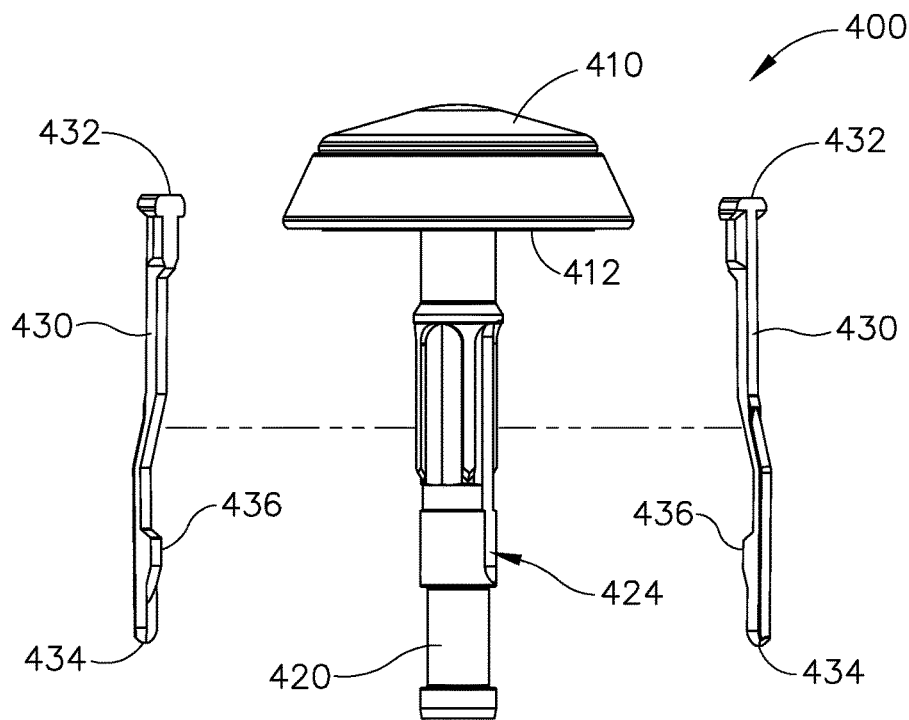
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

B. Exemplary Stapling Head Assembly

Figure 6:
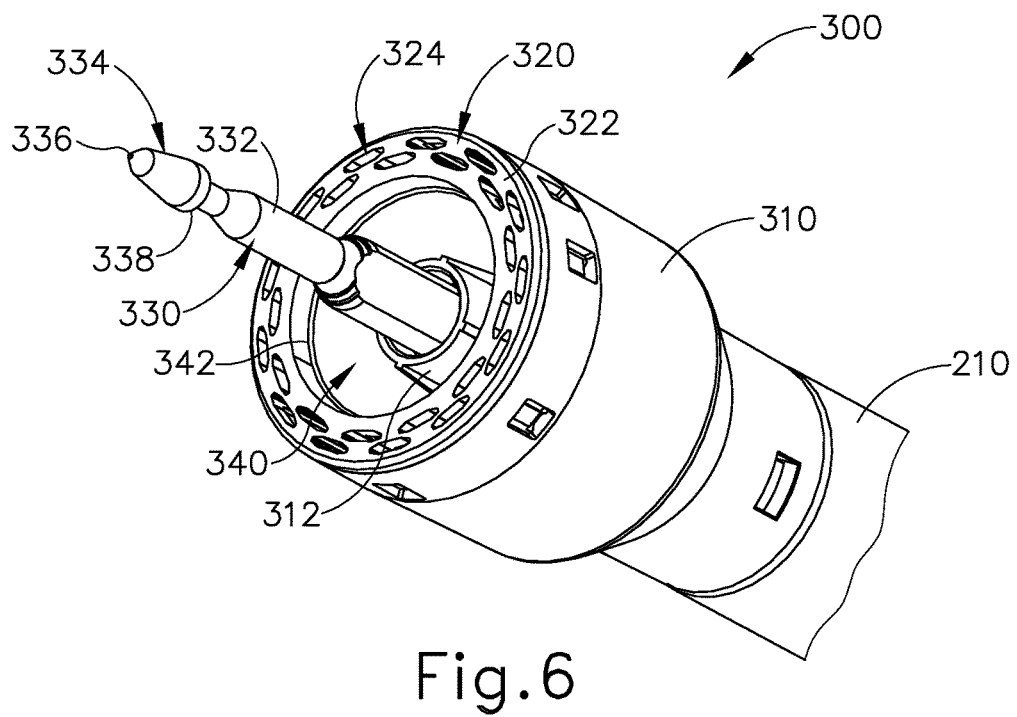
FIG. 6 depicts a perspective view of the stapling head assembly of the circular stapler of FIG. 1.
Figure 7:
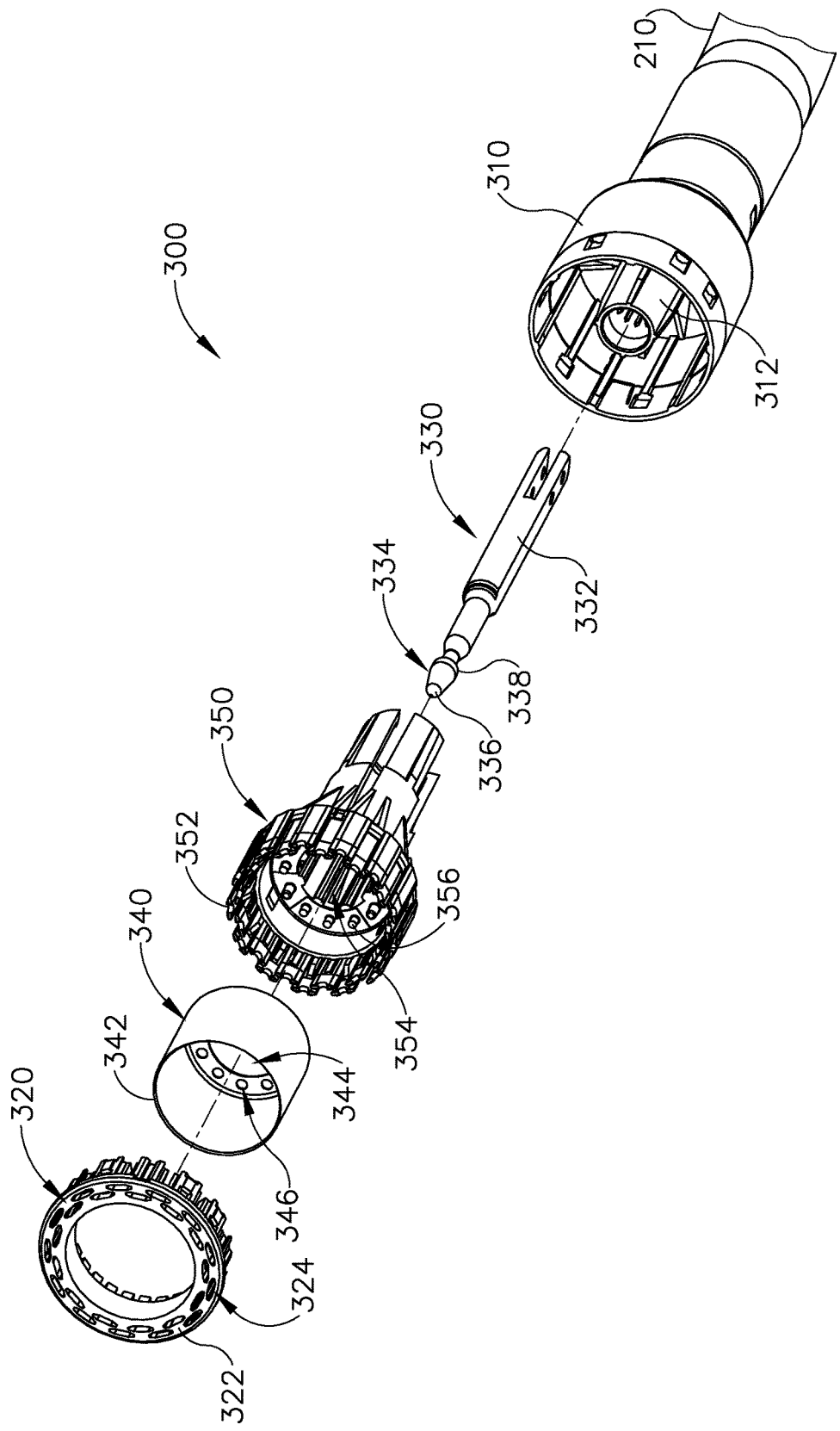
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

C. Exemplary Shaft Assembly

Figure 8:
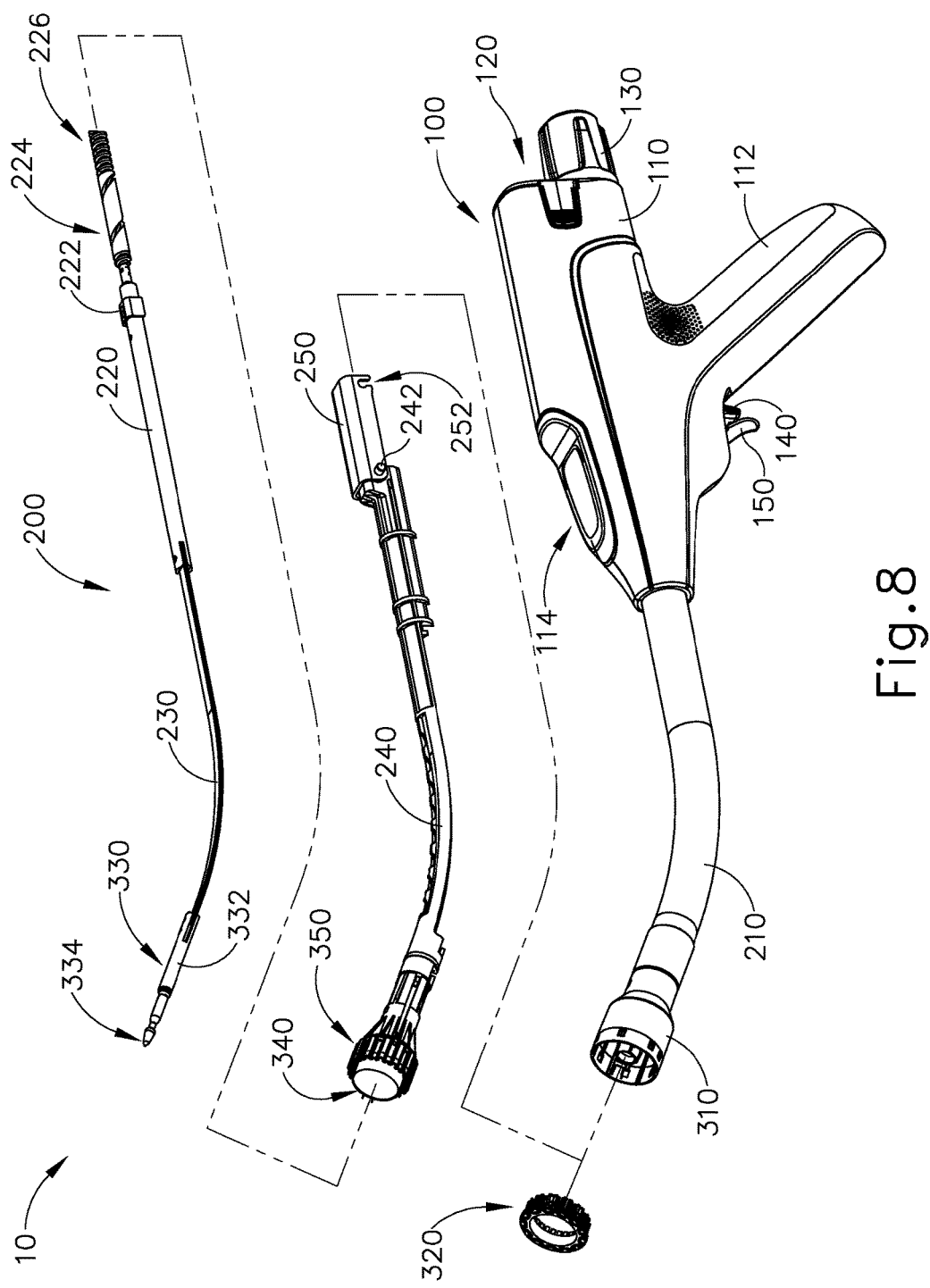
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100)

to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

D. Exemplary Actuator Handle Assembly

Figure 9:
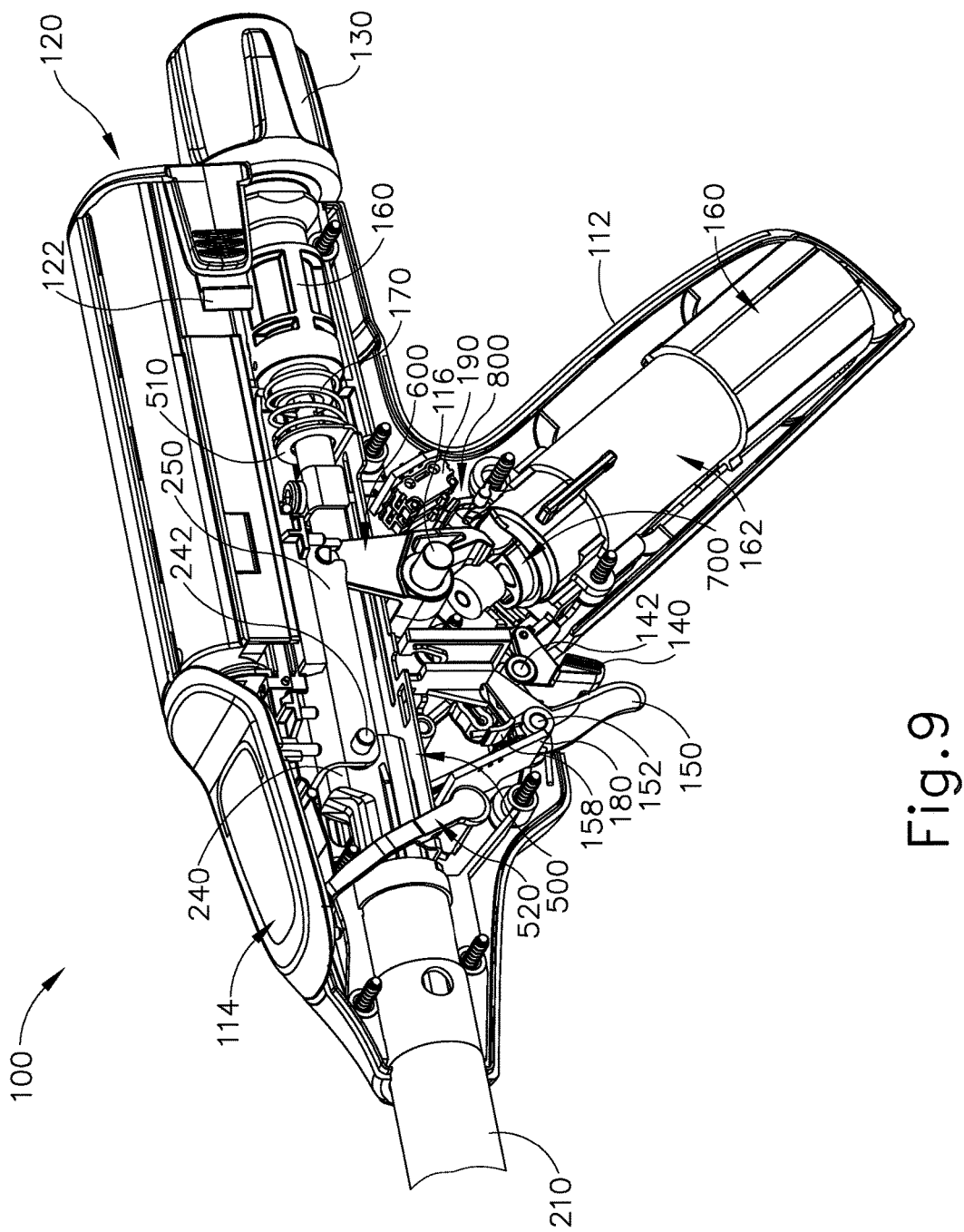
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1. Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
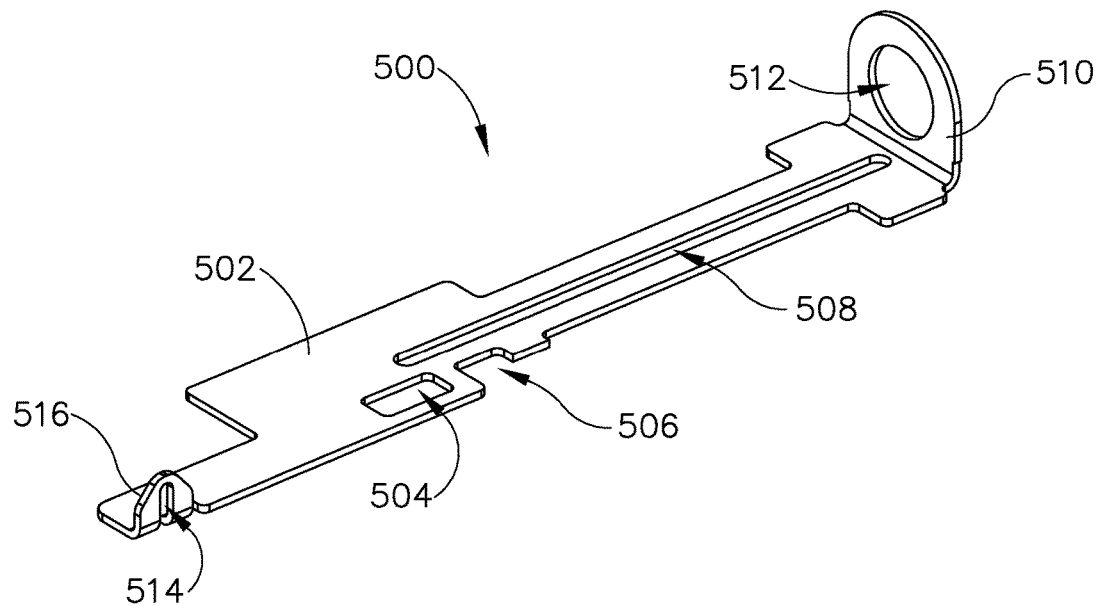
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
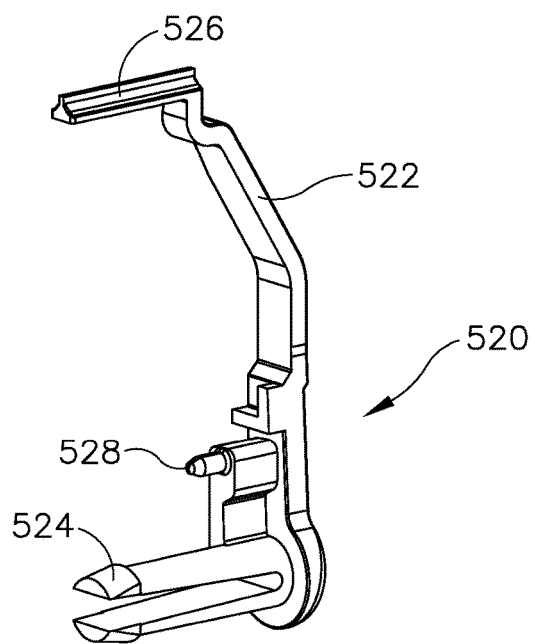
FIG. 11 depicts a perspective view of an indicator member of the handle assembly of FIG. 9.
Figure 12A:
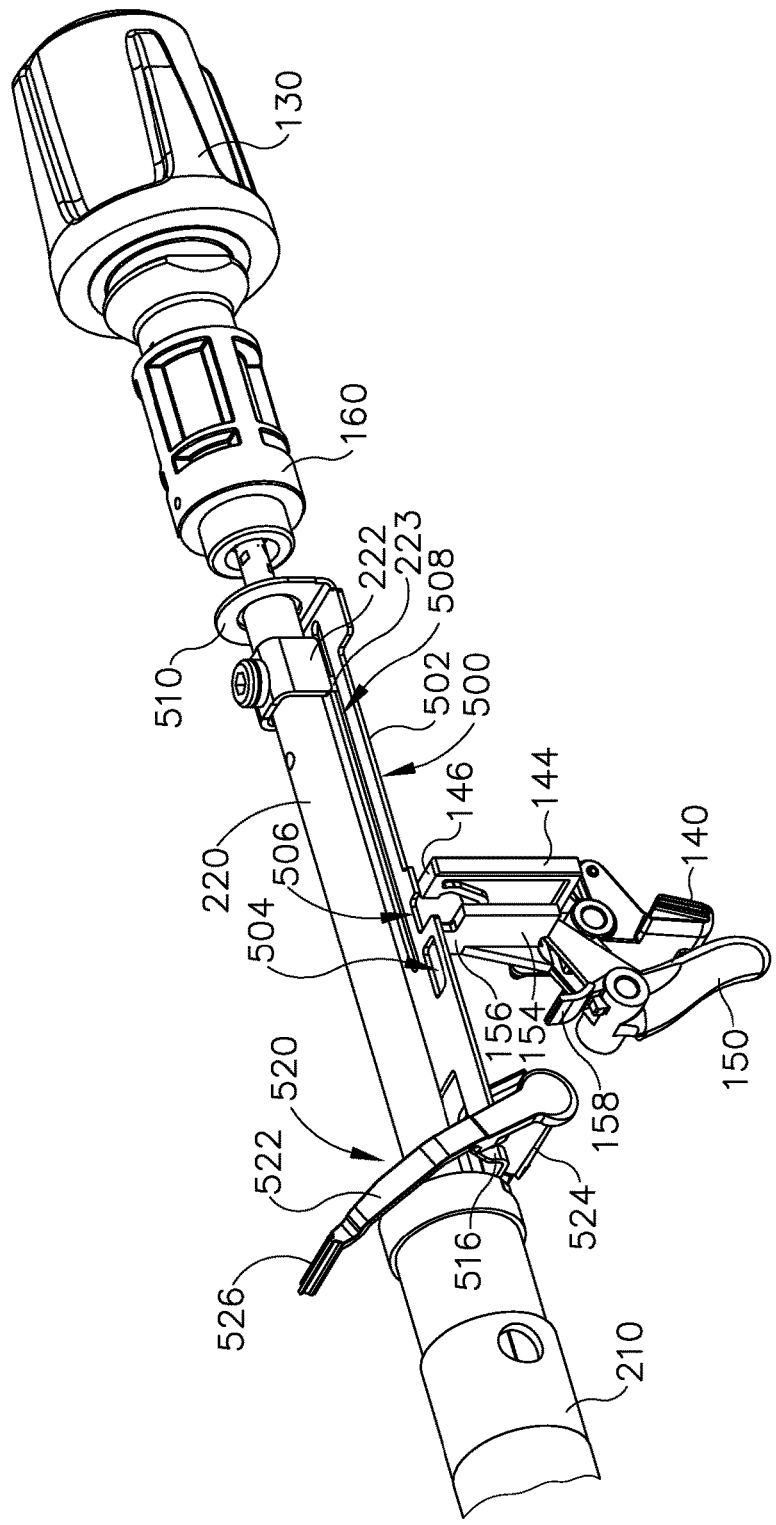
FIG. 12A depicts a perspective view of an anvil actuation assembly of the circular stapler of FIG. 1, an actuation rod in a first position.
Figure 12B:
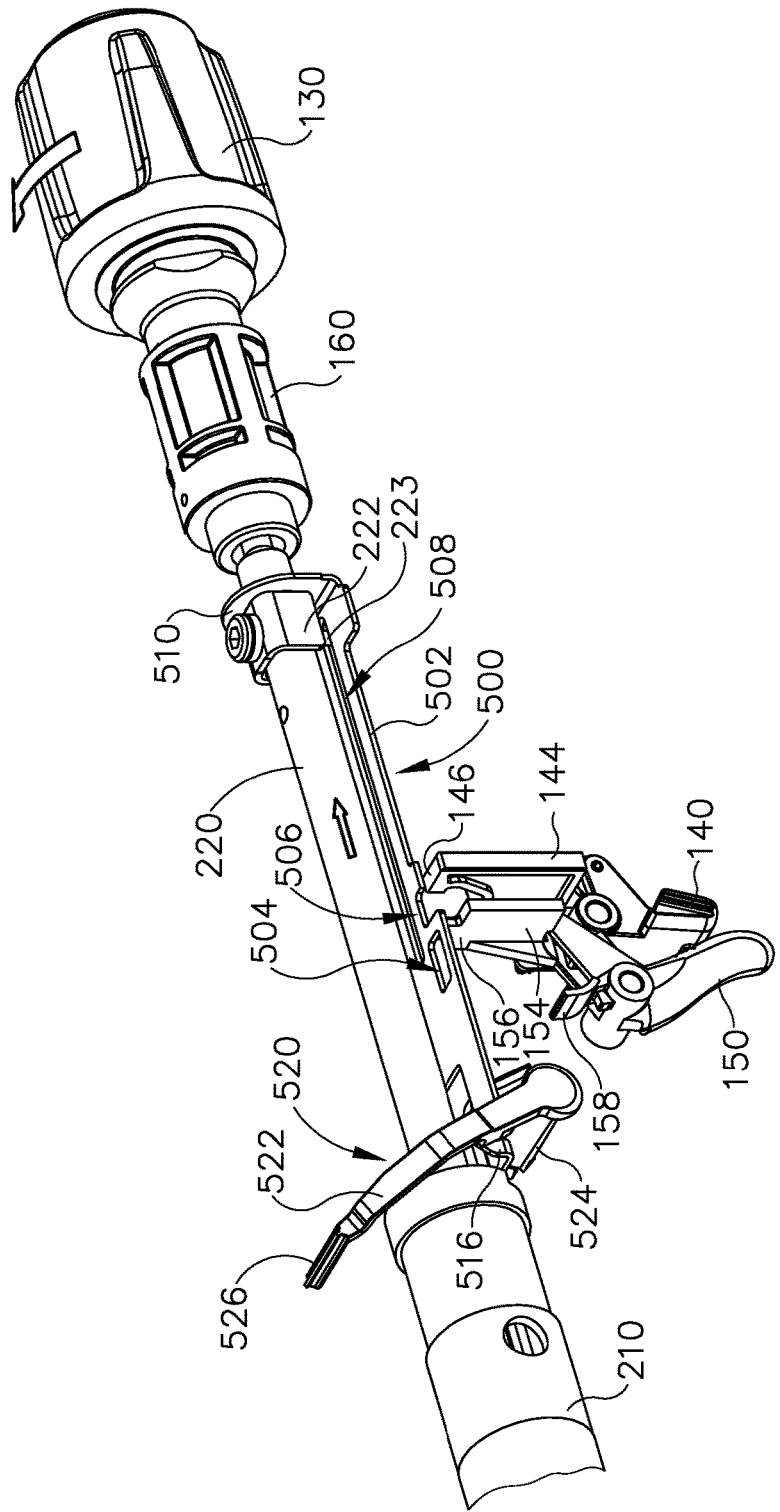
FIG. 12B depicts a perspective view of the anvil actuation assembly of FIG. 12A, with the actuation rod moved to a second position to engage the bracket of FIG. 10.
Figure 12C:
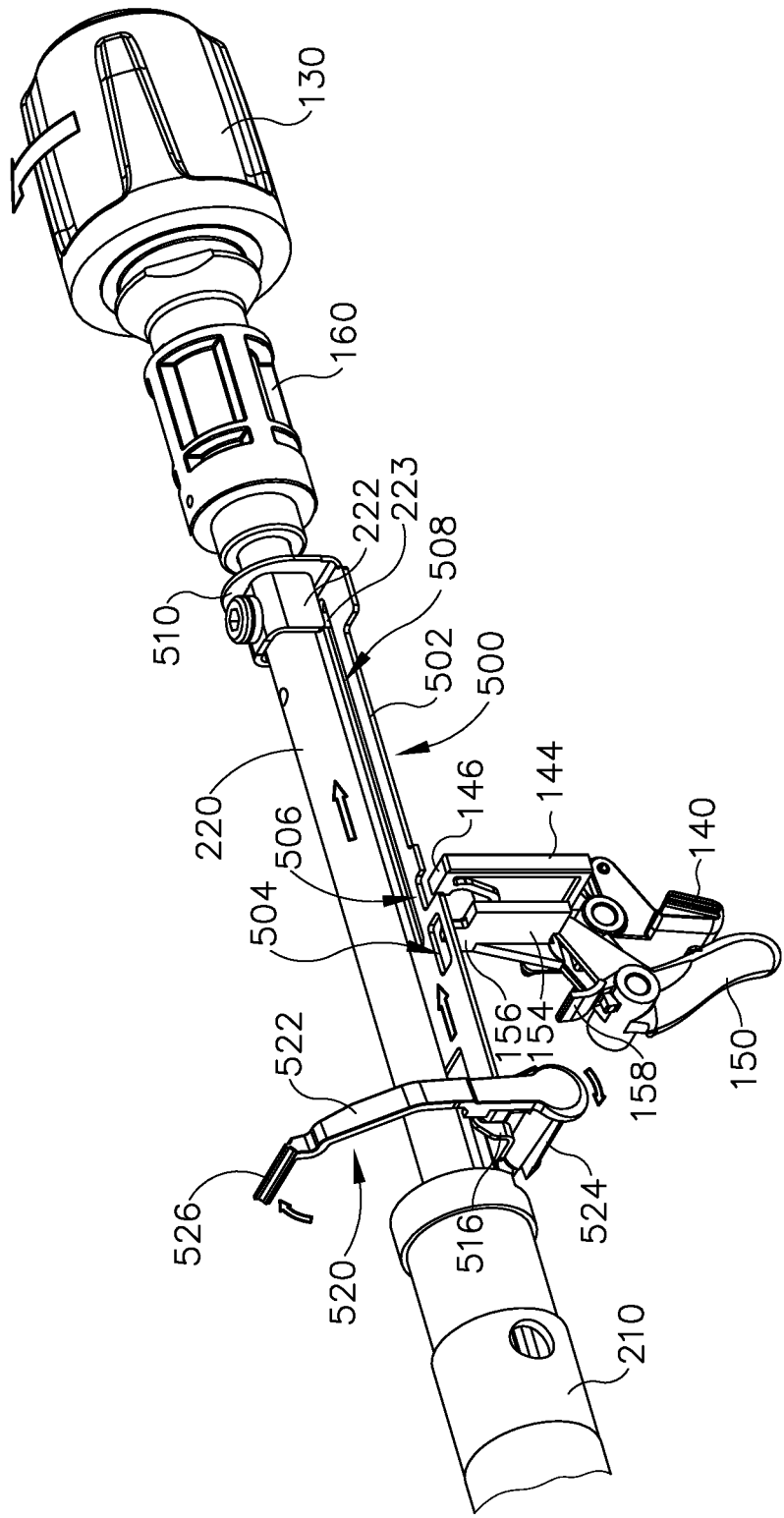
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330) and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
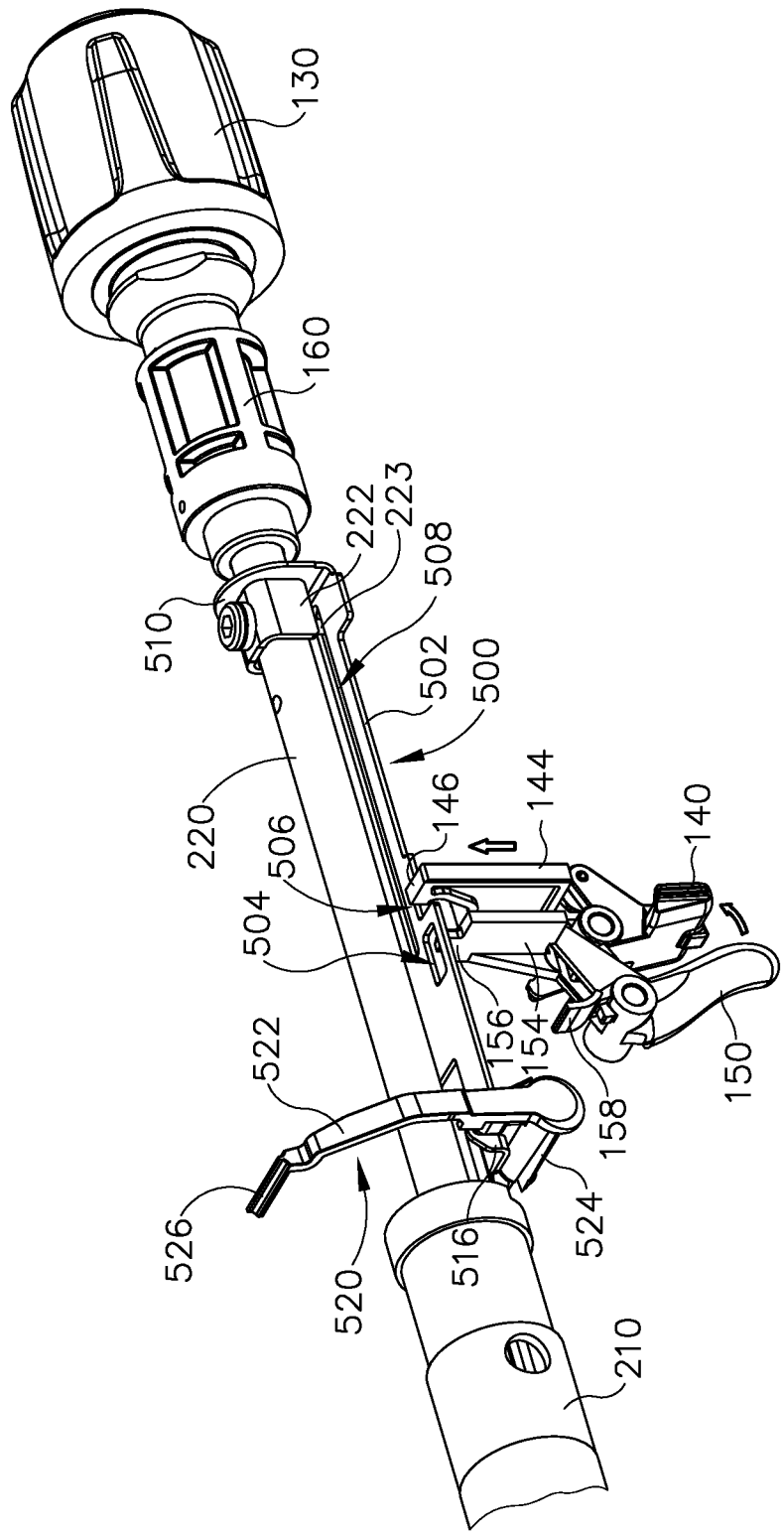
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
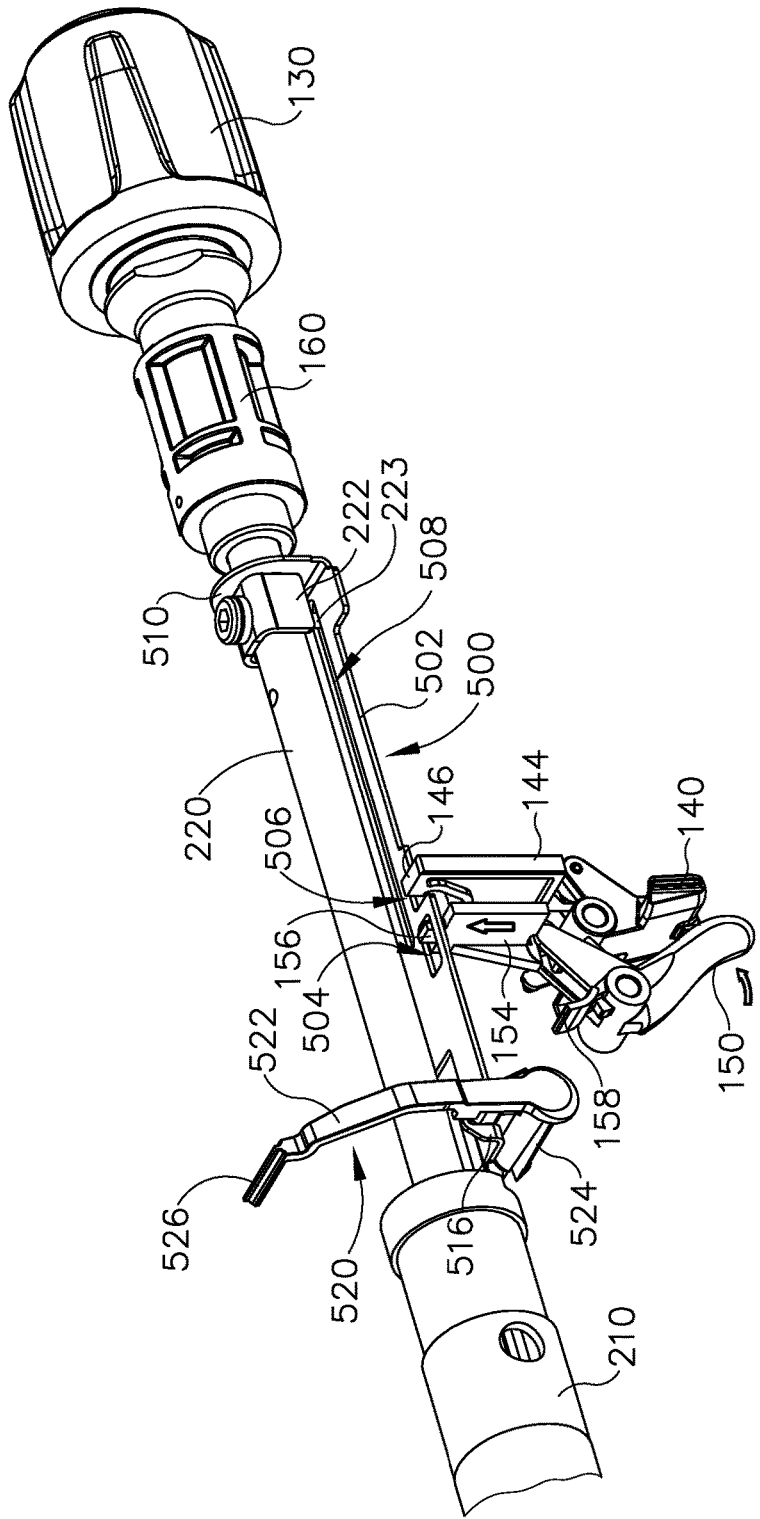
FIG. 12E depicts a perspective view of the anvil actuation assembly of FIG. 12A, with a firing trigger pivoted from a first position to a second position.
Figure 13:
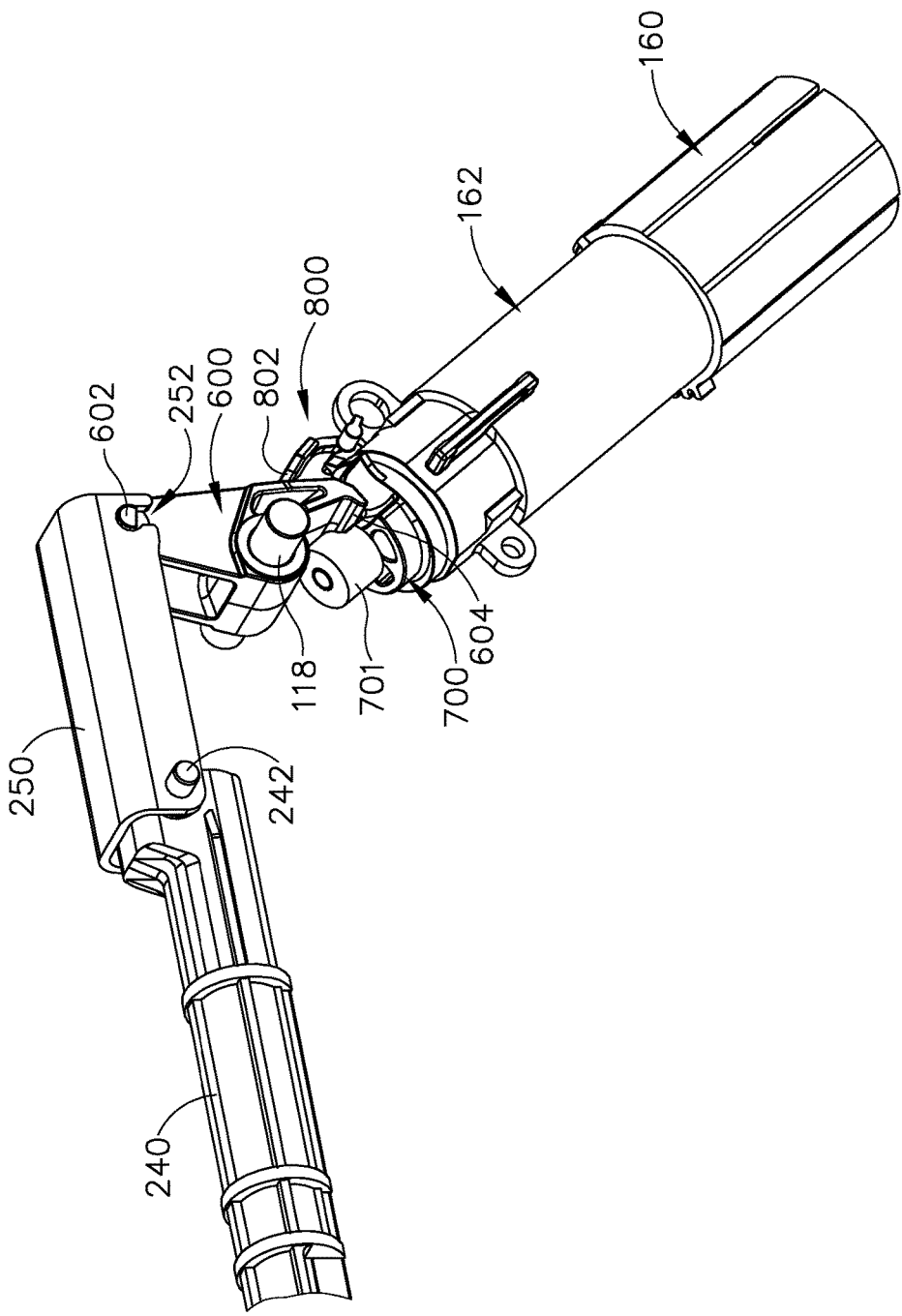
FIG. 13 depicts a perspective view of a stapling head actuation assembly of the circular stapler of FIG. 1.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
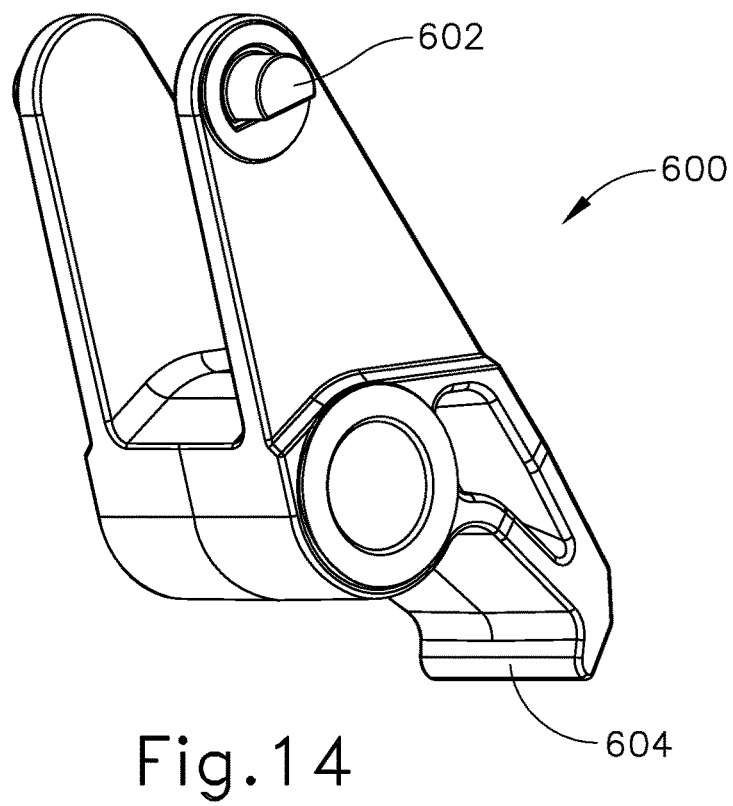
FIG. 14 depicts a perspective view of a cam follower of the stapling head actuation assembly of FIG. 13.
Figure 15:
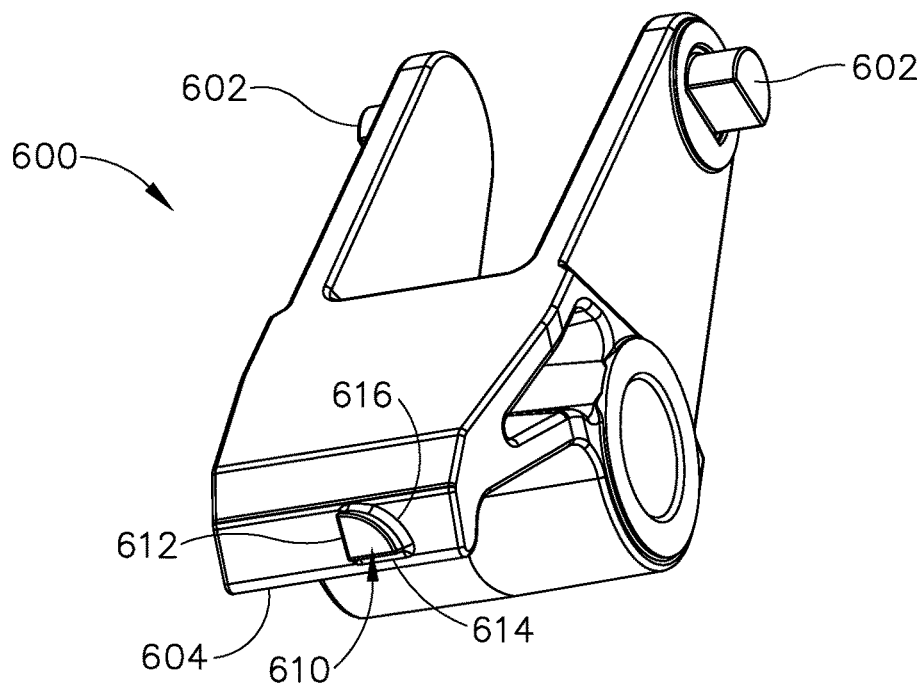
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
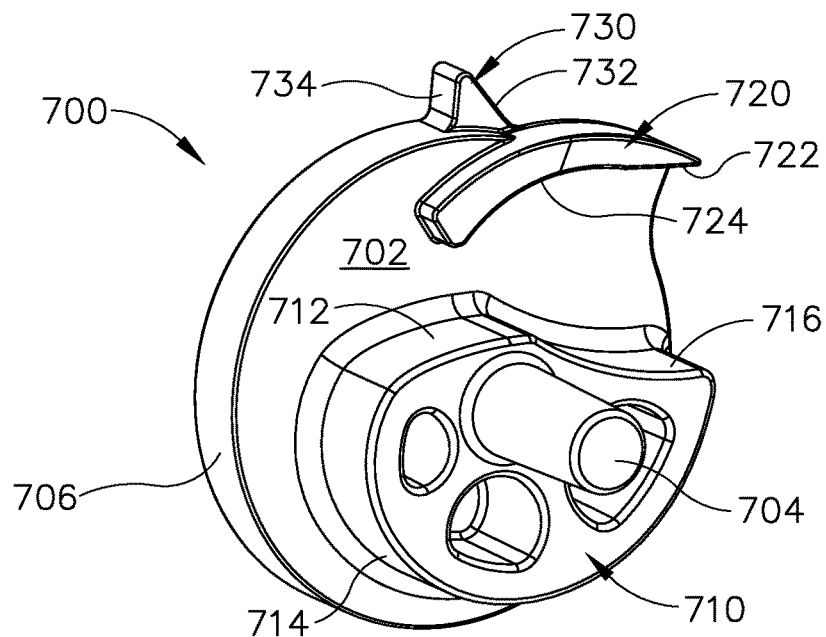
FIG. 16 depicts a perspective view of a rotary cam of the stapling head actuation assembly of FIG. 13.
Figure 17:
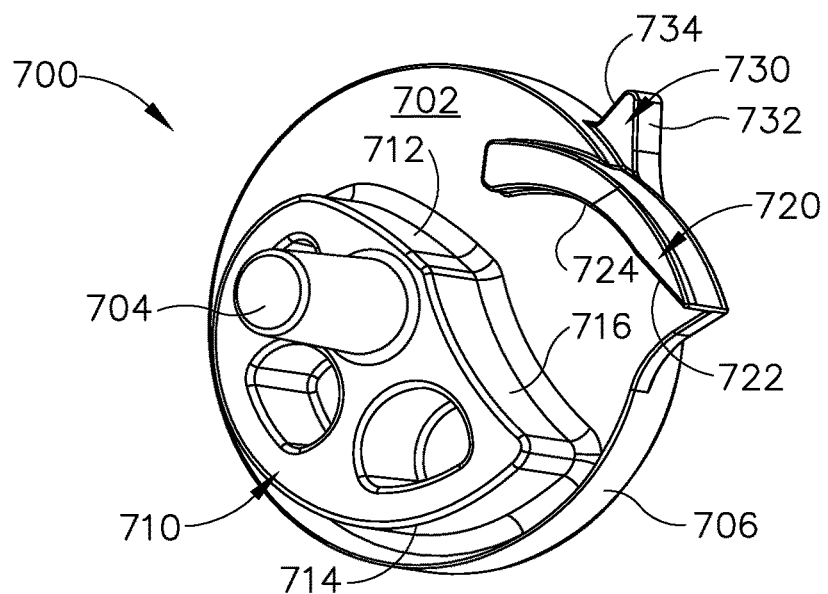
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
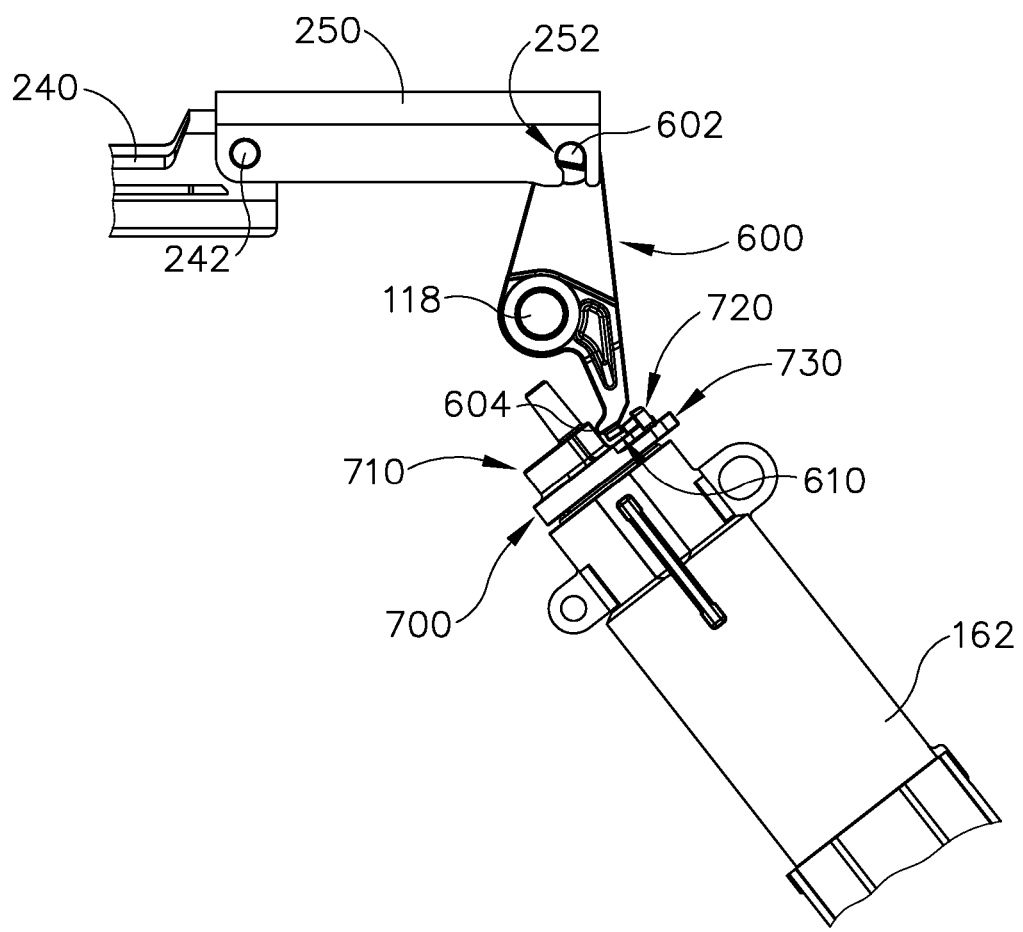
FIG. 18A depicts a side elevational view of the stapling head actuation assembly of FIG. 13, with the rotary cam in a first angular position and the cam follower in a first pivotal position.
Figure 18B:
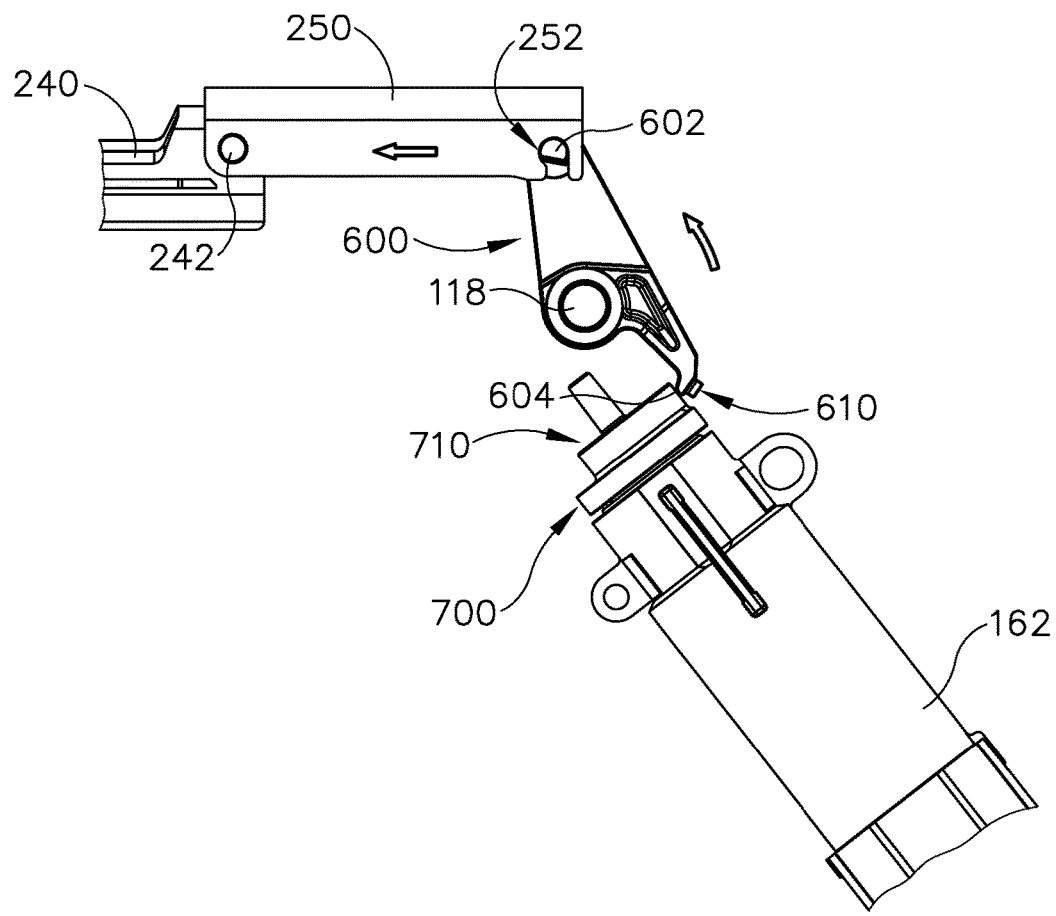
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118). In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
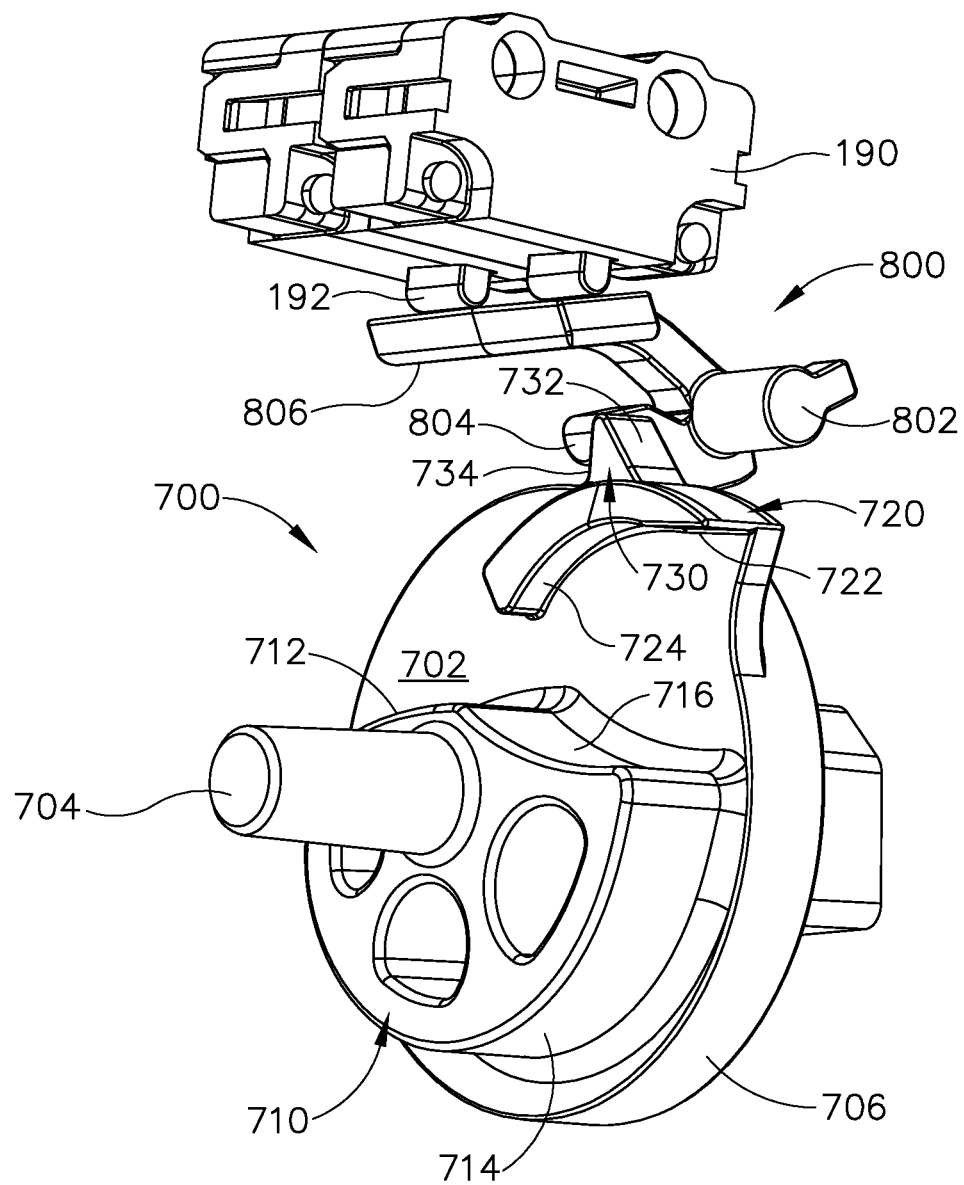
FIG. 19A depicts a perspective view of the rotary cam of FIG. 16, a rocker member, and a stop switch, with the rotary cam in a first angular position and the rocker member in a first pivotal position.
Figure 19B:
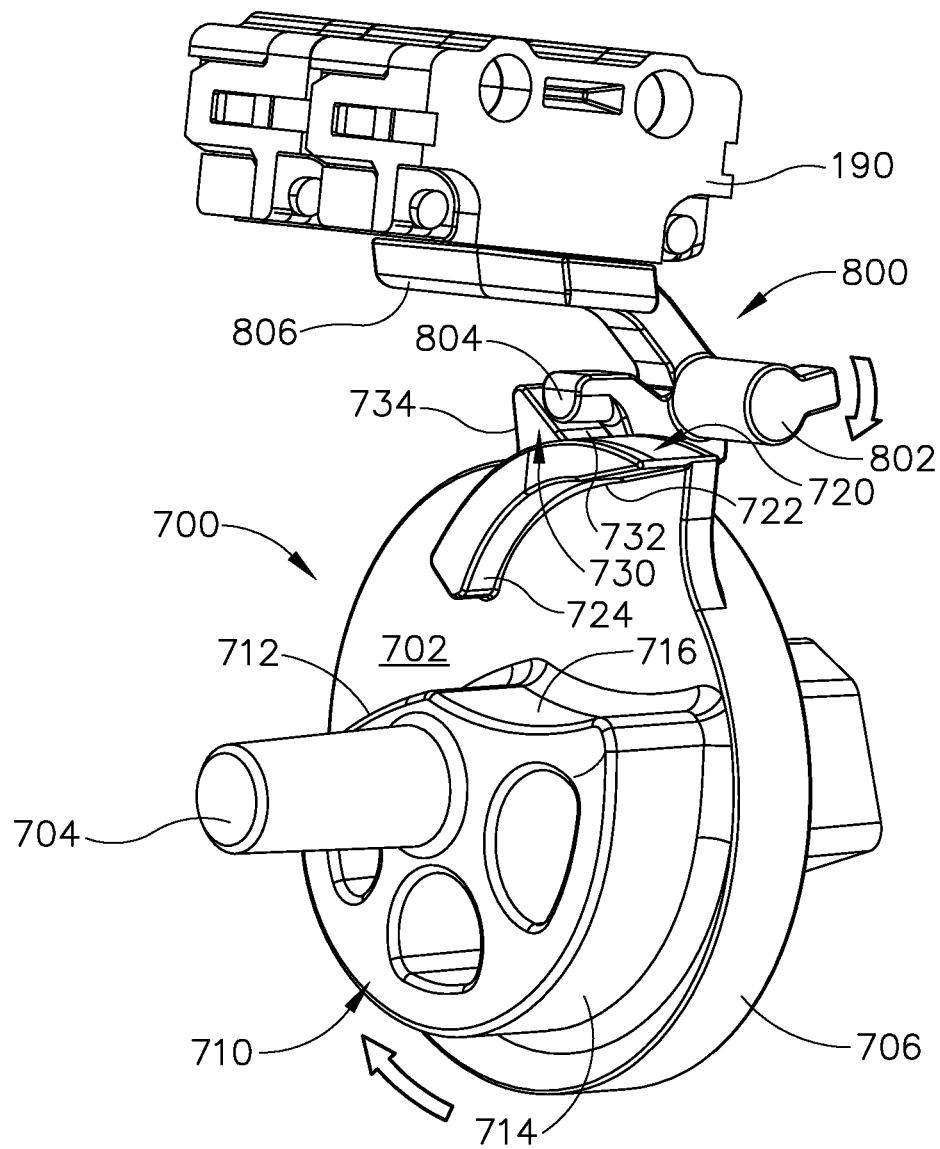
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch button (192) of a short circuit module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch button (192) of short circuit module (190). Short circuit module (190) is configured to prevent motor (160) from further activation when switch button (192) has been actuated. In some versions, short circuit module (190) couples battery pack (120) with a power sink, in addition to short circuiting motor (160), when switch button (192) is actuated. This may result in discharge of battery pack (120) in addition to stopping activation of motor (160) once an actuation stroke of stapling head assembly (300) has been completed. By way of example only, short circuit module (190) may be configured and operable in accordance with at least some of the teachings of U.S. Pub. No. 2015/0083774, issued as U.S. Pat. No. 9,907,552 on Mar. 6, 2018, the disclosure of which is incorporated by reference herein. Other suitable configurations will be apparent to those of ordinary skill in the art in view of the teachings herein.

Figure 20A:
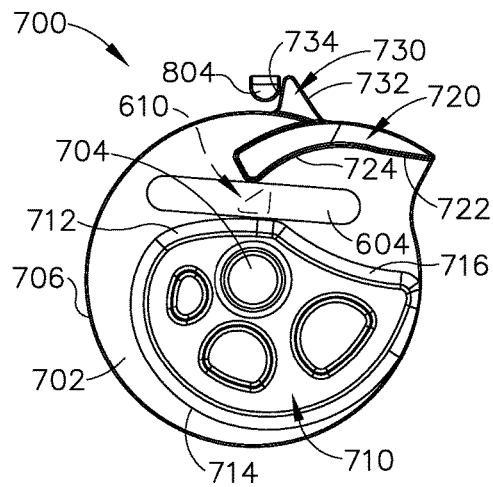
FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.
Figure 20B:
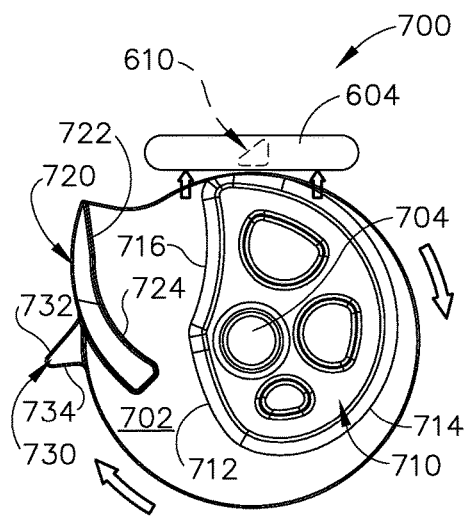
FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position.

FIGS. 20A-20D schematically depict the interaction between cam member (700), features of cam follower (600), and features of rocker member (800) as cam member (700)

rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (804), thereby driving bearing member (804) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

Figure 20C:
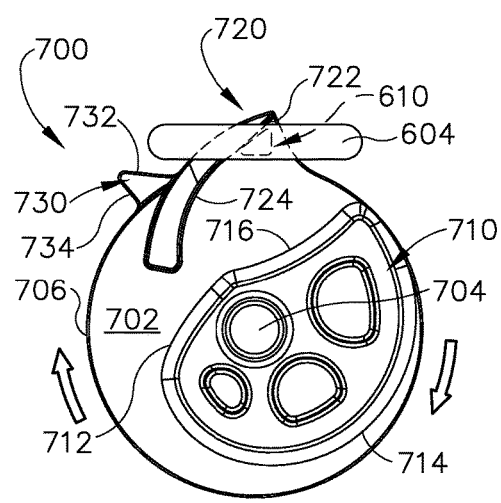
FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position.
Figure 20D:
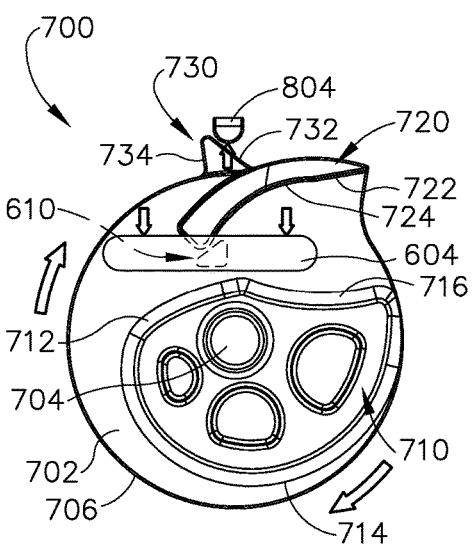
FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Short circuit module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate short circuit module (190) by rotating in a single angular direction through the range of motion shown in FIGS. 20A-20D. Other suitable ways in which knife member (340), staple driver member (350), and short circuit module (190) may be actuated will be apparent to those of ordinary skill in the art in view of the teachings herein.

E. Exemplary Anastomosis Procedure

Figure 21A:
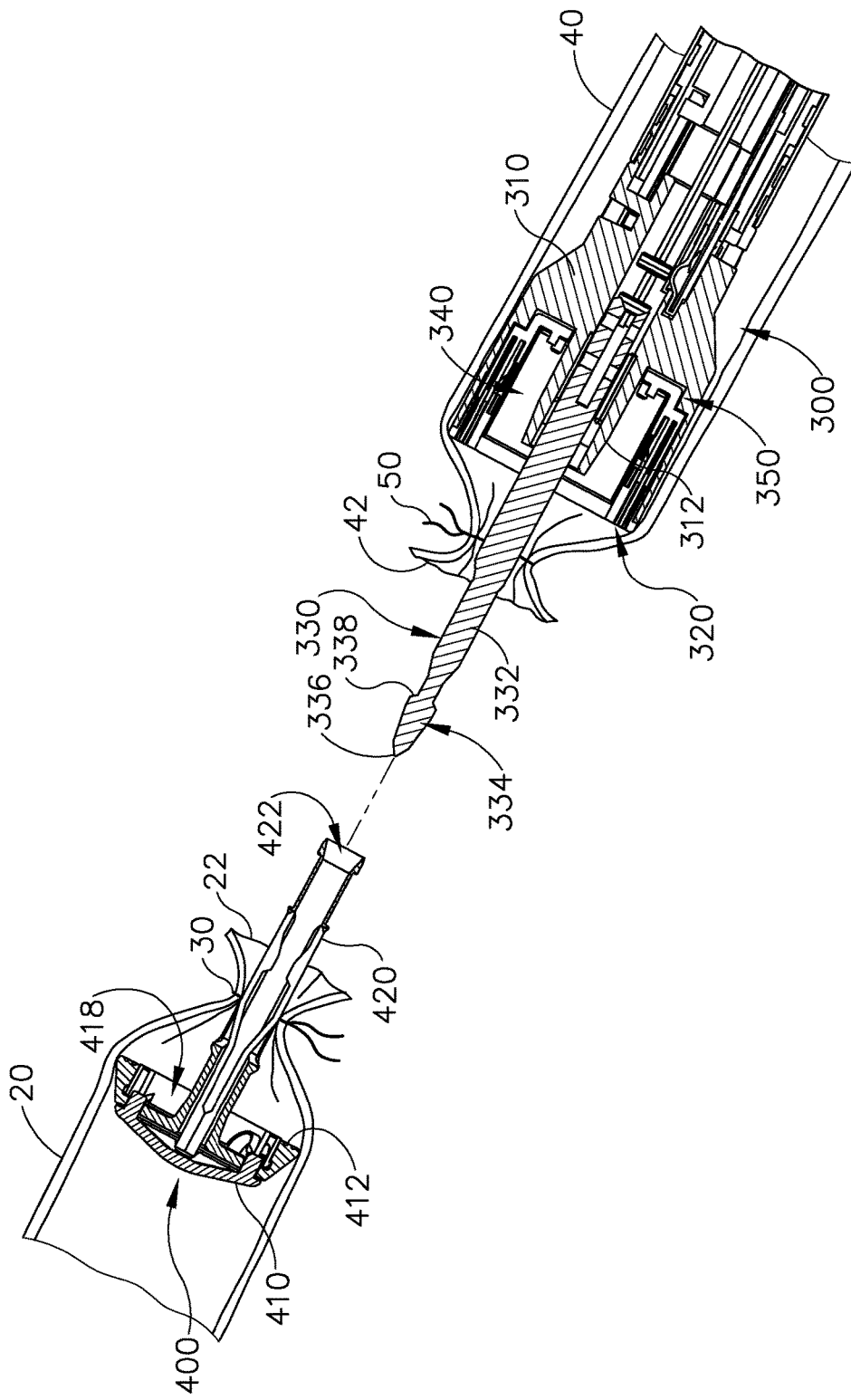
FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly.
Figure 21B:
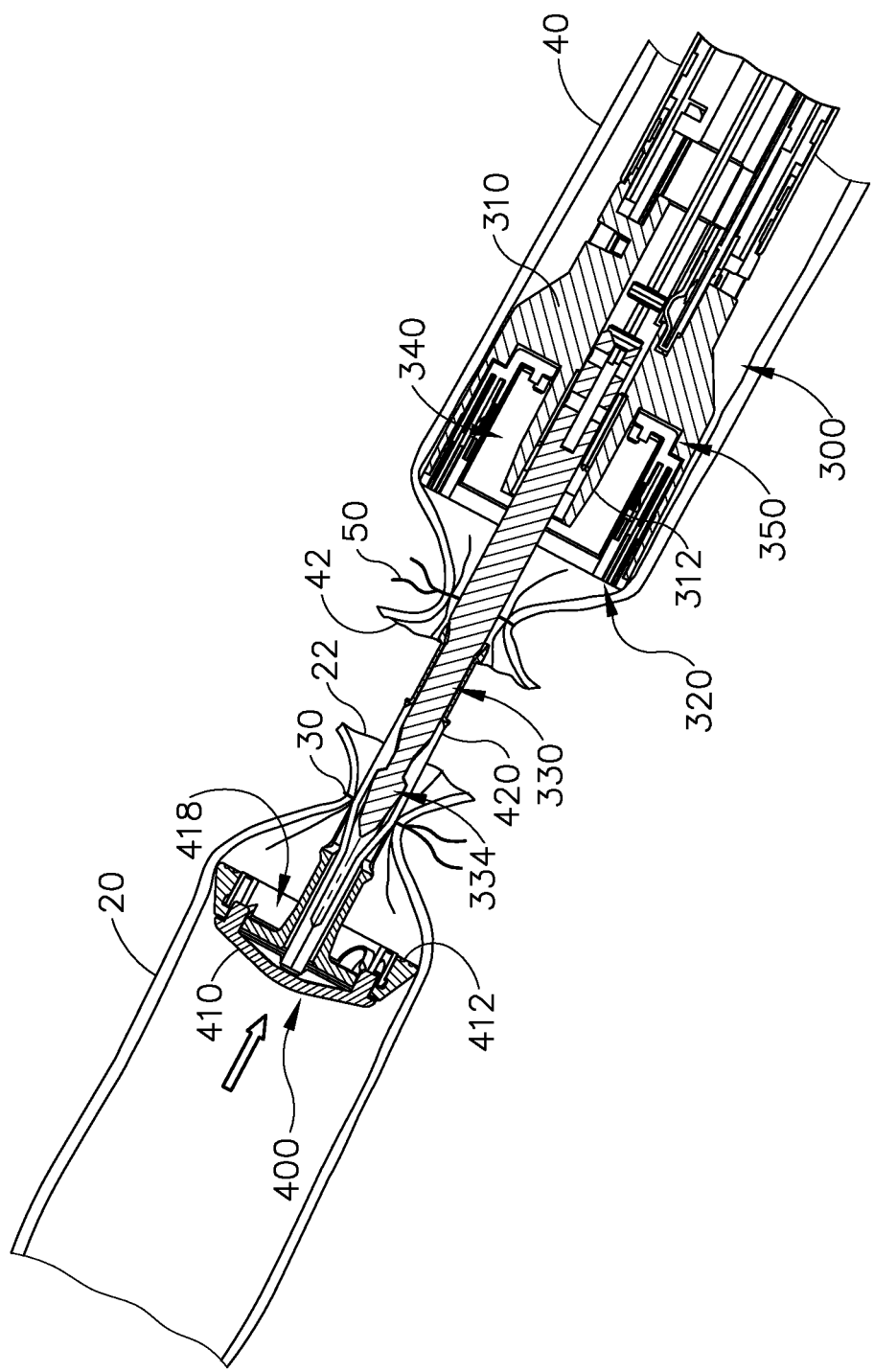
FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly.
Figure 21C:
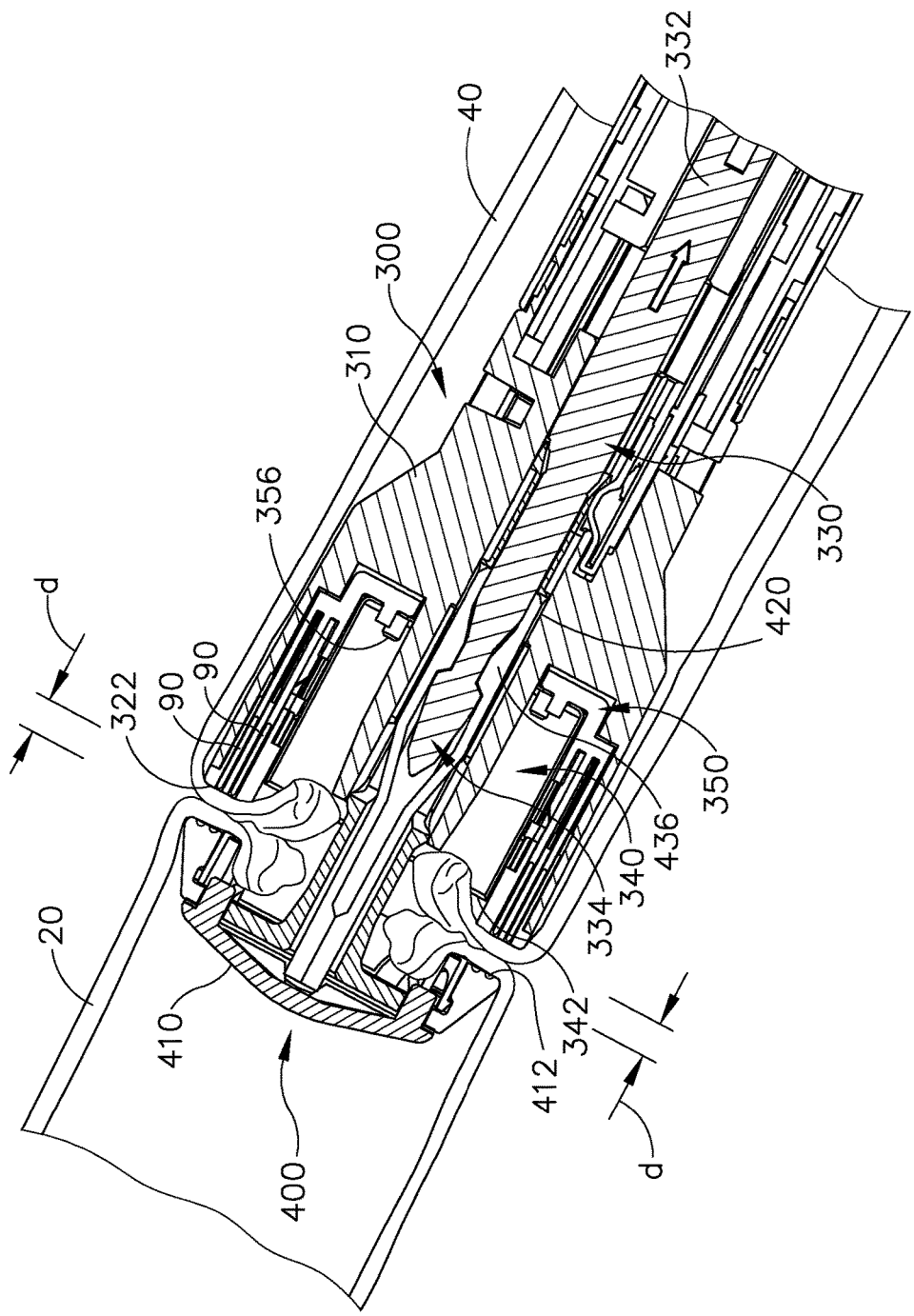
FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Figure 21D:
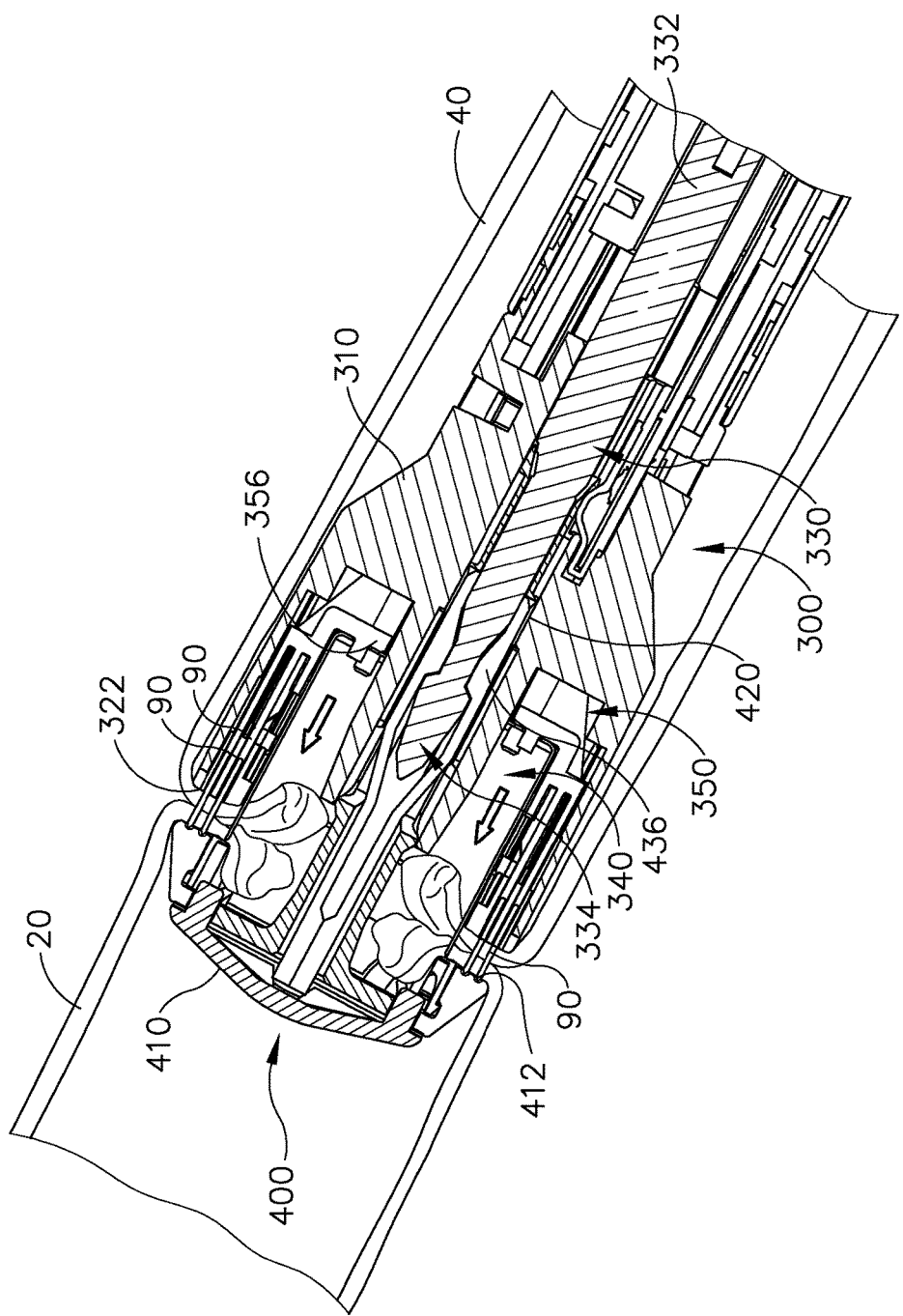
FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue.

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS. 20A-20D). This rotation of cam member (700) actuates stapling head assembly (300) by driving knife member (340) and staple driver member (350) distally as shown in FIG. 21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary Anvil Attachment Indicators

In some versions of instrument (10) it may desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition or in the alternative, features may be configured to prevent firing of stapling head assembly (300) unless anvil (400) is properly attached to trocar (300). For instance, if anvil (400) is not properly attached to trocar (330), stapling head assembly (300) may be prevented from firing. If anvil (400) is properly attached to trocar (330), firing of stapling head assembly (300) may be enabled. Various examples of such features will be described in greater detail below; while other examples will be apparent to those of ordinary skill in the art in view of the teachings herein. Moreover, the following teachings may be applied to devices that are used in various other contexts.

A. Exemplary Dome Switch Assembly

FIGS. 22A-23B depict a version of stapling head assembly (300) including a switch assembly (3000). It should be understood that this version of stapling head assembly (300) may be readily incorporated into instrument (10). Switch assembly (3000) includes a dome switch (3010) and a resilient actuator spring (3020). Actuator spring (3020) is secured within a cavity (3012) formed within tubular casing (310). Dome switch (3010) is positioned between a pair of flanges (3022, 3024) of actuator spring (3020) such that movement of flange (3022) toward flange (3024) will actuate dome switch (3010). As will be discussed in more detail below, proximal movement of anvil (400), when properly secured to trocar (330), causes movement of flange (3022) toward flange (3024) so as to actuate dome switch (3010). Actuation of dome switch (3010) may provide audible, tactile, and/or visible feedback to an operator indicating proper attachment. Various suitable features that may be used to provide such a response to actuation of dome switch (3010) will be apparent to those of ordinary skill in the art in view of the teachings herein. Additionally or alternatively, actuation of dome switch (3010) may enable firing of stapling head assembly (300). In other words, unless dome switch (3010) has been actuated, stapling head assembly (300) may not be fired in some versions.

Figure 22A:
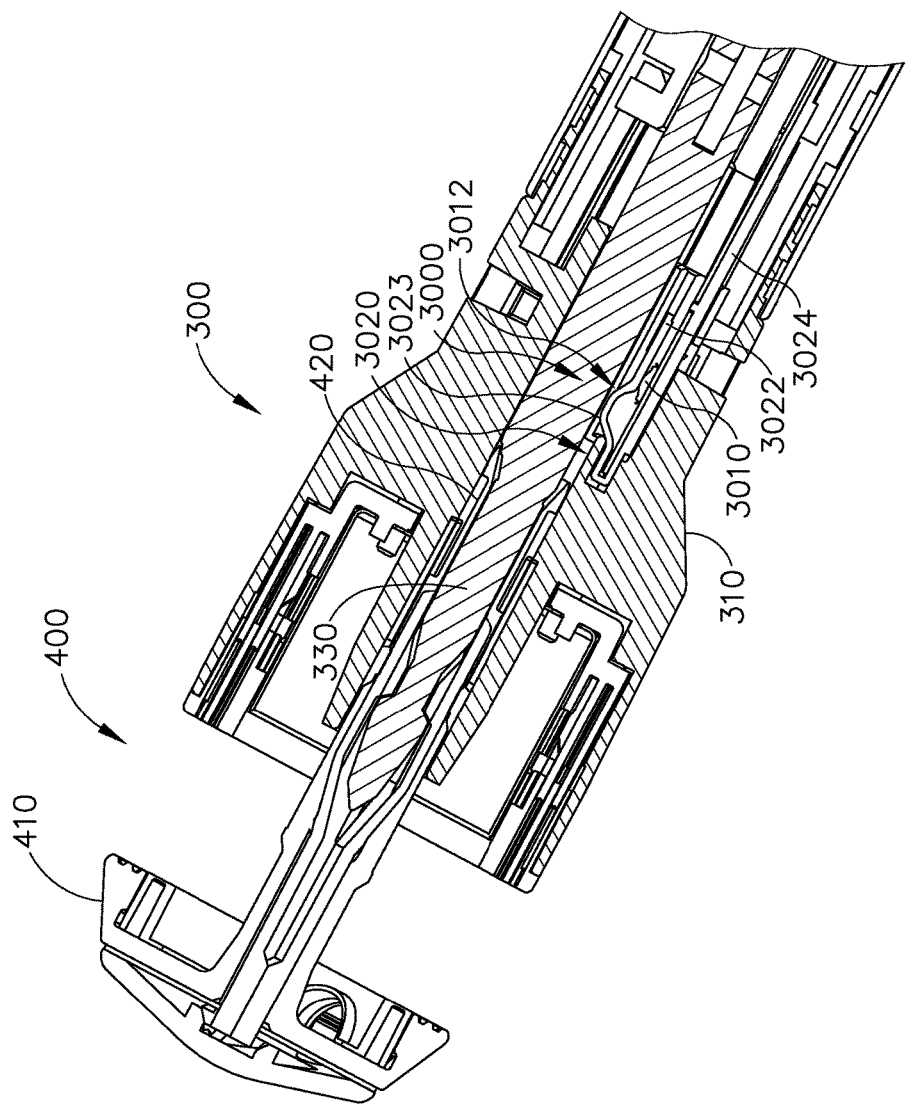
FIG. 22A depicts a cross-sectional side view of the distal end of an exemplary alternative circular stapler, with a contact switch of the circular stapler in an open state.
Figure 22B:
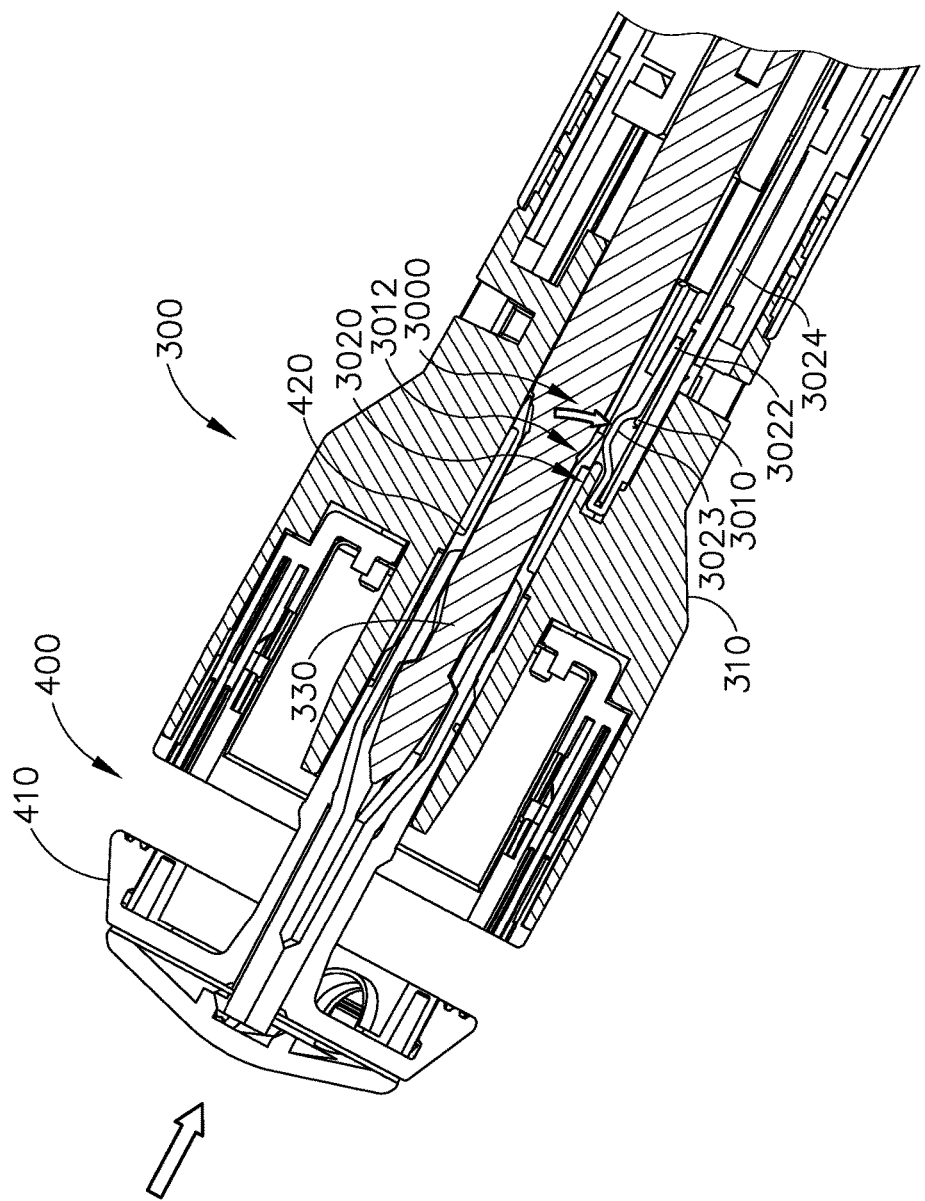
FIG. 22B depicts a cross-sectional side view of the distal end of the circular stapler of FIG. 22A, with the contact switch of FIG. 22A moved into a closed state by proximal translation of a trocar and an anvil of the circular stapler.
Figure 23B:
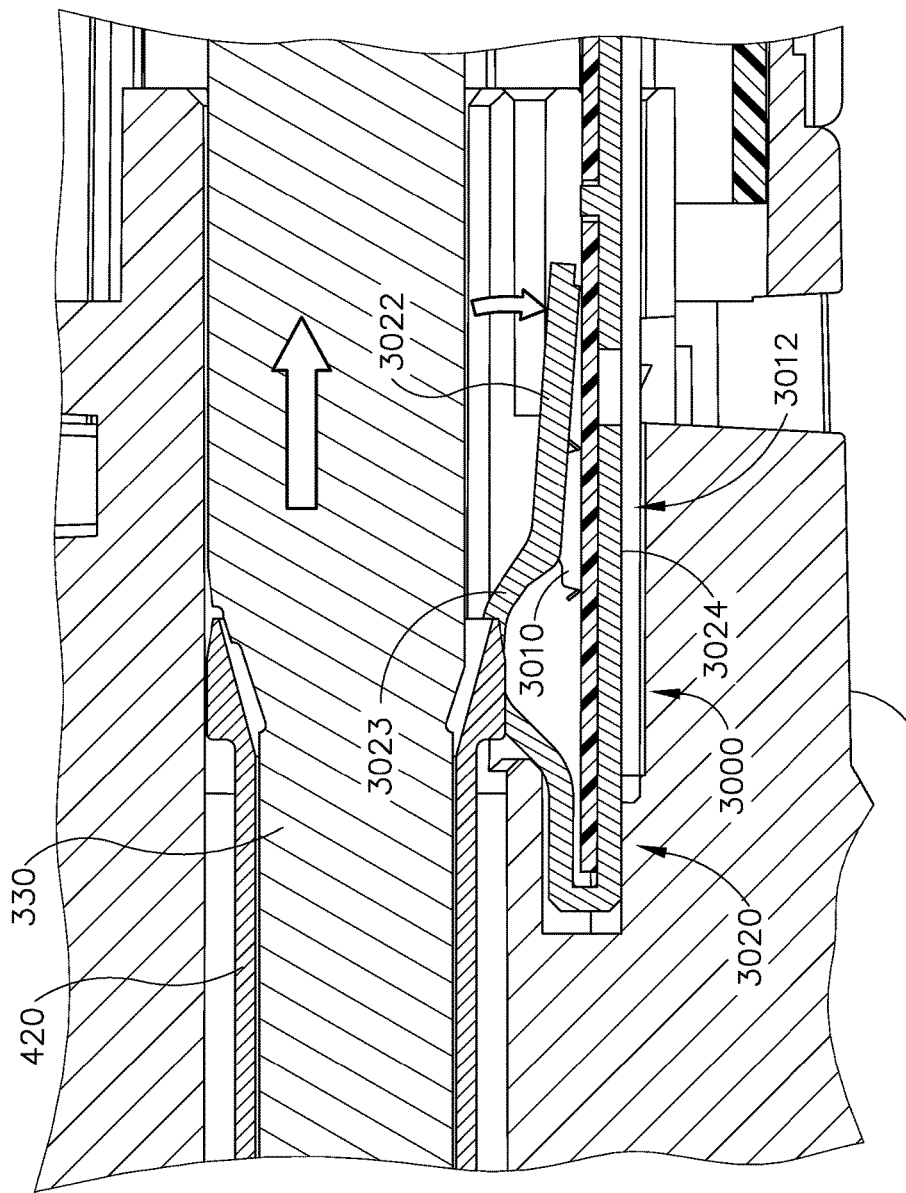
FIG. 23B depicts a cross-sectional side view of the distal end of the circular stapler of FIG. 22A, with the contact switch of FIG. 22A moved into the closed state of FIG. 22B by proximal translation of the trocar and the anvil of the circular stapler.

After anvil (400) is secured to trocar (330), the operator then rotates knob (130) so as to cause trocar (330) and anvil (400) to retract proximally as described above with reference to FIGS. 12A-12C. When trocar (330) and anvil (400) are properly secured to one another, this proximal retraction of trocar (330) and anvil (400) compresses the tissue of tubular anatomical structures (20, 40) between surfaces (412, 322) of anvil (400) and stapling head assembly (300). When trocar (330) and anvil (400) are not properly secured to one another, trocar (330) is retracted proximally without anvil (400) such that the tissue of tubular anatomical structures (20, 40) remains uncompressed. When trocar (330) and anvil (400) are properly secured to one another, as trocar (330) and anvil (400) are retracted proximally, a proximal end of shank (420) of anvil (400) engages a raised portion (3023) of flange (3022) of actuator spring (3020) so as to drive flange (3022) toward flange (3024), thereby actuating dome switch (3010) as shown in FIGS. 22B and 23B. As mentioned above, such actuation of dome switch (3010) may provide audible, tactile, and/or visible feedback to an operator indicating proper attachment. Additionally or alternatively, such actuation of dome switch (3010) may enable firing of stapling head assembly (300). In other words, unless such actuation of dome switch (3010) has been actuated, stapling head assembly (300) may not be fired.

B. Exemplary Contact Switch Assembly

Figure 24:
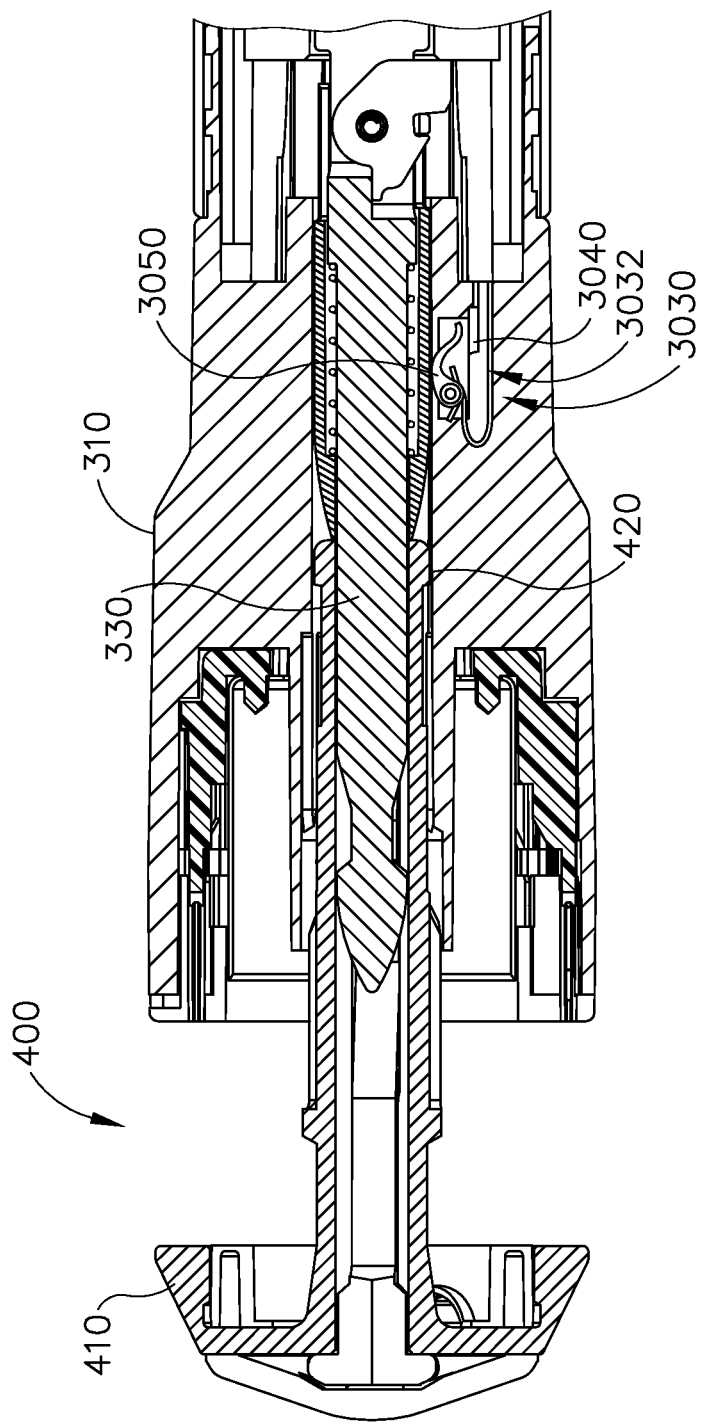
FIG. 24 depicts a cross-sectional side view of the distal end of another exemplary alternative circular stapler.
Figure 25A:
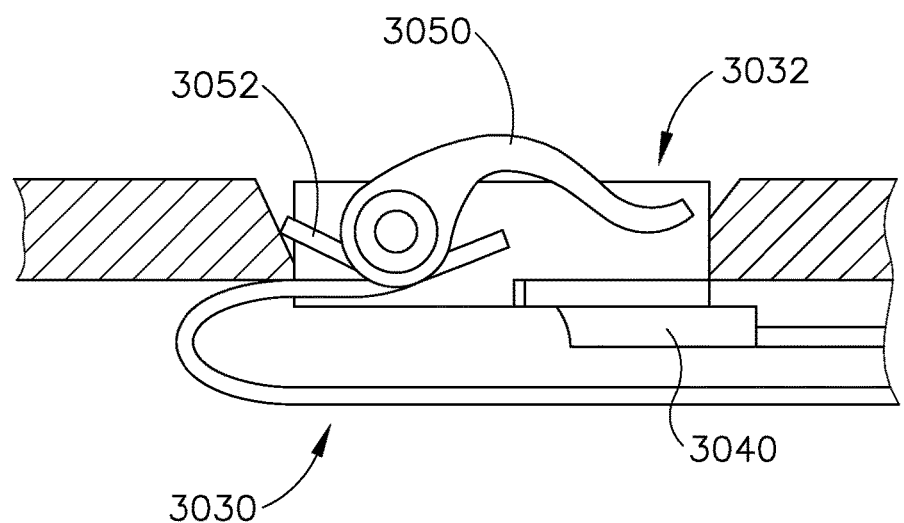
FIG. 25A depicts a detailed cross-sectional side view of the distal end of the circular stapler of FIG. 24, with a contact switch of the circular stapler in an open state.
Figure 25B:
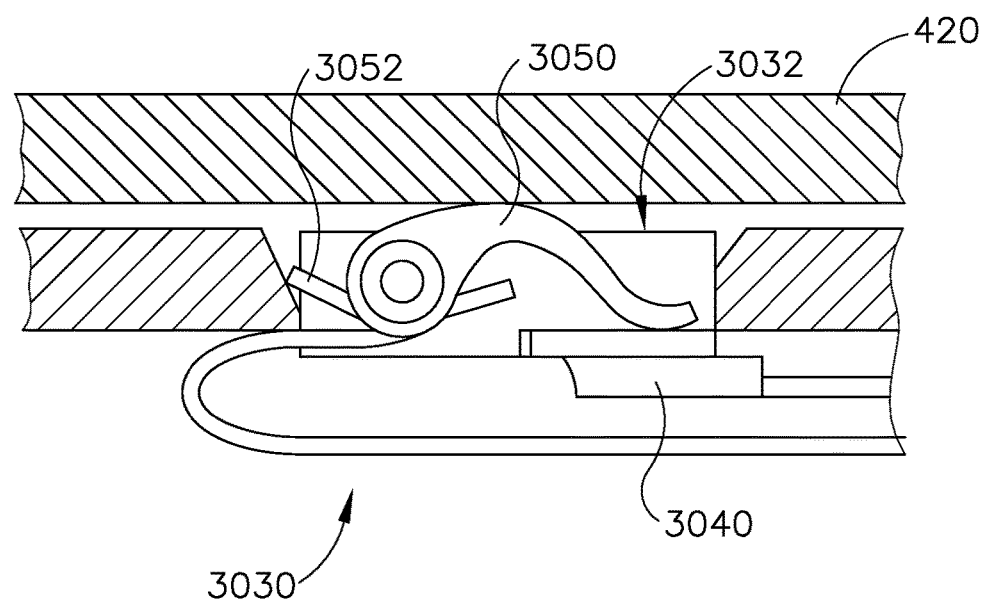
FIG. 25B depicts a detailed cross-sectional side view of the distal end of the circular stapler of FIG. 24, with the contact switch of FIG. 25A moved into a closed state by proximal translation of a trocar and an anvil of the circular stapler.

FIGS. 24-25B depict a version of stapling head assembly (300) including a switch assembly (3030). It should be understood that this version of stapling head assembly (300) may be readily incorporated into instrument (10). Switch assembly (3030) includes a contact switch (3040) and a rotatable actuator (3020). Actuator (3050) is rotatably secured within a cavity (3032) formed within tubular casing (310) such that actuator (3050) may rotate between a first rotational position (FIG. 25A) and a second rotational position (FIG. 25B). Actuator (3050) is biased toward the first rotational position shown in FIG. 25A via a torsion spring (3052). Contact switch (3040) is positioned adjacent a proximal end of actuator (3050) such that movement of actuator (3050) toward the second rotational position will actuate contact switch (3040) as shown in FIG. 25B. As will be discussed in more detail below, proximal movement of anvil (400), when properly secured to trocar (330), will cause movement of actuator (3050) toward the second rotational position so as to actuate contact switch (3040). Actuation of contact switch (3040) may provide audible, tactile, and/or visible feedback to an operator indicating proper attachment. Various suitable features that may be used to provide such a response to actuation of contact switch (3040) will be apparent to those of ordinary skill in the art in view of the teachings herein. Additionally or alternatively, actuation of contact switch (3040) may enable firing of stapling head assembly (300). In other words, unless contact switch (3040) has been actuated, stapling head assembly (300) may not be fired in some versions.

After anvil (400) is secured to trocar (330), the operator then rotates knob (130) so as to cause trocar (330) and anvil (400) to retract proximally as described above with reference to FIGS. 12A-12C. When trocar (330) and anvil (400) are properly secured to one another, this proximal retraction of trocar (330) and anvil (400) compresses the tissue of tubular anatomical structures (20, 40) between surfaces (412, 322) of anvil (400) and stapling head assembly (300). When trocar (330) and anvil (400) are not properly secured to one another, trocar (330) is retracted proximally without anvil (400) such that the tissue of tubular anatomical structures (20, 40) remains uncompressed. As best seen in FIG. 25B, when trocar (330) and anvil (400) are properly secured to one another, as trocar (330) and anvil (400) are retracted proximally, a proximal end of shank (420) of anvil (400) engages a top surface of actuator (3050) so as to drive actuator (3050) toward the second rotational position so as to actuate contact switch (3040). As mentioned above, such actuation of contact switch (3040) may provide audible, tactile, and/or visible feedback to an operator indicating proper attachment. Additionally or alternatively, such actuation of contact switch (3040) may enable firing of stapling head assembly (300). In other words, unless such actuation of contact switch (3040) has been actuated, stapling head assembly (300) may not be fired.

C. Exemplary Lockout Trocar

FIGS. 26-31C depict an exemplary trocar (3060) that may be readily incorporated into instrument (10) discussed above in place of trocar (330). Trocar (3060) is configured to operate substantially similar to trocar (330) discussed above except for the differences discussed below. For instance, trocar (3060) is operable to translate distally and proximally relative to tubular casing (310) in response to rotation of knob (130). As will be discussed in more detail below, anvil (400) is configured to be attached to trocar (3060) such that translation of trocar (3060) relative to tubular casing (310) is communicated directly to anvil (400) as described above with reference to FIGS. 12A-12C.

Trocar (3060) comprises a shaft (3062) and a head (3064). Head (3064) includes a pointed tip (3066) and an inwardly extending proximal surface (3068). Shaft (3062) thus provides a reduced outer diameter just proximal to head (3064), with surface (3068) providing a transition between that reduced outer diameter of shaft (3062) and the outer diameter of head (3064). While tip (3066) is pointed in the present example, tip (3066) is not sharp. Tip (3066) will thus not easily cause trauma to tissue due to inadvertent contact with tissue. Head (3064) and the distal portion of shaft (3062) are configured for insertion in bore (422) of anvil (400). Proximal surface (3068) and latch shelves (436) have complementary positions and configurations such that latch shelves (436) engage proximal surface (3068) when shank (420) of anvil (400) is fully seated on trocar (3060). Anvil (400) is thus secured to trocar (3060) through a snap fit due to latch members (430).

Figure 27:
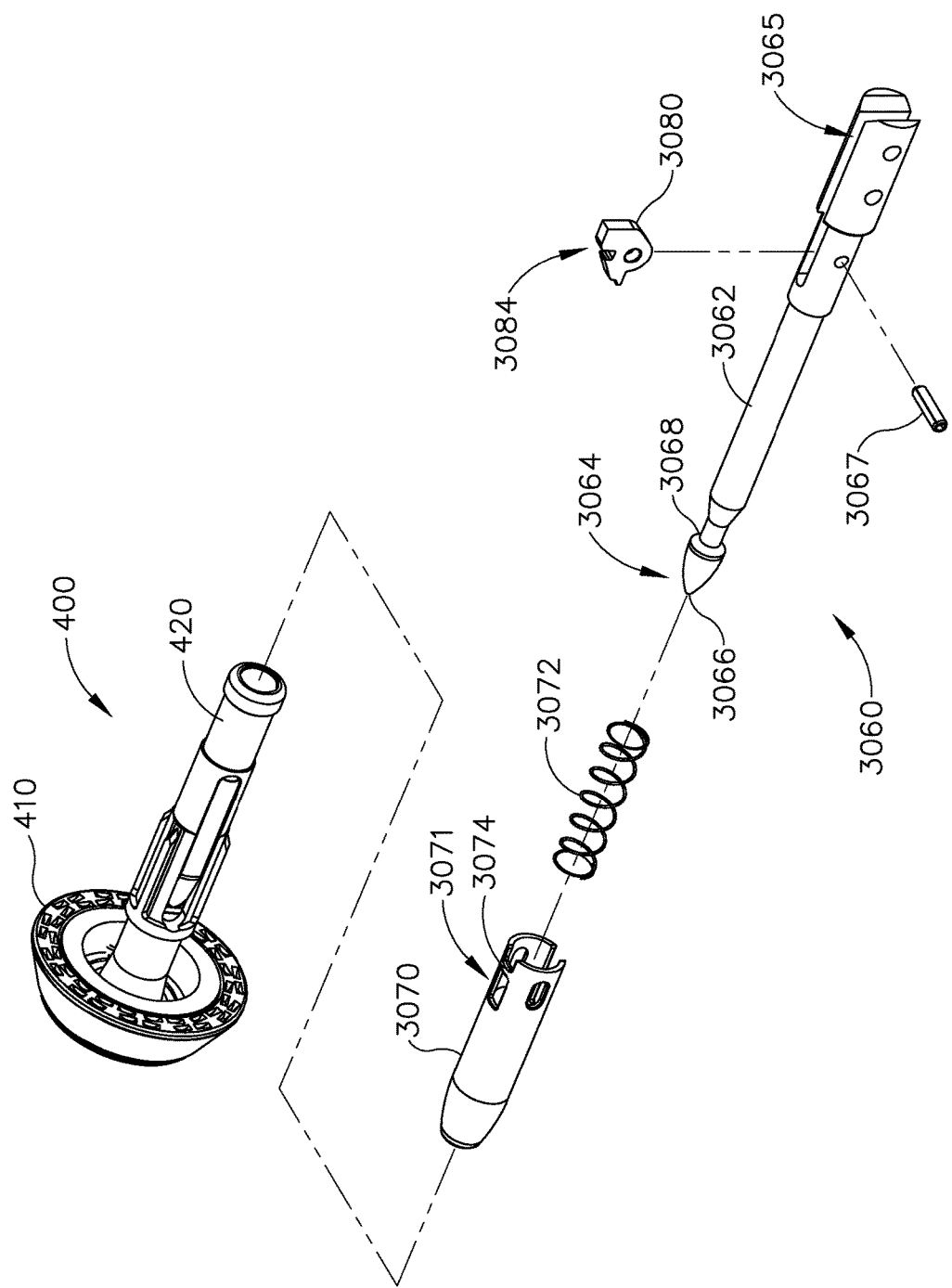
FIG. 27 depicts an exploded perspective view of the trocar of FIG. 26, with an anvil.
Figure 30A:
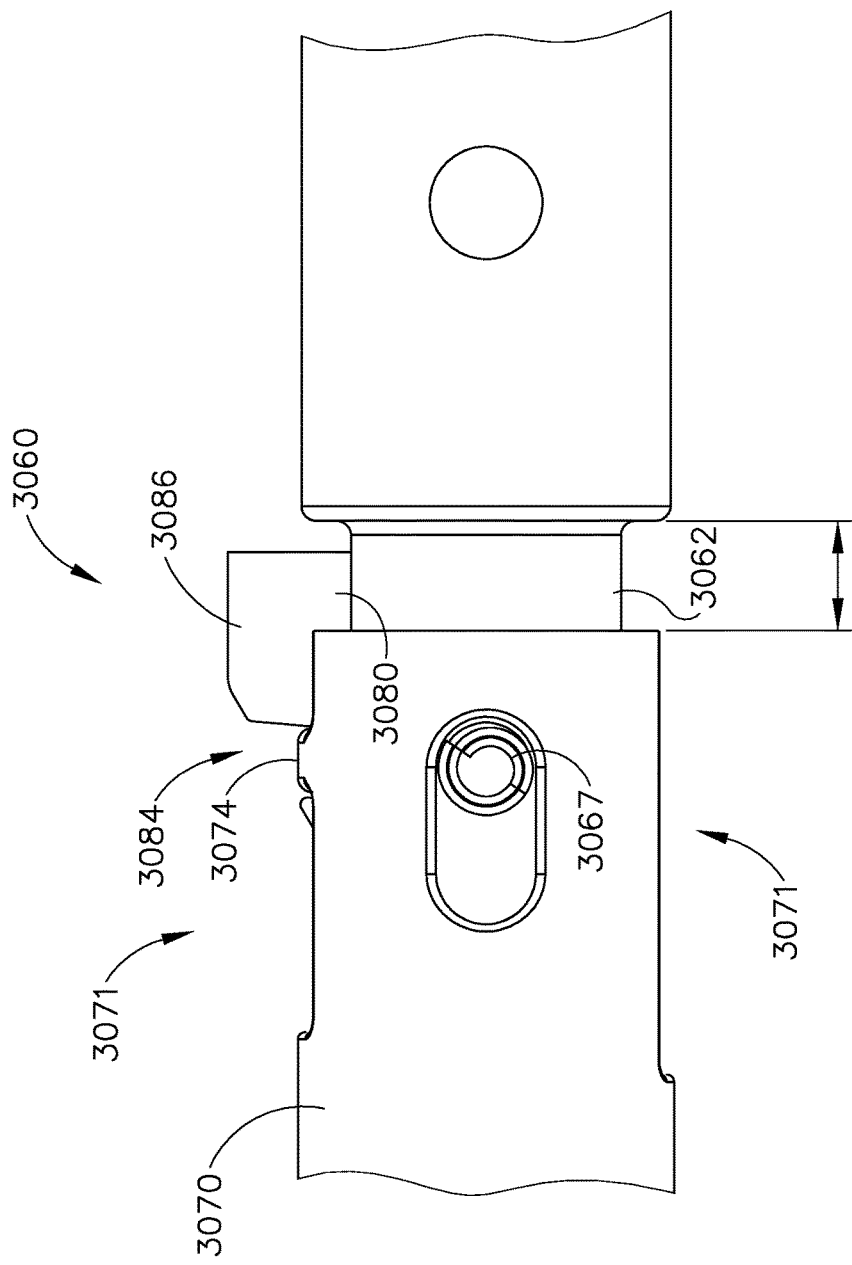
FIG. 30A depicts a detailed side elevational view of the trocar of FIG. 26, with the sleeve member of FIG. 29A in the first position of FIG. 29A, and with the lockout member of FIG. 29A in the first rotational position of FIG. 29A.

Trocar (3060) further comprises a hollow-cylindrical sleeve (3070) and a lockout member (3080). Sleeve (3070) is slidably disposed about shaft (3062) of trocar (3060) such that sleeve (3070) is configured to translate along a length of shaft (3062) between a distal longitudinal position (FIGS. 28B, 29A, 30A) and a proximal longitudinal position (FIGS. 28D, 29C, 30C). As best seen in FIG. 27, a spring (3072), positioned within sleeve (3070) and slidably disposed about shaft (3062), is configured to bias sleeve (3070) toward the distal longitudinal position. Lockout member (3080) is rotatably coupled within a slot (3065) formed in a proximal portion of trocar (3060) via a pin (3067) such that lockout member (3080) is configured to rotate within slot (3065) between a first rotational position (FIGS. 28B, 29A, 30A) and a second rotational position (FIGS. 28D, 29C, 30C). As will be discussed in more detail below, lockout member (3080) further extends through and rotates within a pair of slots (3071) formed within a proximal portion of sleeve (3070). A lateral support member (3074) of sleeve (3070) spans slot (3071) of sleeve (3070) and engages a slot (3084) formed in lockout member (3080) such that, as will be discussed in more detail below, longitudinal translation of sleeve (3070) between the distal longitudinal position and the proximal longitudinal position causes rotation of lockout member (3080) between the first rotational position and the second rotational position and vice versa. Thus, it should be understood that spring (3072) is configured to bias lockout member (3080) toward the first rotational position.

Figure 28A:
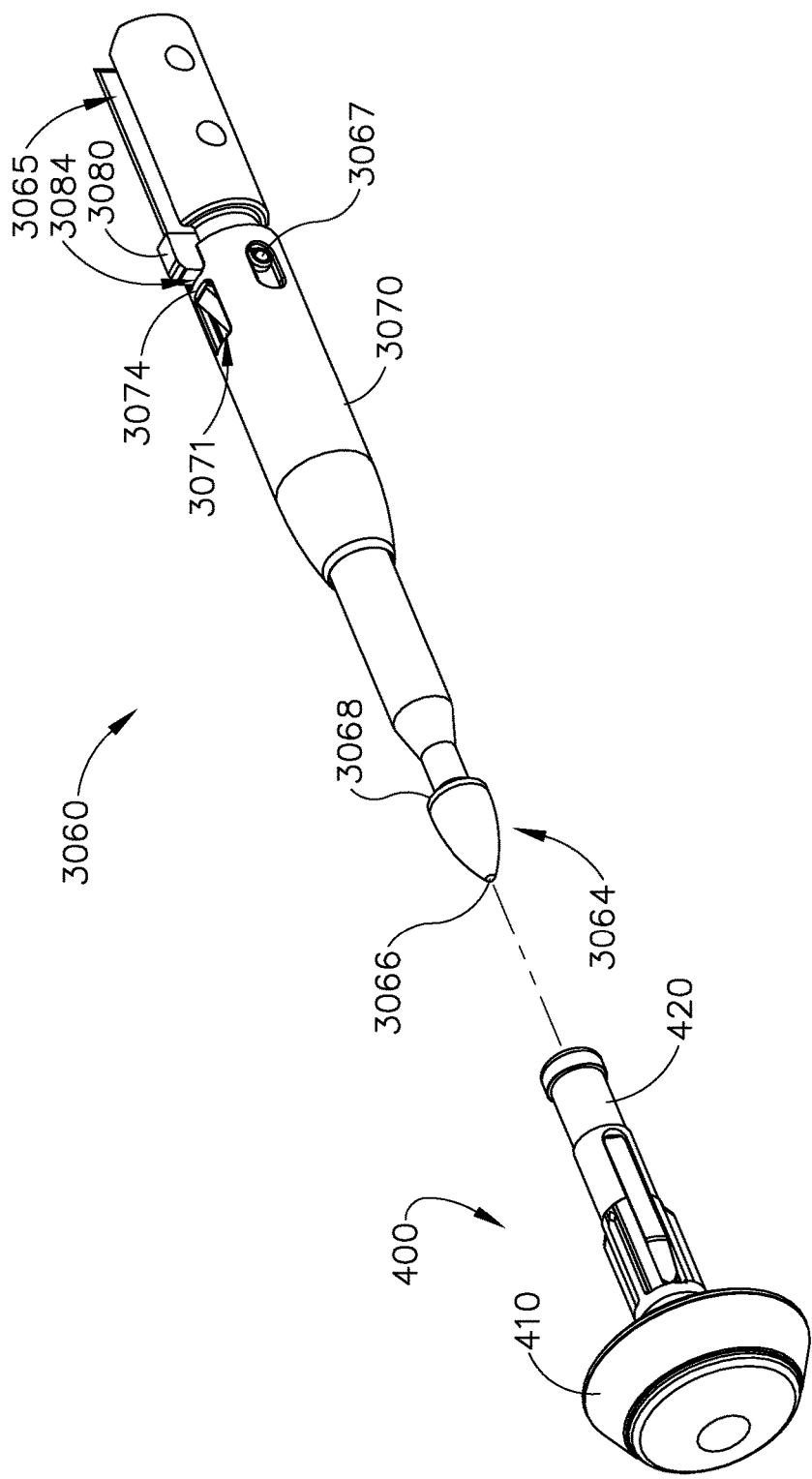
FIG. 28A depicts a perspective view of the trocar of FIG. 26 and the anvil of FIG. 27, with the anvil decoupled from the trocar.
Figure 28B:
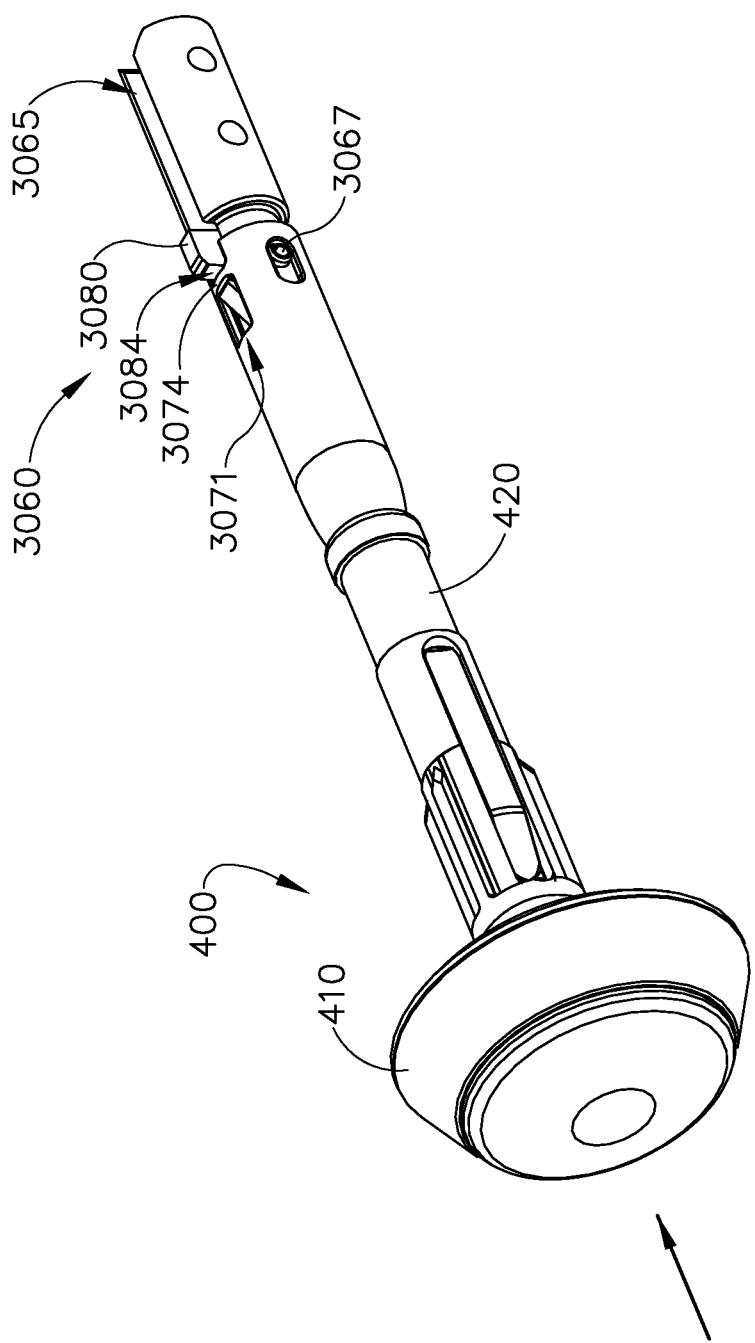
FIG. 28B depicts a perspective view of the trocar of FIG. 26 and the anvil of FIG. 27, with the anvil partially coupled with the trocar.
Figure 28C:
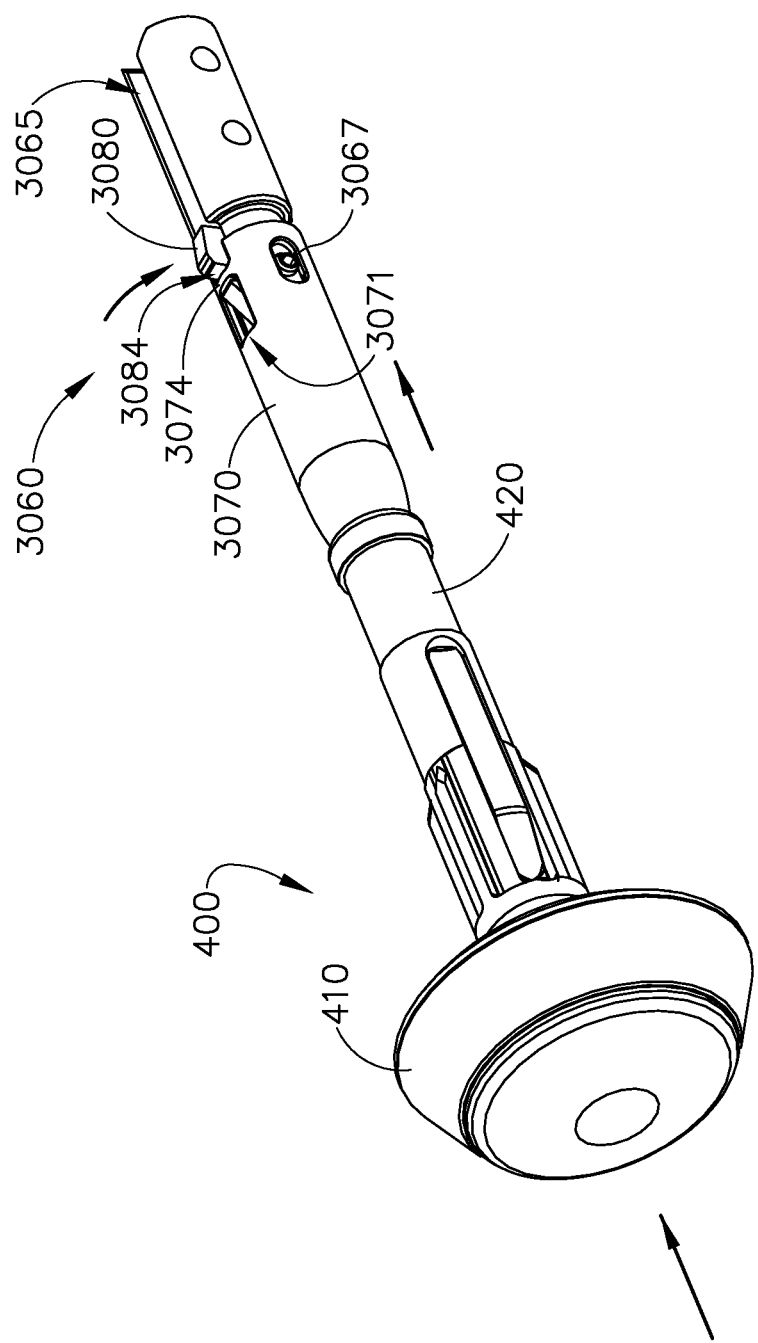
FIG. 28C depicts a perspective view of the trocar of FIG. 26 and the anvil of FIG. 27, with the anvil fully coupled with the trocar.
Figure 28D:
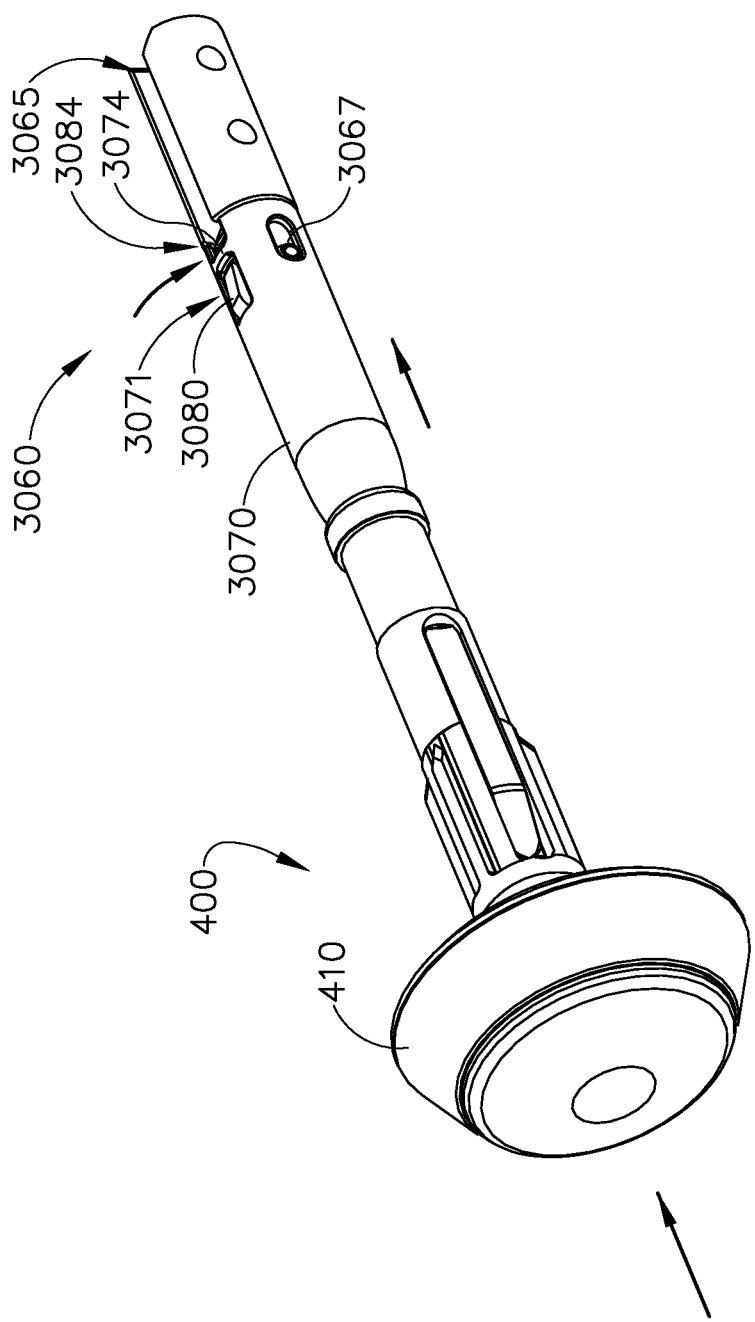
FIG. 28D depicts a perspective view of the trocar of FIG. 26 and the anvil of FIG. 27, with the anvil moved into a fourth position relative to the trocar.

FIG. 28A shows anvil (400) spaced apart from trocar (3060). With anvil (400) in this position, sleeve (3070) is in the distal longitudinal position. As trocar (3060) is initially inserted into bore (422) of shank (420) of anvil (400), a proximal end of shank (420) contacts a distal end of sleeve (3070) as shown in FIG. 28B. As trocar (3060) is further inserted into bore (422), contact between the proximal end of shank (420) and sleeve (3070) drives sleeve (3070) proximally from the distal longitudinal position and into an intermediate position by overcoming the bias of spring (3072) as shown in FIG. 28C. As trocar (3060) is further inserted into bore (422) such that anvil (400) is fully seated on trocar (3060), latch shelves (436) engage proximal surface (3068) of trocar (3060) as discussed above. With anvil (400) fully seated on trocar (3060), sleeve (3070) is driven into the proximal longitudinal position via contact between the proximal end of shank (420) and sleeve (3070) as shown in FIG. 28D.

FIGS. 29A and 30A show sleeve (3070) in the distal longitudinal position. With sleeve (3070) in the distal longitudinal position, lockout member (3080) is in the first rotational position. As best seen in FIG. 30A, with lockout member (3080) in the first rotational position, a tab (3086) of lockout member (3080) extends transversely through slot (3071) of sleeve (3070). As will be discussed in more detail below, tab (3086) is configured to limit translation of trocar (3060) relative to tubular casing (310). As sleeve (3070) is driven into the intermediate longitudinal position, contact between lateral support member (3074) of sleeve (3070) and slot (3084) of lockout member (3080) causes rotation of lockout member (3080) into an intermediate rotational position as shown in FIGS. 29B and 30B. Finally, as sleeve (3070) is driven into the proximal longitudinal position, contact between lateral support member (3074) of sleeve (3070) and slot (3084) of lockout member (3080) causes rotation of lockout member (3080) into the second rotational position as shown in FIGS. 29C and 30C. As best seen in FIG. 30C, with lockout member (3080) in the second rotational position, tab (3086) of lockout member (3080) is rotated completely into sleeve (3070) such that trocar (3060) has a substantially cylindrical profile.

As shown in FIGS. 31A and 31B, if an operator attempts to proximally retract trocar (3060) in the absence of anvil (400) or with anvil (400) not properly attached to trocar (3060), tab (3086) of lockout member (3080) is configured to limit proximal translation of trocar (3060). In particular, in the absence of anvil (400), sleeve (3070) is biased toward the distal longitudinal position via spring (3072) such that lockout member (3080) is rotated into the first rotational position. As mentioned above, with lockout member (3080) in the first rotational position, tab (3086) of lockout member (3080) extends transversely through slot (3071) of sleeve (3070). As shown in FIG. 31B, in the first rotational position, tab (3086) of lockout member (3080) engages tubular casing (310) so as to prevent proximal translation of trocar (3060). Alternatively, with anvil (400) properly attached to trocar (3060), lockout member (3080) is driven into the second rotational position such that tab (3086) of lockout member (3080) is rotated completely into sleeve (3070) such that trocar (3060) may be further proximally translated.

1. Exemplary Circuit Opening Trocar

In some versions of trocar (3060), tab (3086) of lockout member (3080) may be configured to prevent firing of stapling head assembly (300) unless anvil (400) is properly attached to trocar (300). For instance, as shown in FIGS. 32A-33B, if an operator attempts to proximally retract trocar (3060) in the absence of anvil (400) or with anvil (400) not properly attached to trocar (3060), tab (3086) of lockout member (3080) is configured to prevent firing of stapling head assembly (300). In particular, in the absence of anvil (400), sleeve (3070) is biased toward the distal longitudinal position via spring (3072) such that lockout member (3080) is rotated into the first rotational position. As mentioned above, with lockout member (3080) in the first rotational position, tab (3086) of lockout member (3080) extends transversely through slot (3071) of sleeve (3070).

As shown in FIG. 32B, with lockout member (3080) in the first rotational position, tab (3086) of lockout member (3080) is configured to engage a longitudinally translatable link member (3090). Link member (3090) is slidably disposed within tubular casing (310) and extends along the length of shaft assembly (200) into handle assembly (100) such that link member (3090) is configured to translate within and relative to tubular casing (310) and shaft assembly (200). As trocar (3060) is driven proximally relative to tubular casing (310), engagement between tab (3086) and link member (3090) causes proximal longitudinal translation of link member (3090) as shown in FIG. 32C. As shown in FIGS. 33A and 33B, as link member (3090) is translated proximally, a proximal end of link member (3090) is configured to move a switch (3092) from a closed state (FIG. 33A) to an open state (FIG. 33B) so as to prevent firing of stapling head assembly (300). Alternatively, with anvil (400) properly attached to trocar (3060), lockout member (3080) is driven into the second rotational position such that tab (3086) of lockout member (3080) is rotated completely into sleeve (3070) such that trocar (3060) may be proximally retracted without causing proximal longitudinal translation of link member (3090) as shown in FIG. 32D. In the absence of proximal longitudinal translation of link member (3090), switch (3092) remains in the closed position, permitting firing of stapling head assembly (300).

2. Exemplary Circuit Opening Trocar

In other versions of trocar (3060), translation of sleeve (3070) from the distal longitudinal position to the proximal longitudinal position is configured to drive lockout member (3080) from the second rotational position to the first rotational position. In other words, lockout member (3080) of the present example operates opposite of lockout member (3080) discussed above in that such versions of trocar (3060), tab (3086) extends transversely through slot (3071) of sleeve (3070) when anvil (400) is properly secured to trocar (3060). As shown in FIGS. 34A-36B, in the absence of anvil (400), sleeve (3070) is biased toward the distal longitudinal position via spring (3072) such that lockout member (3080) is rotated into the second rotational position. In the present example, with lockout member (3080) in the second rotational position, tab (3086) of lockout member (3080) is rotated completely into sleeve (3070). Alternatively, with anvil (400) properly attached to trocar (3060), lockout member (3080) is driven into the first rotational position such that tab (3086) of lockout member (3080) extends transversely through slot (3071) of sleeve (3070). As shown in FIGS. 34B and 35A, with lockout member (3080) in the first rotational position, tab (3086) of lockout member (3080) is configured to engage a longitudinally translatable link member (3094). Link member (3094) is slidably disposed within tubular casing (310) and extends along the length of shaft assembly (200) into handle assembly (100) such that link member (3094) is configured to translate within and relative to tubular casing (310) and shaft assembly (200). As trocar (3060) is driven proximally relative to tubular casing (310), engagement between tab (3086) and link member (3094) causes proximal longitudinal translation of link member (3094) as shown in FIG. 35B. As shown in FIGS. 36A and 36B, as link member (3094) is translated proximally, a proximal end of link member (3094) is configured to move a switch (3096) from an open state (FIG. 36A) to a closed state (FIG. 36B) so as to permit firing of stapling head assembly (300). It should be understood that in some versions, switch (3096) may be closed via movement of bracket (500) as discussed above in addition to or in lieu of link member (3094).

3. Exemplary Trocar with Contact Switch

In some versions of trocar (3060), tab (3086) of lockout member (3080) may be configured to prevent firing of stapling head assembly (300) unless anvil (400) is properly attached to trocar (300). For instance, as shown in FIGS. 37A and 37B, if an operator attempts to proximally retract trocar (3060) in the absence of anvil (400) or with anvil (400) not properly attached to trocar (3060), tab (3086) of lockout member (3080) is configured to prevent firing of stapling head assembly (300). In particular, in the absence of anvil (400), sleeve (3070) is biased toward the distal longitudinal position via spring (3072) such that lockout member (3080) is rotated into the first rotational position. As mentioned above, with lockout member (3080) in the first rotational position, tab (3086) of lockout member (3080) extends transversely through slot (3071) of sleeve (3070). As shown in FIG. 37B, with lockout member (3080) in the first rotational position, tab (3086) of lockout member (3080) is configured to engage a contact switch (3098) so as to move contact switch (3098) from a closed state (FIG. 37A) to an open state (FIG. 37B) (or vice versa) so as to prevent firing of stapling head assembly (300). Alternatively, with anvil (400) properly attached to trocar (3060), lockout member (3080) is driven into the second rotational position such that tab (3086) of lockout member (3080) is rotated completely into sleeve (3070) such that tab (3086) of lockout member (3080) does not engage contact switch (3098) such that contact switch (3098) remains in the close state to thereby permit firing of stapling head assembly (300).

4. Exemplary Trocar and Lockout Rod

As discussed above, in some versions of trocar (3060), translation of sleeve (3070) from the distal longitudinal position to the proximal longitudinal position will drive lockout member (3080) from the second rotational position to the first rotational position. In other words, in such versions of trocar (3060), tab (3086) extends transversely through slot (3071) of sleeve (3070) when anvil (400) is properly secured to trocar (3060). With lockout member (3080) in the first rotational position, tab (3086) of lockout member (3080) is configured to engage a longitudinally translatable lockout member (3100). As best seen in FIG. 38, lockout member (3100) includes a rigid body (3012) that defines a slot (3104).

As will be discussed in more detail below, lockout member (3100) is configured to selectively prevent and permit actuation of triggers (140, 150), similar to how bracket (500) selectively prevents and permits actuation of triggers (140,

150) as discussed above. In particular, slot (3104) of lockout member (3100) is configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (3102) of lockout member (3100) is configured to prevent this movement of first upright member (144) and safety trigger (140) by engaging the upper end (146) of first upright member (144). Body (3102) thus blocks movement of first upright member (144) and safety trigger (140) until lockout member (3100) is moved to a position where slot (3104) is aligned with upper end (146) to thereby provide clearance for upward movement of first upright member (144). It should therefore be understood that safety trigger (140) cannot be pivoted toward pistol grip (112) until slot (3104) is positioned over upper end (146). When lockout member (3100) is moved to a position to provide clearance for upward movement of first upright member (144), safety trigger (140) may be pivoted out of the way to permit movement of firing trigger (150).

Lockout member (3100) is slidably disposed within tubular casing (310) and extends along the length of shaft assembly (200) into handle assembly (100) such that lockout member (3100) is configured to translate within and relative to tubular casing (310) and shaft assembly (200). As trocar (3060) is driven proximally relative to tubular casing (310), engagement between tab (3086) and lockout member (3100) will cause proximal longitudinal translation of lockout member (3100) from a distal longitudinal position (FIG. 39A) to a proximal longitudinal position (FIG. 39B), similar to link member (3094) discussed above. As lockout member (3100) is translated proximally, lockout member (3100) is moved to a position where slot (3104) is aligned with upper end (146) to thereby provide clearance for upward movement of first upright member (144) as shown in FIG. 39B. When lockout member (3100) is moved to the position shown in FIG. 39B, slot (3104) provides clearance for upward movement of first upright member (144) such that safety trigger (140) may be pivoted out of the way to thereby permit movement of firing trigger (150).

D. Exemplary Trocar with Integral Switch

FIGS. 40-41B depict another exemplary trocar (3200) that may be readily incorporated into instrument (10) discussed above in place of trocar (330). Trocar (3200) of this example is configured to operate substantially similar to trocars (330, 3060) discussed above except for the differences discussed below. For instance, trocar (3200) is operable to translate distally and proximally relative to tubular casing (310) in response to rotation of knob (130). As will be discussed in more detail below, anvil (400) is configured to be attached to trocar (3200) such that translation of trocar (3200) relative to tubular casing (310) is communicated directly to anvil (400) as described above with reference to FIGS. 12A-12C.

Trocar (3200) comprises a shaft (3202) and a head (3204). Head (3204) includes a pointed tip (3206) and an inwardly extending proximal surface (208). Shaft (3202) thus provides a reduced outer diameter just proximal to head (3204), with surface (3208) providing a transition between that reduced outer diameter of shaft (3202) and the outer diameter of head (3204). While tip (3206) is pointed in the present example, tip (3206) is not sharp. Tip (3206) will thus not easily cause trauma to tissue due to inadvertent contact with tissue. Head (3204) and the distal portion of shaft (3202) are configured for insertion in bore (422) of anvil (400). Proximal surface (3208) and latch shelves (436) have complementary positions and configurations such that latch shelves (436) engage proximal surface (3208) when shank (420) of anvil (400) is fully seated on trocar (3200). Anvil (400) is thus secured to trocar (3200) through a snap fit due to latch members (430).

A sidewall of shaft (3202) of trocar (3200) defines a resilient-cantilevered tab (3210). Tab (3210) is formed in trocar (3200) proximal to head (3204) and includes a portion of surface (3208) at its distal end. Tab (3210) is configured to move inwardly and outwardly relative to a hollow interior of trocar (3200). A contact switch (3220) is secured to an interior surface of tab (3210). Contact switch (3220) is in communication with a control circuit (not shown) of instrument (10) via a wire (3221), the control circuit being configured to control firing of stapling head assembly (300). Contact switch (3220) is positioned such that as tab (3210) is driven inwardly, contact switch (3220) is actuated via contact with an opposing interior surface of trocar (3200). In the absence of anvil (400) or with anvil (400) not properly attached to trocar (3200), tab (3210) is biased outwardly to the position shown in FIG. 41A such that contact switch (3220) is not actuated. With anvil (400) properly attached to trocar (3200), contact between an interior surface of shank (420) of anvil (400) drives tab (3210) inwardly to the position shown in FIG. 41B such that contact switch (3220) is actuated. In particular, as discussed above, proximal surface (3208) and latch shelves (436) have complementary positions and configurations such that latch shelves (436) engage proximal surface (3208) when shank (420) of anvil (400) is fully seated on trocar (3200). Contact between latch shelves (436) and proximal surface (3208) when shank (420) of anvil (400) is fully seated on trocar (3200) drives tab (3210) inwardly to the position shown in FIG. 41B such that contact switch (3220) is actuated. Actuating contact switch (3220) will enable firing of stapling head assembly (300). When contact switch (3220) is not actuated, stapling head assembly (300) may not be fired.

E. Exemplary Trocar with Integral Circuit

FIGS. 42-43A depict an exemplary trocar (3300) that may be readily incorporated into instrument (10) discussed above in place of trocar (330). Trocar (3300) of this example is configured to operate substantially similar to trocars (330, 3060, 3200) discussed above except for the differences discussed below. For instance, trocar (3300) is operable to translate distally and proximally relative to tubular casing (310) in response to rotation of knob (130). As will be discussed in more detail below, anvil (400) is configured to be attached to trocar (3300) such that translation of trocar (3300) relative to tubular casing (310) is communicated directly to anvil (400) as described above with reference to FIGS. 12A-12C.

Trocar (3300) comprises a shaft (3302) and a head (3304). Head (3304) includes a pointed tip (3306) and an inwardly extending proximal surface (208). Shaft (3302) thus provides a reduced outer diameter just proximal to head (3304), with surface (3308) providing a transition between that reduced outer diameter of shaft (3302) and the outer diameter of head (3304). While tip (3306) is pointed in the present example, tip (3306) is not sharp. Tip (3306) will thus not easily cause trauma to tissue due to inadvertent contact with tissue. Head (3304) and the distal portion of shaft (3302) are configured for insertion in bore (422) of anvil (400). Proximal surface (3308) and latch shelves (436) have complementary positions and configurations such that latch shelves (436) engage proximal surface (3308) when shank (420) of anvil (400) is fully seated on trocar (3300). Anvil (400) is thus secured to trocar (3300) through a snap fit due to latch members (430).

Trocar (3300) includes an electrical contact surface (3310) disposed about a portion of shaft (3302) proximal to head (3304). Contact surface (3310) is in communication with a control circuit (not shown) of instrument (10) via a wire (3311), the control circuit being configured to control firing of stapling head assembly (300). Contact surface (3310) electrically isolated from shaft (3302) of trocar (3300).

Anvil (400) of the present example further includes an electrical contact surface (3312) that is positioned within shank (420) of anvil (400). Contact surface (3312) is in electrical communication with shank (420) of anvil (400). Contact surfaces (3310, 3312), shaft (3302), shank (420), and wire (3311) are configured to form part of an electrical circuit that selectively enables firing of stapling head assembly (300). In the absence of anvil (400) or with anvil (400) not properly attached to trocar (3300), the electrical circuit is in an open state as shown in FIG. 43A because tip (3306) of trocar (3300) is not in contact with contact surface (3312) of anvil (400). With anvil (400) properly attached to trocar (3300) as shown in FIG. 43B, tip (3306) of trocar (3300) contacts contact surface (3312) of anvil (400), thus providing a path for electrical continuity between shaft (3302) of trocar (3300) and contact surface (3312) of anvil (400). In addition, shank (420) contacts contact surface (3310) of trocar (3300), thereby providing a path for electrical continuity between shank (420) and contact surface (3310). Since shank (420) is also in electrical continuity with contact surface (3312), and since contact surface (3310) is in electrical continuity with wire (3311), it should be understood that the above described contacts provide electrical continuity between shaft (3302) of trocar (3300) and wire (3311) at the stage shown in FIG. 43B. This closes the circuit that enables stapling head assembly (300) to be fired. Until this circuit is closed, stapling head assembly (300) may not be fired. In other words, as in other examples herein, stapling head assembly (300) may not be fired until anvil (400) is fully seated on trocar (3300).

III. Exemplary Trocar with Piercing Features

In some versions of instrument (10) it may desirable to provide trocar (330) with features configured to improve the ability of trocar (330) to pierce or penetrate tissue. For instance, it may be desirable to provide trocar (330) with features that are configured to prevent "tenting" of the tissue as trocar (330) is pushed through the tissue. Various examples of such features will be described in greater detail below; while other examples will be apparent to those of ordinary skill in the art in view of the teachings herein. Moreover, the following teachings may be applied to devices that are used in various other contexts.

FIGS. 44-45B depict an exemplary trocar (3400) that may be readily incorporated into instrument (10) discussed above in place of trocar (330). Trocar (3400) of this example is configured to operate substantially similar to trocars (330, 3060, 3200, 3300) discussed above except for the differences discussed below. For instance, trocar (3400) is operable to translate distally and proximally relative to tubular casing (310) in response to rotation of knob (130). In addition, anvil (400) may be attached to trocar (3400) such that translation of trocar (3400) relative to tubular casing (310) is communicated directly to anvil (400) as described above with reference to FIGS. 12A-12C.

Trocar (3400) comprises a shaft (3402) and a head (3404). Head (3404) includes a pointed tip (3406) and an inwardly extending proximal surface (208). Shaft (3402) thus provides a reduced outer diameter just proximal to head (3404), with surface (3408) providing a transition between that reduced outer diameter of shaft (3402) and the outer diameter of head (3404). While tip (3406) is pointed in the present example, tip (3406) is not sharp. Tip (3406) will thus not easily cause trauma to tissue due to inadvertent contact with tissue. Head (3404) and the distal portion of shaft (3402) are configured for insertion in bore (422) of anvil (400). Proximal surface (3408) and latch shelves (436) have complementary positions and configurations such that latch shelves (436) engage proximal surface (3408) when shank (420) of anvil (400) is fully seated on trocar (3400). Anvil (400) is thus secured to trocar (3400) through a snap fit due to latch members (430).

Trocar (3400) of the present example further includes a plurality of ribs (3410) extending from an exterior surface of head (3404) along a length of head (3404). Ribs (3410) may be sharp or relatively blunt. Ribs (3410) are configured to improve the ability of trocar (3400) to pierce tissue (T) by severing and/or spreading the tissue as trocar (3400) passes through the tissue (T), as shown in FIGS. 45A and 45B. For instance, ribs (3410) may be configured to prevent "tenting" of the tissue (T) as trocar (330) pierces and/or penetrates the tissue (T).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body assembly, wherein the body assembly comprises a proximal end and a distal end; (b) a shaft assembly, wherein the shaft assembly extends distally from the distal end of the body assembly, wherein the shaft assembly comprises a proximal end and a distal end; (c) a stapling assembly, wherein the stapling assembly is disposed at the distal end of the shaft assembly, wherein the stapling assembly is operable to drive a plurality of staples into tissue, wherein the stapling assembly comprises: (i) a trocar, wherein the trocar is configured to selectively move between a distal position to a proximal position within the shaft assembly, and (ii) an anvil, wherein the anvil is selectively coupleable with the trocar, wherein the anvil is configured to move between the distal position and the proximal position when coupled with the trocar; (d) a firing assembly, wherein the firing assembly is coupled with the stapling assembly, wherein the firing assembly is configured to drive movement of the stapling assembly; and (e) a lockout assembly, wherein the lockout assembly is configured to permit actuation of the firing assembly in response to coupling of the anvil with the trocar, and wherein the lockout assembly is configured to prevent actuation of the firing assembly in response to the anvil not being coupled with the trocar.

Example 2

The instrument of Example 1, wherein the lockout assembly comprises a switch assembly, wherein the switch assembly is configured to permit actuation of the firing assembly in response to actuation of the switch assembly.

Example 3

The instrument of Example 2, wherein the anvil is configured to actuate the switch assembly in response to movement of the anvil toward the proximal position when the anvil is coupled with the trocar.

Example 4

The instrument of any one of Examples 2 through 3, wherein the switch assembly comprises an actuator spring, wherein the actuator spring is configured to deform to thereby actuate the switch assembly, wherein the anvil is configured to deform the actuator spring in response to movement of the anvil toward the proximal position when coupled with the trocar.

Example 5

The instrument of any one of Examples 2 through 3, wherein the switch assembly comprises a rotatable actuator, wherein the rotatable actuator is configured to rotate to thereby actuate the switch assembly, wherein the anvil is configured to rotate the rotatable actuator in response to movement of the anvil toward the proximal position when coupled with the trocar.

Example 6

The instrument of Example 1, wherein the trocar comprises the lockout assembly.

Example 7

The instrument of Example 6, wherein the lockout assembly comprises a sleeve and a lockout member.

Example 8

The instrument of Example 7, wherein the sleeve is translatable along a length of the trocar, wherein the lockout member is rotatably coupled with the trocar, wherein the sleeve is configured to translate along a length of the trocar to thereby cause rotation of the lockout member between an exposed position and an unexposed position.

Example 9

The instrument of Example 8, wherein the anvil is translatable along a length of the trocar, wherein the anvil is configured to translate along a length of the trocar to thereby cause translation of the sleeve.

Example 10

The instrument of any one of Examples 7 through 8, wherein the lockout assembly further includes a link member, wherein the link member is configured to translate within and relative to the shaft assembly, wherein the lockout member is configured to cause translation of a link member when the link member is in the exposed position.

Example 11

The instrument of Example 10, wherein the link member is configured to translate to thereby actuate a switch assembly, wherein the switch assembly is configured to permit actuation of the firing assembly in response to actuation of the switch assembly.

Example 12

The instrument of Example 8, wherein the lockout member is configured to actuate a switch assembly when the lockout member is in the exposed position, wherein the switch assembly is configured to permit actuation of the firing assembly in response to actuation of the switch assembly.

Example 13

The instrument of Example 6, wherein the lockout assembly comprises a switch assembly, wherein the switch assembly is configured to permit actuation of the firing assembly in response to actuation of the switch assembly.

Example 14

The instrument of Example 13, wherein the trocar comprises a cantilevered tab, wherein the cantilevered tab is configured to move inwardly relative to a hollow interior of trocar to thereby actuate the switch assembly.

Example 15

The instrument of Example 14, wherein the anvil is configured to couple with the trocar to thereby cause inward movement of the cantilevered tab.

Example 16

The instrument of Example 6, wherein the lockout assembly comprises an electrical circuit, wherein the electrical circuit is configured to close to permit actuation of the firing assembly in response to actuation of the switch assembly.

Example 17

The instrument of Example 16, wherein the anvil is configured to couple with the trocar to thereby close the electrical circuit.

Example 18

The instrument of any one of Examples 1 through 17, wherein the trocar comprises a head defining a distal tip, wherein the trocar comprises a plurality of ribs disposed about the head.

Example 19

A surgical instrument comprising: (a) a body assembly, wherein the body assembly comprises a proximal end and a distal end; (b) a shaft assembly, wherein the shaft assembly extends distally from the distal end of the body assembly, wherein the shaft assembly comprises a proximal end and a distal end; (c) a stapling assembly, wherein the stapling assembly is disposed at the distal end of the shaft assembly, wherein the stapling assembly is operable to drive a plurality of staples into tissue, wherein the stapling assembly comprises: (i) a trocar, wherein the trocar is configured to selectively move between a distal position to a proximal position within the shaft assembly, and (ii) an anvil, wherein the anvil is selectively coupleable with the trocar, wherein the anvil is configured to move between the distal position and the proximal position when coupled with the trocar; and (d) a firing assembly, wherein the firing assembly is coupled with the stapling assembly, wherein the firing assembly is configured to drive movement of the stapling assembly; wherein the trocar comprises a lockout assembly, wherein the lockout assembly is configured to permit actuation of the firing assembly in response to coupling of the anvil with the trocar, and wherein the lockout assembly is configured to prevent actuation of the firing assembly in response to the anvil not being coupled with the trocar.

Example 20

A surgical instrument comprising: (a) a body assembly, wherein the body assembly comprises a proximal end and a distal end; (b) a shaft assembly, wherein the shaft assembly extends distally from the distal end of the body assembly, wherein the shaft assembly comprises a proximal end and a distal end; (c) a stapling assembly, wherein the stapling assembly is disposed at the distal end of the shaft assembly, wherein the stapling assembly is operable to drive a plurality of staples into tissue, wherein the stapling assembly comprises: (i) a trocar, wherein the trocar is configured to selectively move between a distal position to a proximal position within the shaft assembly, and (ii) an anvil, wherein the anvil is selectively coupleable with the trocar, wherein the anvil is configured to move between the distal position and the proximal position when coupled with the trocar; and (d) a firing assembly, wherein the firing assembly is coupled with the stapling assembly, wherein the firing assembly is configured to drive movement of the stapling assembly; wherein the trocar comprises a lockout member, wherein the lockout member is configure to rotate between an exposed position and an unexposed position, wherein the lockout member is configured to permit actuation of the firing assembly when in the unexposed position, and wherein the lockout assembly is configured to prevent actuation of the firing assembly when in the exposed position.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pub. No. 8,453,914 on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pub. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body assembly, wherein the body assembly comprises a proximal end and a distal end;
   (b) a shaft assembly, wherein the shaft assembly extends distally from the distal end of the body assembly, wherein the shaft assembly comprises a proximal end and a distal end;
   (c) a stapling assembly, wherein the stapling assembly is disposed at the distal end of the shaft assembly, wherein the stapling assembly is operable to drive a plurality of staples into tissue, wherein the stapling assembly comprises:
      (i) a trocar, wherein the trocar is configured to selectively move between a distal position to a proximal position within the shaft assembly, and
      (ii) an anvil, wherein the anvil is selectively coupleable with the trocar, wherein the anvil is configured to move between the distal position and the proximal position when coupled with the trocar;
   (d) a firing assembly, wherein the firing assembly is coupled with the stapling assembly, wherein the firing assembly includes a motor configured to drive movement of the stapling assembly; and
   (e) a lockout assembly, wherein the lockout assembly comprises:
      (i) an electrical switch, and
      (ii) a moveable member, wherein a proximal end of the anvil is configured to directly contact and move the moveable member from a first position to a second position, wherein the moveable member in the first position is configured to provide the electrical switch in a first state, wherein the moveable member in the second position is configured to provide the electrical switch in a second state,
   wherein the electrical switch is configured to permit activation of the motor when the anvil is coupled with the trocar, and wherein the electrical switch is configured to prevent activation of the motor when the anvil is not coupled with the trocar.

2. The instrument of claim 1, wherein the electrical switch is configured to permit activation of the motor in response to actuation of the electrical switch.

3. The instrument of claim 1, wherein the moveable member is configured to actuate the electrical switch in response to movement of the anvil toward the proximal position when the anvil is coupled with the trocar.

4. The instrument of claim 1, wherein the moveable member comprises an actuator spring, wherein the actuator spring is configured to deform to thereby actuate the electrical switch assembly, wherein the anvil is configured to deform the actuator spring in response to movement of the anvil toward the proximal position when coupled with the trocar.

5. The instrument of claim 1, wherein the moveable member comprises a rotatable actuator, wherein the rotatable actuator is configured to rotate to thereby actuate the electrical switch, wherein the anvil is configured to rotate the rotatable actuator in response to movement of the anvil toward the proximal position when coupled with the trocar.

6. The instrument of claim 1, wherein the trocar includes a component that engages with the lockout assembly.

7. The instrument of claim 6, wherein the lockout assembly comprises a sleeve and a lockout member.

8. The instrument of claim 7, wherein the sleeve is translatable along a length of the trocar, wherein the lockout member is rotatably coupled with the trocar, wherein the sleeve is configured to translate along a length of the trocar to thereby cause rotation of the lockout member between an exposed position and an unexposed position.

9. The instrument of claim 8, wherein the anvil is translatable along a length of the trocar, wherein the anvil is configured to translate along a length of the trocar to thereby cause translation of the sleeve.

10. The instrument of claim 8, wherein the lockout assembly further includes a link member, wherein the link member is configured to translate within and relative to the shaft assembly, wherein the lockout member is configured to cause translation of a link member when the lockout member is in the exposed position.

11. The instrument of claim 10, wherein the link member is configured to translate to thereby actuate the electrical switch, wherein the electrical switch is configured to permit actuation of the firing assembly in response to actuation of the electrical switch.

12. The instrument of claim 8, wherein the lockout member is configured to actuate the electrical switch when the lockout member is in the exposed position, wherein the electrical switch is configured to permit actuation of the firing assembly in response to actuation of the electrical switch.

13. The instrument of claim 6, wherein the electrical switch is configured to permit actuation of the firing assembly in response to actuation of the electrical switch.

14. The instrument of claim 13, wherein the moveable member comprises a cantilevered tab, wherein the cantilevered tab is configured to move inwardly relative to a hollow interior of trocar to thereby actuate the electrical switch.

15. The instrument of claim 14, wherein the anvil is configured to couple with the trocar to thereby cause inward movement of the cantilevered tab.

16. The instrument of claim 1, wherein the lockout assembly comprises an electrical circuit, wherein the electrical circuit is configured to close to permit actuation of the firing assembly in response to the anvil being coupled with the trocar.

17. The surgical instrument of claim 1, wherein the moveable member comprises a resilient flange.

18. The surgical instrument of claim 17, wherein the electrical switch comprises a dome switch, wherein the resilient flange includes a raised portion configured to be directly contacted by the proximal end of the anvil to move the resilient flange from the first position to the second position to actuate the dome switch.

19. A surgical instrument comprising:
(a) a body assembly, wherein the body assembly comprises a proximal end and a distal end;
(b) a shaft assembly defining a central axis, wherein the shaft assembly extends distally from the distal end of the body assembly, wherein the shaft assembly comprises a proximal end and a distal end;
(c) a stapling assembly, wherein the stapling assembly is disposed at the distal end of the shaft assembly, wherein the stapling assembly is operable to drive a plurality of staples into tissue, wherein the stapling assembly comprises:
  (i) a trocar, wherein the trocar is configured to selectively move along the central axis between a distal position to a proximal position within the shaft assembly, and
  (ii) an anvil, wherein the anvil is selectively coupleable with the trocar, wherein the anvil is configured to move along the central axis between the distal position and the proximal position when coupled with the trocar;
(d) a firing assembly, wherein the firing assembly is coupled with the stapling assembly, wherein the firing assembly includes a motor configured to drive movement of the stapling assembly; and
(e) a lockout assembly, wherein the lockout assembly comprises:
  (i) an electrical switch, and
  (ii) a moveable member, wherein the movable member is moveable transversely relative to the central axis to actuate the electrical switch in response to proximal movement of the anvil when the anvil is coupled with the trocar,
  wherein the electrical switch is configured to permit activation of the motor when the anvil is coupled with the trocar, and wherein the electrical switch is configured to prevent activation of the motor when the anvil is not coupled with the trocar.

20. A surgical instrument comprising:
(a) a body assembly, wherein the body assembly comprises a proximal end and a distal end;
(b) a shaft assembly, wherein the shaft assembly extends distally from the distal end of the body assembly, wherein the shaft assembly comprises a proximal end and a distal end;
(c) a stapling assembly, wherein the stapling assembly is disposed at the distal end of the shaft assembly, wherein the stapling assembly is operable to drive a plurality of staples into tissue, wherein the stapling assembly comprises:
  (i) a trocar, wherein the trocar is configured to selectively move between a distal position to a proximal position within the shaft assembly, and
  (ii) an anvil, wherein the anvil is selectively coupleable with the trocar, wherein the anvil is configured to move between the distal position and the proximal position when coupled with the trocar;
(d) a firing assembly, wherein the firing assembly is coupled with the stapling assembly, wherein the firing assembly includes a motor configured to drive movement of the stapling assembly; and
(e) a moveable member, wherein the moveable member is configured to rotate relative to the trocar between a first rotational position and a second rotational position in response to longitudinal movement of the anvil relative to the shaft assembly, wherein the moveable member is configured to permit activation of the motor when the moveable member is in the first rotational position, and wherein the moveable member is configured to prevent activation of the motor when the moveable member is in the second rotational position.

* * * * *